US006822140B2

(12) United States Patent
Duvick et al.

(10) Patent No.: US 6,822,140 B2
(45) Date of Patent: Nov. 23, 2004

(54) COMPOSITIONS AND METHODS FOR FUMONISIN DETOXIFICATION

(75) Inventors: Jon Duvick, Des Moines, IA (US); Joyce Maddox, Des Moines, IA (US); Jacob Gilliam, Norwalk, IA (US); Otto Folkerts, Guilford, CT (US); Oswald R. Crasta, Branford, CT (US)

(73) Assignees: Pioneer Hi-Bred International, Inc., Des Moines, IA (US); CuraGen Corporation, New Haven, CT (US)

( * ) Notice: Subject to any disclaimer, the term of this patent is extended or adjusted under 35 U.S.C. 154(b) by 0 days.

(21) Appl. No.: 09/882,694

(22) Filed: Jun. 15, 2001

(65) Prior Publication Data

US 2003/0009782 A1 Jan. 9, 2003

Related U.S. Application Data

(62) Division of application No. 09/351,224, filed on Jul. 12, 1999, now Pat. No. 6,388,171.

(51) Int. Cl.[7] .......................... C12N 5/09; C12N 15/09; C12N 15/82; A01H 5/00; A01H 5/10

(52) U.S. Cl. ....................... 800/279; 800/278; 800/298; 800/295; 800/320; 800/320.1; 800/317; 435/468; 435/419

(58) Field of Search ................................ 800/278, 279, 800/298, 295, 320, 320.1, 317, 288; 435/468, 419; 536/23.6, 24.1

(56) References Cited

U.S. PATENT DOCUMENTS

| | | | |
|---|---|---|---|
| 5,178,863 | A | 1/1993 | Toyoda et al. |
| 5,639,949 | A | 6/1997 | Ligon et al. |
| 5,716,820 | A | 2/1998 | Duvick et al. |
| 5,792,931 | A | 8/1998 | Duvick et al. |
| 5,877,273 | A | 3/1999 | Hance et al. |

FOREIGN PATENT DOCUMENTS

| | | |
|---|---|---|
| EP | 0712932 A2 | 5/1996 |
| WO | WO 95/06121 | 3/1995 |
| WO | WO 95/06128 | 3/1995 |
| WO | WO 96/06175 | 2/1996 |
| WO | WO 96/12414 | 5/1996 |
| WO | WO 96/20595 | 7/1996 |
| WO | WO 99/02703 | 1/1999 |
| WO | WO 99/10514 | 3/1999 |
| WO | WO 99/32505 | 7/1999 |

OTHER PUBLICATIONS

Broun et al "Catalytic Plasticity of Fatty Acid Modification Enzymes Underlying Chemical Diversity of Plant Lipids", 1998, Science vol. 282, pp. 1315–1317.*
Lazar et al, "Transforming Growth Factor x: Mutation of Aspartic Acid 47 and Leucine 48 Results in Different Biological Activities", 1988, Molecular Cellular Biology vol. 9 No. 3, pp. 1247–1252.*

Zhang et al. Engineered Detoxification Confers Resistance Against a Pathogenic Bacterium. Nature Biotechnology (1999), vol. 17, pp. 1021–1024.*
Keller et al. (1998) "Identification of a Variant of *Fusarium proliferatum* That Hydrolyzes Fumonisin $B_1$", *J. Agric. Food Chem.*, pp. 2823–2826, vol. 46.

Anzai et al. (1989) "Transgenic Tobacco Resistant To A Bacterial By The Detoxification Of A Pathogenic Toxin", *Mol Gen Genet 219*:492–494, ISSN: 0026–3924, XP002083624.

Anzai et al. (Jan. 1, 1989) "Transgenic tobacco resistant to a bacterial disease by the detoxification of a pathogenic toxin", *Molecular and General Genetics 219*:492–494, XP002083624, ISSN: 0026–3925 the whole document.

Armengaud (Sep. 17, 1998) "Sphingomonas sp. ORFs G1, G3 to G8 and EDO2 gene", EMBL Accession No:AJ223219, XP002133317, see nts 3310–4600.

Armengaud (Nov. 1, 1998) "Flavin–binding monooxygenase–like", PFAM Accession No:PF00743, XP002133310.

Armengaud (Nov. 1, 1998) "Putative Monooxygenase", SWISSPROT Accession No:086908, XP002133318.

Bedzyk et al. (Jun. 15, 1993) "Paracoccus denitrificans electron transfer flavoprotein alpha and beta subunit genes, complete cds's.", EMBL Accession No:L14864, XP002130956 the whole document.

Bennetzen et al. (1992) "Approaches and Progress in the Molecular Cloning of Plant Disease Resistance Genes", *Genetic Engineering 14*:99–124.

Bergeron et al. (Dec. 4, 1997) "Xanthobacter autotrophicus transcriptional activator AldR (aldR) gene, partial cds.; and NAD–dependent chloroacetaldehyde dehydrogenase (aldB) gene, complete cds.", EMBL Accession No:AF029734, XP002121099, see reverse complement of sequence 2447–2066.

Bergeron et al. (Jan. 19, 1998) "Cloning, sequence and expression of a linear plasmid–based and a chromosomal homolog of chloracetaldehyde dehydrogenase–encoding genes in *Xanthobacter autotrophicus* GJ10", *Gene 207*:9–18, XP002121100.

Blackwell et al. (1999) "Oxidative Deamination of Hydrolyzed Fumonisin $B_1$ ($AP_1$) by Cultures of *Exophiala spinifera*", *Natural Toxins 7(I)*:31–38, ISSN: 1056–9014, XP002121276.

Blattner et al. (Oct. 1, 1996) "Hypothetical transcriptional regulator in MODC–BIOA intergenic region", SWISSPROT Accession No:p52696, XP002121103 the whole document.

(List continued on next page.)

*Primary Examiner*—Medina A. Ibrahim
(74) *Attorney, Agent, or Firm*—Alston & Bird LLP

(57) ABSTRACT

Compositions and methods for the complete detoxification of fumonisin and fumonisin degradation products are provided. Particularly, nucleotide sequences corresponding to the detoxification enzymes are provided. The sequences find use in preparing expression cassettes for the transformation of a broad variety of host cells and organisms.

33 Claims, 2 Drawing Sheets

OTHER PUBLICATIONS

Blattner et al. (Jan. 29, 1997) "*Escherichia coli* K–12 MG1655 section 69 of 400 of the complete genome", EMBL Accession No:AE000179, XP002122134 see complement (4647..5663).

Bowen et al. (May 5, 1997) "Cloning and Phylogenetic Analysis of the Genes Encoding Acetohydroxyacid Synthase from the Archaeon *methanococcus aeolicus*", *Gene* 188:77–84, XP002130949 figure 2 and EMBL Accession No:U35458 (May 5, 1997).

Chattopadhyay et al. (1994) "Molecular Cloning And Sequencing Of An Operon, carRS Of *Azospirillum brasilense*, That Codes For A Novel Two–Component Regulatory System: Demonstration Of A Positive Regulatory Role Of carR For Global Control Of Carbohydrate Catabolism", *Journal of Bacteriology* 176(24):7484–7490.

Chattopadhyay et al. (1996) "CarR Gene", TREMBL Accession No. Q43901, XP002121105.

Chen et al. (Apr. 2, 1988) "Homo sapiens P–glycoprotein (PGY1) mRNA, complete cds.", EMBL Accession No. M14758, Abstract No. XP002138295, SWISSPROT Accession No. P08183 (Aug. 1, 1988).

Chen et al. (Jul. 16, 1988) "Acinetobacter sp. Cyclohexanone monooxygenase gene, complete cds", EMBL Accession No:M19029, XP002133308.

Chen et al. (Oct. 1, 1989) "Cyclohexanone Monooxygenase (EC 1.14.13.22)", SWISSPROT Accession No:P12015, XP002133309.

Chen et al. (Oct. 1, 1989) "Flavin–binding monooxygenase–like", PFAM Accession No:PF00743, XP002133310.

Chudhary et al. (Jun. 6, 1998) "483PLA2 Cosmid library of chromosome II *Rhodobacter sphaeroides* genomic clone 483PLA2, genomic survey sequence", EMBL Accession No:AQ012082, XP002130954, the whole document.

Cole et al. (May 10, 1996) "Mycobacterium tuberculosis H37Rv complete genome; segments 41/162", EMBL Accession No:Z73101, XP002130945, the whole document and "Probable Monooxygenase RV0892 (EC 1.14.13.*)","SWISSPROT Accession NO:Q10532 (Oct. 1, 1996).

Cole et al. (Nov. 9, 1997) "Mycobacterium tuberculosis H37Rv complete genome; segment 125–162", EMBL Accession No:AL008883, XP002121098, see sequence 1434–1843.

Cole et al. (Jan. 15, 1998) "Mycobacterium tuberculosis H37Rv complete genome; segment 132/162", EMBL Accession No:AL021287, XP002130944, the whole document and TREMBL Accession No.:053294, (Jun. 1, 1998).

Cole et al. (Feb. 22, 1998) "Mycobacterium tuberculosis H37Rv complete genome; segment 33/162", EMBL Accession No:AL021943, XP002130936, the whole document.

Cole et al. (Feb. 22, 1998) "Mycobacterium tuberculosis H37Rv complete genome; segment 29/162", EMBL Accession No:AL021942, XP002130942, the whole document.

Cole et al. (Mar. 12, 1998) "Mycobacterium tuberculosis H37Rv complete genome; segment 155/162", EMBL Accession No:AL0022121, XP002130947, the whole document.

Coulton et al. (Nov. 18, 1996) "*E. coli* fhuA, fhuC and fhuD genes encoding the ferrichrome–iron receptor and two ferric aerobactin and ferric coprogen transport proteins, complete cds.", EMBL Accession No:M12486, XP002130941, the whole document.

Coulton et al. (Apr. 1, 1988) "Ferrichrome–Iron Receptor Precursor (Ferric Hydroxamate Uptake)", SWISSPROT Accession No:P06971, XP002130942.

Database Biosis 'Online?' Biosciences Information Service (1996) "Styrene metabolism in cytochrome P–450–dependent styrene monooxygenase", Database Accession No. PREV199698822892, Abstract No. XP002138296; and *Applied and Environment Microbiology* (1996) vol. 62, No. 4, pp. 1471–1474.

Du (Dec. 15, 1996) "Mycobacterium tuberculosis sequence from clone Y175", EMBL Accession No:AD000015, XP002121097, see sequence 6027–6064.

Duvick et al. (1998) "Detoxification Of Mycotoxins In Planta As A Strategy For Improving Grain Quality And Disease Resistance: Identification Of Fumonisin–Degrading Microbes From Maize", *Molecular Genetics of Host–Specific Toxins In Plant Disease*, Proceedings of the 3$^{rd}$ Tottori International Symposium Daisen, Tottori, Japan Aug. 24–29 1997 pp 369–381 ISBN 0–7923–4981–4 1998 XP002121275.

Freiberg et al. (Oct. 1, 1996) "Putative transcriptional regulator Y4SM (ORF–1)", SWISSPROT Accession No:P50337, XP002121106, the whole document.

Ghosh et al. (Jan. 30, 1995)"A.brasilense carR gene", EMBL Accession No.:X70360, XP002122135 the whole document and Chattophadhyay et al. (Nov. 1, 1996) "CarR Gene", TREMBL Accession No:Q43901, XP002121105 the whole document.

Heller et al. (Nov. 18, 1996) "*E. coli* btuB gene for the vitamin B12 receptor protein BtuB", EMBL Accession No:M10112, XP002130934, the whole document and SWISSPROT Accession No.:P06129, (Jan. 1, 1998).

Iimura (May 31, 1995) "Msx–2 homolog [human, dental pulp–derived cells, mRNA, 2065 nt]", EMBL Accession No:S75361, XP002130932, the whole document.

Ishiguro et al. (Apr. 22, 1989) "Transposon Tn4311 (from *E. coli* K–12) citrate utilization protein citA and citB genes, complete cds.", EMBL Accession No.:M22041, XP002130953, the whole document.

Ishihara et al. , AB#006450.

Itagaki et al. (Jan. 22, 1998) "*Rhodococcus rhodochrous* gene for steroid monooxygenase, complete cds", EMBL Accession No:AB010439, XP002133311.

Kim et al. (Feb. 4, 1998) "Organization and transcriptional characterization of the cat$_1$ gene cluster in Acinetobacter iwoffii K24", *Biochemical and Biophysical Research Communications* 243:289–294, XP002121104 see fig. 2 and fig. 3 ORFR1.

Klenk et al. (Dec. 1, 1997) "*Archaeoglobus fulgidus* section 144 of 172 of the complete genome", EMBL Accession No:AE000963, XP002130948, the whole document.

Linthorst et al. (1989) "Constitutive Expression of Pathogenesis–Related Proteins PR–1, GRP, and PR–S in Tobacco Has No Effect on Virus Infection", *The Plant Cell* 1:285–291.

Madhusudhan et al. (Jul. 24, 1991) "*Pseudomonas putida* branched–chain keto acid dehydrogenase operon (bkdA1, bkdA1 and bkdA2), transacylase E2 (bkdB), bkdR and lipoamide dehydrogenase (lpdV) genes, complete cds", EMBL Accession No:M57613, XP002121102, see reverse complement of sequence 1405–1010.

Madhusudhan et al. (Nov. 1, 1995) "Bkd operon transcriptional regulator", SWISSPROT Accession No:P42179, XP002121107, the whole document.

Martinez–Salazar et al. (Apr. 1996) "Characterization of the Genes Coding for the Putative Sigma Factor AlgU and Its Regulators MucA, MucB, MucC, and MucD in *Azotobacter vinelandii* and Evaluation of Their Roles in Alginate Biosynthesis", *Journal of Bacteriology* 178(7):1800–1808, XP002130939.

Molnar et al. (Oct. 29, 1992) "Streptomyces sp. Genes for hypothetic proteins", EMBL Accession No:D13457, XP002130955 the whole document.

Morii et al. (Jun. 1, 1998) "Flavin–binding monooxygenase–like" PFAM Accession No:PF00743, XP002133310.

Morii et al. (Jun. 1, 1998) "Steroid Monooxygenase", SWISSPROT Accession No:050641, XP002133312.

Murakami et al. (Jan. 21, 1999) "Cloning And Sequence Analysis Of Two Catechol–Degrading Gene Clusters From The Aniline–Assimilating Bacterium Frateuria Species ANA–18", *Gene* 226(2):189–198.

Murphy et al. (Jan. 26, 1998) "Streptomyces coelicolor cosmid 10A5", EMBL Accession No:AL021529, XP002121096, see reverse complement of 20673–20430.

Nikawa et al. (Nov. 21, 1990) "*Saccharocyces cerevisiae* choline transport protein gene, complete cds.", EMBL Accession No. J05603, Abstract No. XP002138294, SWISSPROT Accession No. P19807 (Jul. 15, 1998).

Oliver et al. (May 27, 1998) "Streptomyces cosmid IC3", EMBL Accession No:AL023702, XP002130938, the whole document.

PCT Invitation To Pay Additional Fees, mailed Mar. 30, 2000, International application No. PCT/US99/15824, International Filing Date Jul. 14, 1999.

Pealing et al. (Nov. 3, 1992) "*Shewanella putrefaciens* flavocytochrome c gene, complete cds.", EMBL Accession No:L04283, XP002130951, the whole document.

Peng et al. (Jul. 1998) "Cloning of a *Sphingomonas paucimobilis* SYK–6 Gene Encoding a Novel Oxygenase That Cleaves Lignin–Related Biphenyl and Characterization of the Enzyme", *Applied and Environmental Microbiology* 64(7):2520–2527, XP002130935.

Perret et al. (Aug. 4, 1993) "Rhizobium sp. ORF–1 and ORF–2", EMBL Accession No:X74314, XP002121101, sequence 463–852.

Peterson et al. (1992) "Cytochrome P–450terp. Isolation and Purification of the Protein and Cloning and Sequencing of Its Operon", *Journal of Biological Chemistry* 267(20):14193–14203, XP002130946 figures 4, 8 and EMBL Accession No.:M91440 (Apr. 17, 1992), and "Probable aldehyde dehydrogenase (EC 1.2.1.3)" SWISSPROT Accession No.:P33008 (Oct. 1, 1993). Plunkett et al. (Dec. 30, 1994) "*Escherichia coli* K–12 chromosomal region from 67.4 to 76.0 minutes", EMBL Accession No:U18997, XP002130937, the whole document.

Rakin et al. (1994) "The Pesticin Receptor of *Yersinia enterocolitica*: A Novel Virulence Factor With Dual Function", *Molecular Microbiology* 13(2):253–263.

Schaap et al. (Jul. 24, 1998) "*Agaricus bisporus* aldA and echA genes", EMBL Accession No. Y17825, Abstract No. XP002138292.

Schmidt et al. (1990) "Cloning and Nucleotide Sequence Of the crtl Gene Encoding Phytoene Dehydrogenase From The Cyanobacterium Aphanocapsa PCC6714", *Gene* 91(1):113–117.

Seebacher et al. (Oct. 17, 1996) "*R. norvegicus* mRNA for laminin chain, 765bp", EMBL Accession No:Y08882, XP002130943, the whole document.

Seeger (Jul. 2, 1998) "Streptomyces coelicolor cosmid 8A6", EMBL Accession No:AL031013, XP002130933, the whole document.

Van Der Rest (Apr. 4, 1990) "Klebsiella pneumoniae cit(+) gene for citrate carrier protein", EMBL Accession No:X51479, XP002130931, the whole document.

Vlcek et al. (May 13, 1998) "*Rhodobacter capsulatus* strain SB1003, partial genome", EMBL Accession No:AF010496, XP002130950, the whole document.

Walczak et al. (Jul. 14, 1998) "*Streptomyces griseus* subsp. Griseus nonactin biosynthesis gene cluster, partial sequence", EMBL Accession No:AF74603, XP002130952, the whole document.

Wang et al. (May 15, 1996) "Pseudomonas putida p–cymene catabolism (cym) and p–cumate catabolism (cmt) operons and enol–coenzyme A hydratase gene, complete cds.", EMBL Accession No. U24215, Abstract No. XP002138293, SPTREMBL Accession No. 033455 (Jan. 1, 1995).

Willins et al. (Aug. 4, 1990) "*E. coli* leucine–responsive–regulatory protein (Lrp) gene, complete cds.", EMBL Accession No:M35869, XP002122136 see sequence 1.495 and Willins et al. (Feb. 1, 1991) "Leucine–responsive regulatory protein", SWISSPROT Accession No.:P19494, XP002121108 the whole document.

Willins et al. (1991) "Leucine–Responsive Regulatory Protein", SWISSPROT Accession No. P19494, XP002121108.

Willins et al. (1991) "Characterization Of Lrp, an *Escherichia coli* Regulatory Protein That Mediates A Global Response To Leucine", *The Journal of Biological Chemistry* 266(17):10768–10774.

* cited by examiner

US 6,822,140 B2

COMPOSITIONS AND METHODS FOR FUMONISIN DETOXIFICATION

CROSS-REFERENCE TO RELATED APPLICATIONS

This Application is a Divisional Application of U.S. patent application Ser. No. 09/351,224, filed Jul. 12, 1999 and issued as U.S. Pat. No. 6,388,171 on May 14, 2002 herein incorporated by reference.

FIELD OF THE INVENTION

The invention relates to compositions and methods for detoxification or degradation of fumonisin or AP1. The method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides, and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. In the case of pathogens that produce toxins that are undesirable to mammals or other animals that feed on the crop plants, interference with toxin production, storage, or activity can be beneficial.

Since their discovery and structural elucidation in 1988 (Bezuidenhout et al. (1988) *Journal Chem. Soc., Chem. Commun.* 1988:743–745), fumonisins have been recognized as a potentially serious problem in maize-fed livestock. They are linked to several animal toxicoses including leukoencephalomalacia (Marasas et al. (1988) *Onderstepoort J. Vet. Res.* 55:197–204; Wilson et al. (1990) *American Association of Veterinary Laboratory Diagnosticians: Abstracts* 33rd *Annual Meeting,* Denver, Colo., Madison, Wis., USA) and porcine pulmonary edema (Colvin et al. (1992) *Mycopathologia* 117:79–82). Fumonisins are also suspected carcinogens (Geary et al. (1971) *Coord. Chem. Rev.* 7:81; Gelderblom et al. (1991) *Carcinogenesis* 12:1247–1251; Gelderblom et al. (1992) *Carcinogenesis* 13:433–437). Fusarium isolates in section Liseola produce fumonisins in culture at levels from 2 to >4000 ppm (Leslie et al. (1992) *Phytopathology* 82:341–345). Isolates from maize (predominantly mating population A) are among the highest producers of fumonisin (Leslie et al., supra). Fumonisin levels detected in field-grown maize have fluctuated widely depending on location and growing season, but both preharvest and postharvest surveys of field maize have indicated that the potential for high levels of fumonisins exists (Murphy et al. (1993) *J. Agr. Food Chem.* 41:263–266). Surveys of food and feed products have also detected fumonisin (Holcomb et al (1993) *J. Agr. Food Chem.* 41:764–767; Hopmans et al. (1993) *J. Agr. Food Chem.* 41:1655–1658); Sydenham et al. (1991) *J. Agr. Food Chem.* 39:2014–2018). The etiology of Fusarium ear mold is poorly understood, although physical damage to the ear and certain environmental conditions can contribute to its occurrence (Nelson et al. (1992) *Mycopathologia* 117:29–36). Fusarium can be isolated from most field grown maize, even when no visible mold is present. The relationship between seedling infection and stalk and ear diseases caused by Fusarium is not clear. Genetic resistance to visible kernel mold has been identified (Gendloff et al. (1986) *Phytopathology* 76:684–688; Holley et al. (1989) *Plant Dis.* 73:578–580), but the relationship to visible mold to fumonisin production has yet to be elucidated.

Fumonisins have been shown in in vitro mammalian cell studies to inhibit sphingolipid biosynthesis through inhibition of the enzyme sphingosine N-acetyl transferase, resulting in the accumulation of the precursor sphinganine (Norred et al. (1992) *Mycopathologia* 117:73–78; Wang et al. (1991) *Biol. Chem.* 266:14486; Yoo et al. (1992) *Toxicol. Appl. Pharmacol.* 114:9–15; Nelson et al. (1993) *Annu. Rev. Phytpathol.* 31:233–252). It is likely that inhibition of this pathway accounts for at least some of fumonisin's toxicity, and support for this comes from measures of sphinganine:sphingosine ratios in animals fed purified fumonisin (Wang et al. (1992) *J. Nutr.* 122:1706–1716). Fumonisins also affect plant cell growth (Abbas et al. (1992) *Weed Technol.* 6:548–552; Van Asch et al. (1992) *Phytopathology* 82:1330–1332; Vesonder et al. (1992) *Arch. Environ. Contam. Toxicol.* 23:464–467). Kuti et al. (1993) (Abstract, Annual Meeting American Phytopathological Society, Memphis, Tenn.: APS Press) reported on the ability of exogenously added fumonisins to accelerate disease development and increase sporulation of *Fusarium moniliform* and *F. oxysporum* on tomato.

Enzymes that degrade the fungal toxin fumonisin to the compound AP1 have been identified in U.S. Pat. No. 5,716,820, U.S. Pat. No. 6,025,188, and U.S. Pat. No. 6,229,071, hereby incorporated by reference. Plants expressing a fumonisin esterase enzyme, infected by fumonisin producing fungus, and tested for fumonisin and AP1 were found to have low levels of fumonisin but high levels of AP1. AP1 is less toxic than fumonisin to plants and probably also animals, but contamination with AP1 is still a concern. The best result would be complete detoxification of fumonisin to a non-toxic form. Therefore enzymes capable of degrading AP1 are necessary for the further detoxification of fumonisin.

SUMMARY OF THE INVENTION

Compositions and methods for catabolism and detoxification of fumonisin and fumonisin-degradation products as well as fumonisin-related toxins are provided. In particular, proteins involved in catabolism and transmembrane transport of fumonisin and fumonisin catabolic products are provided. Nucleotide sequences corresponding to the proteins are also included. The compositions are useful in the detoxification and degradation of fumonisin. The nucleotide sequences can be used in expression cassettes for transformation of host cells of interest. The compositions and methods of the invention are steps in a catabolic pathway for fumonisin. Thus, organisms can be genetically modified to provide for the catabolism and detoxification of fumonisin and fumonisin-related toxins.

In particular, expression cassettes for expression of the enzymes in plants and other organisms are provided as well as transformed plants and other host cells.

DETAILED DESCRIPTION OF THE INVENTION

Figure 1:
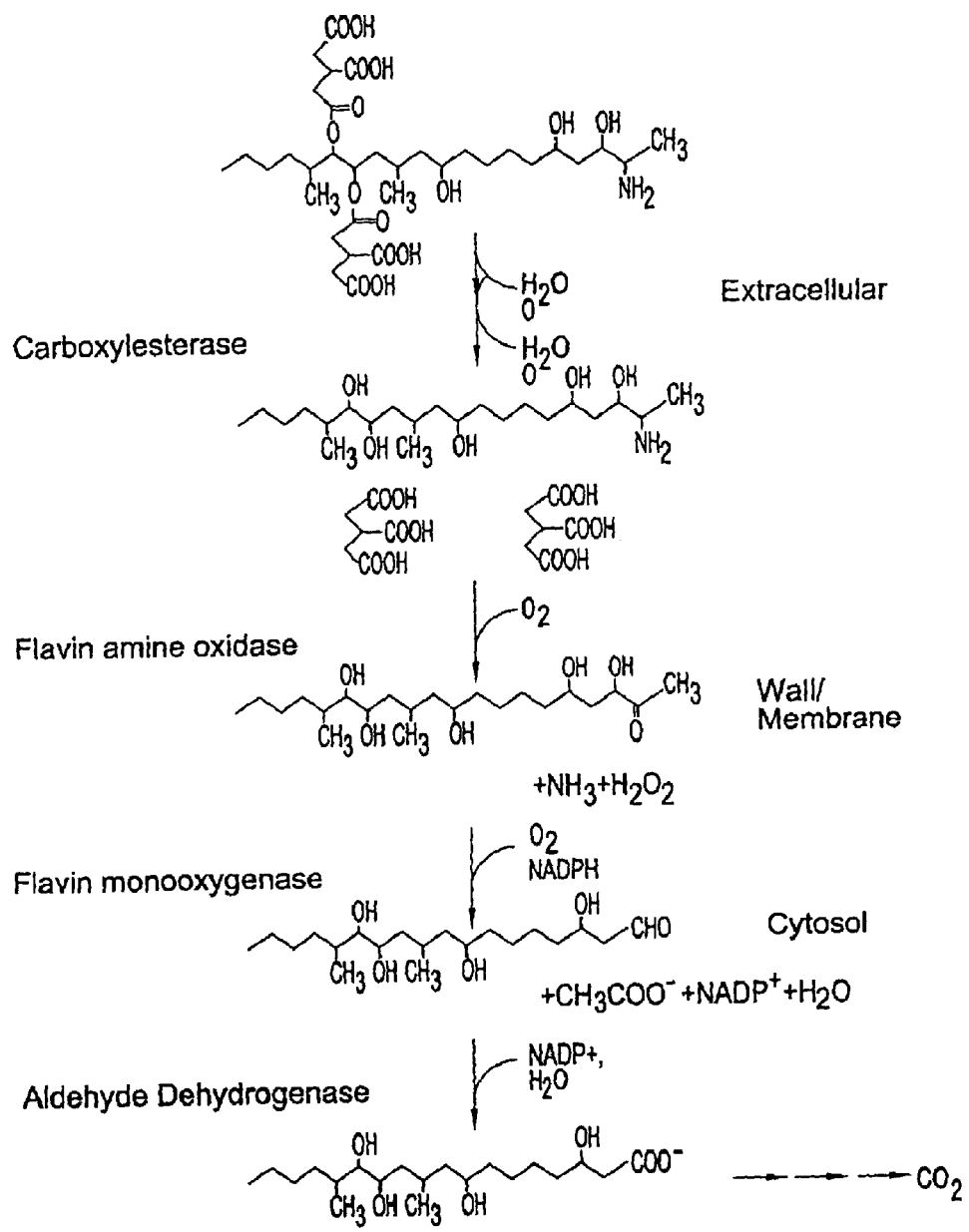
FIG. 1 sets forth the proposed pathway for fumonisin degradation by *Exophiala spinifera*.

The catabolic pathway for detoxification and degradation of fumonisin is provided. Particularly, enzymes involved in the degradation of fumonisin from *Exophiala spinifera* (American Type Culture Collection Deposit No. 74269) and nucleotide sequences encoding such enzymes are disclosed. Such enzymes and nucleotide sequences find use in the breakdown of fumonisin and fumonisin-related toxins as well as degradation products thereof. In this regard, enzymes can be synthesized and utilized or, alternatively, organisms can be transformed with the DNA sequences of the invention and used to detoxify fumonisin.

A proposed pathway for the degradation of fumonisin by *Exophiala spinifera* is provided in FIG. 1. The present invention encompasses enzymes and nucleotide sequences encoding the enzymes involved in this degradation pathway for fumonisin. Compositions of the invention include a flavin monooxygenase, an aldehyde dehydrogenase, a permease, and a p-glycoprotein that are involved in the fumonisin degradation pathway. In particular, the present invention provides for isolated nucleic acid molecules comprising nucleotide sequences encoding the amino acid sequences shown in SEQ ID NOS:3, 5, 8, and 11, or the nucleotide sequences encoding the DNA sequences obtained from the overlapping clones deposited in a bacterial host with the American Type Culture Collection and assigned Accession Number PTA-299. By "DNA sequence obtained from the overlapping clones" is intended that the DNA sequence of the fumonisin degrading enzymes can be obtained by sequencing the individual clones which together comprise the entire fumonisin degrading enzymes. Further provided are polypeptides having an amino acid sequence encoded by a nucleic acid molecule described herein, for example those set forth in SEQ ID NOS:1, 2, 4, 6, 7, 9 and 10, the DNA sequences obtained from the overlapping clones deposited in a bacterial host with the American Type Culture Collection and assigned Accession Number PTA-299, and fragments and variants thereof.

Ten plasmids containing overlapping clones were deposited with the American Type Culture Collection, Manassas, Va., and assigned Accession Number PTA-299. The plasmids designated as F_perm3.5 and F_perm4.4 contain common sequences at the regions were they overlap to form the nucleotide sequence encoding a permease. The plasmids designated as F_p-glyco1L4, F_p-glyco5.13, and F_glyco6.43 contain common sequences at the regions were they overlap to form the nucleotide sequence encoding a p-glycoprotein. And the plasmids designated F_Alde1.1, F_Alde2.2, and F_Alde2.5 contain common sequences at the regions were they overlap to form the nucleotide sequence of an aldehyde dehydrogenase. One of skill in the art by sequencing the clones and aligning the overlap may obtain the entire sequence of the permease, the p-glycoprotein, and the aldehyde dehydrogenase.

These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence degrade or catabolize fumonisin. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a fumonisin-degrading nucleotide sequence that encodes a biologically active portion of a fumonisin-degrading protein of the invention will encode at least 15, 25, 30, 50, 100, 150, 200, or 250, 300, 400, 500, 600, 700, 800, 900, 1,000, 1,100, 1,200 contiguous amino acids, or up to the total number of amino acids present in a full-length fumonisin-degrading protein of the invention (for example, 545, 487, 525, 1,263 amino acids for SEQ ID NOS:3, 5, 8 and 11, respectively). Fragments of a fumonisin-degrading nucleotide sequence that are useful as hybridization probes for PCR primers generally need not encode a biologically active portion of a fumonisin-degrading protein.

Thus, a fragment of a fumonisin-degrading nucleotide sequence may encode a biologically active portion of a fumonisin-degrading protein, or it may be a fragment that can be used as a hybridization probe or PCR primer using methods disclosed below. A biologically active portion of a fumonisin-degrading protein can be prepared by isolating a portion of one of the fumonisin-degrading nucleotide sequences of the invention, expressing the encoded portion of the fumonisin-degrading protein (e.g., by recombinant expression in vitro), and assessing the activity of the encoded portion of the fumonisin-degrading protein. Nucleic acid molecules that are fragments of a fumonisin-degrading nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1500, 1,600, 1,800, 2,000, 2,200, 2,400, 2,600, 2,800, 3,000, 3,200, 3,400, 3,600, 3,800, 3,900 nucleotides, or up to the number of nucleotides present in a full-length fumonisin-degrading nucleotide sequence disclosed herein (for example, 1,691, 1,638, 1,464, 1,764, 1,578, 3,999, 3,792 nucleotides for SEQ ID NOS:1, 2, 4, 6, 7, 9, and 10 respectively).

By "variants" is intended substantially similar sequences. For nucleotide sequences, conservative variants include those sequences that, because of the degeneracy of the genetic code, encode the amino acid sequence of one of the fumonisin-degrading polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a fumonisin-degrading protein of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the fumonisin-degrading proteins can be prepared by mutations in the DNA. Methods for mutagenesis and nucleotide sequence alterations are well known in the art. See, for example, Kunkel (1985) *Proc. Natl. Acad. Sci USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ability to degrade or catabolize fumonisin. Obviously, the mutations that will be made in the DNA encoding the variant must not place the sequence out of reading frame and preferably will not create complementary regions that could produce secondary mRNA structure. See, EP Patent Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by a decrease or loss in the toxic activity of fumonisin or AP1.

Variant nucleotide sequences and proteins also encompass sequences and proteins derived from a mutagenic and recombinogenic procedure such as DNA shuffling. With such a procedure, one or more different fumonisin-degrading coding sequences can be manipulated to create a new fumonisin-catabolizing possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the fumonisin-degrading genes of the invention and other known fumonisin-catabolizing genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The carboxylesterase and amine oxidase have been previously described in U.S. Pat. No. 5,716,820, U.S. Pat. No. 6,025,188, and U.S. Pat. No. 6,229,071. Such disclosures are herein incorporated by reference. Thus, the sequences of the invention can be used in combination with those previously disclosed or disclosed in U.S. Pat. No. 6,211,435 and U.S. Pat. No. 6,211,434, both entitled "Amino Polyolamine Oxidase Polynucleotides and Related Polypeptides and Methods of Use", herein incorporated by reference. These exemplary amino polyolamine oxidase nucleotide sequences are set forth in SEQ ID NOs: 16, 18, 20, 22, 24, 26, 28, 30, and 32. SEQ ID NO:16 is the same as SEQ ID NO:5 from U.S. Pat. No. 6,211,435; SEQ ID NO:18 is the same as SEQ ID NO:10 from U.S. Pat. No. 6,211,435; and SEQ ID NO:20 is the same as SEQ ID NO:22 from U.S. Pat. No. 6,211,435. The nucleotide sequences set forth in SEQ ID NOs: 16, 18, and 20 encode polypeptides having the amino acid sequences set forth in SEQ ID NOs: 17, 19, and 21, respectively (which are the same as SEQ ID NOs: 6, 11, and 23 from U.S. Pat. No. 6,211,435, respectively). Amino polyolamine oxidase nucleotide sequences of U.S. Pat. No. 6,211,434, with introns removed, are set forth in SEQ ID NOs:22 (SEQ ID NO:35 from U.S. Pat. No. 6,211,434), 24 (SEQ ID NO:37 from U.S. Pat. No. 6,211,434), 26 (SEQ ID NO:39 from U.S. Pat. No. 6,211,434), 28 (SEQ ID NO:41 from U.S. Pat. No. 6,211,434), 30 (SEQ ID NO:43 from U.S. Pat. No. 6,211,434), and 32 (SEQ ID NO:45 from U.S. Pat. No. 6,211,434). The nucleotide sequences set forth in SEQ ID NOs: 22, 24, 26, 28, 30, and 32 encode polypeptides having the amino acid sequences set forth in SEQ ID NOs: 23, 25, 27, 29, 31, and 33, respectively (which are the same as SEQ ID NOs: 36, 38, 40, 42, 44, and 46 from U.S. Pat. No. 6,211,434, respectively). The enzymes and nucleotide sequences of the present invention provide a means for continued catabolism of the fumonisin-degradation products obtained after degradation with at least the carboxylesterase and amine oxidase.

The practice of the present invention will employ, unless otherwise indicated, conventional techniques of botany, microbiology, tissue culture, molecular biology, chemistry, biochemistry, and recombinant DNA technology, which are within the skill of the art. Such techniques are explained fully in the literature. See, e.g., Langenheim and Thimann, (1982) Botany: *Plant Biology and Its Relation to Human Affairs* (John Wiley); Vasil, ed. (1984) *Cell Culture and Somatic Cell Genetics of Plants,* Vol. 1; Stanier et al. (1986) *The Microbial World* (5th ed., Prentice-Hall); Dhringra and Sinclair (1985) *Basic Plant Pathology Methods* (CRC Press); Maniatis et al. (1982) *Molecular Cloning: A Laboratory Manual* (Cold Spring Harbor Laboratory Press, Cold Spring Harbor, N.Y.); Glover, ed. (1985) *DNA Cloning,* Vols. I and II; Gait, ed. (1984) *Oligonucleotide Synthesis;* Hames and Higgins, eds. (1984) *Nucleic Acid Hybridization;* and the series *Methods in Enzymology* (Colowick and Kaplan, eds., Academic Press, Inc.).

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae, and protozoa, as well as other unicellular structures.

A "fumonisin-producing microbe" is any microbe capable of producing the mycotoxin fumonisin or analogues thereof. Such microbes are generally members of the fungal genus Fusarium, as well as recombinantly derived organisms that have been genetically altered to enable them to produce fumonisin or analogues thereof.

By "degrading or catabolizing fumonisin" is meant any modification to the fumonisin or AP1 molecule that causes a decrease or loss in its toxic activity. Such a change can comprise cleavage of any of the various bonds, oxidation, reduction, the addition or deletion of a chemical moiety, or any other change that affects the activity of the molecule. In a preferred embodiment, the modification includes hydrolysis of the ester linkage in the molecule as a first step and then oxidative deamination. Furthermore, chemically altered fumonisin can be isolated from cultures of microbes that produce an enzyme of this invention, such as by growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as porcines and equines. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies, e.g., using cell suspension cultures.

For purposes of the invention, the fumonisin or fumonisin degradation products will be degraded to at least about 50% to about 10% or less of the original toxicity, preferably about 30% to about 5% or less, more preferably about 20% to about 1% or less.

By "fumonisin esterase" is meant any enzyme capable of hydrolysis of the ester linkage in fumonisin. Two examples of such enzymes are ESP1 and BEST1 found in U.S. Pat. No. 5,716,820, U.S. Pat. No. 6,025,188, and U.S. Pat. No. 6,229,071. The ESP1 nucleotide sequence is set forth in SEQ ID NO:12 and is the same as SEQ ID NO:15 from U.S. Pat. No. 6,025,188. This nucleotide sequence encodes a polypeptide having the amino acid sequence set forth in SEQ ID NO:13 (which is the same as SEQ ID NO:10 from U.S. Pat. No. 6,025,188). The BEST1 nucleotide sequence is set forth in SEQ ID NO:14 and is the same as SEQ ID NO:11 from U.S. Pat. No. 6,025,188. This nucleotide sequence encodes a polypeptide having the amino acid sequence set forth in SEQ ID NO: 15 (which is the same as SEQ ID NO:12 from U.S. Pat. No. 6,025,188).

By "structurally related mycotoxin" is meant any mycotoxin having a chemical structure related to a fumonisin such as fumonisin B1, for example AAL toxin, fumonisin B2, fumonisin B3, fumonisin B4, fumonisin C1, fumonisin A1 and A2, and their analogues, as well as other mycotoxins having similar chemical structures that would be expected to be detoxified by activity of the fumonisin degradative enzymes elaborated by *Exophiala spinifera,* American Type Culture Collection Accession No. 74269, *Rhinocladiella atrovirens,* American Type Culture Collection Accession No. 74270, or the bacterium of American Type Culture Collection Accession No. 55552.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Persing et al., ed. (1993) *Diagnostic Molecular Microbiology: Principles and Applications* (American Society for Microbiology, Washington, D.C.). The product of amplification is termed an amplicon.

By "host cell" is meant a cell that contains a vector and supports the replication and/or expression of the expression vector. Host cells may be prokaryotic cells such as *E. coli,* or eukaryotic cells such as yeast, insect, amphibian, or mammalian cells. Preferably, host cells are monocotyledonous or dicotyledonous plant cells, including but not limited to maize, sorghum, sunflower, soybean, wheat, alfalfa, rice, cotton, and tomato. A particularly preferred monocotyledonous host cell is a maize host cell.

The term "hybridization complex" includes reference to a duplex nucleic acid structure formed by two single-stranded nucleic acid sequences selectively hybridized with each other.

As used herein, "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogues thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including inter alia, simple and complex cells.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria that comprise genes expressed in plant cells, such as Agrobacterium or Rhizobium. Examples are promoters that preferentially initiate transcription in certain tissues, such as leaves, roots, seeds, fibers, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Another type of promoter is a developmentally regulated promoter. For example, a promoter that drives expression during pollen development. Tissue-preferred, cell type specific, developmentally regulated, and inducible promoters constitute the class of "non-constitutive" promoters. A "constitutive" promoter is a promoter that is active under most environmental conditions. Constitutive promoters are known in the art and include, for example, 35S promoter (Meyer et al. (1997) *J. Gen. Virol.* 78:3147–3151); ubiquitin; as well as those disclosed in U.S. Pat. Nos. 5,608,149; 5,608,144; 5,604,121; 5,569,597; 5,466,785; 5,399,680; 5,268,463; 5,608,142.

As used herein, "recombinant" includes reference to a cell or vector that has been modified by the introduction of a heterologous nucleic acid or that the cell is derived from a cell so modified. Thus, for example, recombinant cells express genes that are not found in identical form within the native (nonrecombinant) form of the cell or express native genes that are otherwise abnormally expressed, underexpressed, or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The nucleotide sequences of the invention can be used to isolate corresponding sequences from other organisms. In this manner, methods such as PCR, hybridization, and the like can be used to identify such sequences based on their sequence homology to the sequences set forth herein. Sequences isolated based on their sequence identity to the entire fumonisin-degrading sequences set forth herein or to fragments thereof are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the fumonisin-degrading sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire fumonisin-degrading sequences disclosed herein, or one or more portions thereof, may be used as a probe capable of specifically hybridizing to corresponding fumonisin-degrading sequences and messenger RNAs. To achieve specific hybridization under a variety of conditions, such probes include sequences that are unique among fumonisin-degrading sequences and are preferably at least about 10 nucleotides in length, and most preferably at least about 20 nucleotides in length. Such probes may be used to amplify corresponding fumonisin-degrading sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl (1984) *Anal. Biochem.* 138:267–284: $T_m=81.5°$ C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode for a fumonisin-degradative protein and hybridize to the fumonisin-degrading sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignments are performed using the default parameters of the above mentioned programs. Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

As indicated, the enzymes and nucleotide sequences encoding such enzymes are involved in the degradation of fumonisin and fumonisin-like compounds. Such enzymes and nucleotide sequences can be utilized alone or in combination to engineer microbes or other organisms to metabolize fumonisin and resist its toxic effects.

Fumonisin is produced in the intercellular spaces (apoplast) of Fusarium-infected maize cells. Thus, the apoplast is the preferred location for esterase and deaminase, flavin amine oxidase and possibly other catabolic enzymes. It is possible that some fumonisin could diffuse or be transported into the maize cells before it is broken down by the apoplastic enzymes and may escape catabolism. Thus, it may be beneficial to express a fumonisin pump and reroute the fumonisin or degradation products in such cells. In this manner, any fumonisin entering the cell will be pumped out and reexposed to catabolic enzymes. Similar toxin pumps exist in other toxin-producing fungi that show resistance to toxins or antibiotics. Such a pump useful in the invention and disclosed herein is a P-glycoprotein homolog.

More complete catabolism of fumonisin in transgenic organisms may be provided by esterase and deaminase enzymes. Exophiala enzymes that can further oxidize fumonisin breakdown-products are not detected extracellularly. Such enzymes in all likelihood exist in the cytoplasm, where adequate cofactors such as $NAD^+$ or NADP are found. The fumonisin-induced metabolite transporter is predicted to provide transport of degradation products into cells where they can be further broken down by other enzymes. In this manner, a permease enzyme may be utilized in a heterologous system to transport either AP1 precursors or fumonisin degradation products into the cytoplasm.

The monooxygenase is expected to result in the oxidation of 2-OP to a compound that lacks a keto group, having instead a terminal aldehyde group, or possibly a carboxylate group. See, for example, Trudgill et al. (1984) in *Microbial Degradation of Organic Compounds,* ed. Gibson (Microbiology Series Vol. 13, Marcel Dekker, New York), Chapter 6; and Davey and Trudgill (1977) *Eur. J. Biochem.* 74:115.

This reaction is due to a type of enzymatic oxidation referred to as Baeyer-Villiger oxidation, in which monooxygen is inserted adjacent to a keto function, resulting in a lactone or ester linkage. The metabolism of trans-cyclohexane-1,2 diol by Acinetobacter provides a model for the activity of a Baeyer-Villiger monooxygenase on 2-OP. This diol is first oxidized to ortho hydroxy cyclohexanone and then a monooxygen is inserted between the quinone and hydroxy functions by the Baeyer-Villiger enzyme, cyclohexanone monooxygenase. This intermediate spontaneously rearranges to a linear aldehyde carboxylic acid. By analogy, for 2-OP it is predicted oxygen is inserted between carbons 2 and 3 followed by spontaneous cleavage to a C22 aldehyde and acetic acid. Further oxidation by an aldehyde dehydrogenase would convert this compound to a carboxylic acid; other catabolic products would also be possible given the high reactivity of the aldehyde group. Additional steps include the use of an aldehyde dehydrogenase to result in the oxidation of the aldehyde product of fumonisin to a hydroxy carboxylic acid.

It is recognized that the DNA sequences of the invention can be inserted into expression cassettes and used to transform a variety of organisms. Enzymes produced recombinantly may be tested for their ability to modify fumonisin or a fumonisin byproduct using labeled starting material and appropriate buffer and cofactor conditions. For example, to test aldehyde dehydrogenase activity, the aldehyde dehydrogenase produced in a recombinant manner would be incubated with cofactors, NAD+ or NADP, and $^{14}$C-labeled 2-OP for various times and then an aliquot of the reaction mix spotted on TLC. Enzyme activity would be indicated by the appearance of a new radiolabeled spot at a different Rf on the TLC plate.

The sequences of the invention can be introduced into any host organism. The sequences to be introduced may be used in expression cassettes for expression in the host of interest where expression in the host is necessary for transcription.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The marker gene confers a selectable phenotype on the transformed cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance; the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

The transcriptional initiation region, the promoter, may be native or analogous or foreign or heterologous to the host as well as to the coding sequence. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a DNA sequence of interest, and a transcriptional and translational termination region functional in the host. The termination region may be native with the transcriptional initiation region, may be native with the DNA sequence of interest, or may be derived from another source. For use in plants or plant cells, convenient termination regions are available from the Ti-plasmid of *A. tumefaciens,* such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 1 7:7891–7903; Joshi et al. (1987) *Nucleic Acids Res.* 15:9627–9639.

Nucleotide sequences of the invention are provided in expression cassettes for expression in the host cell of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al (1987) *Nature* 325:622–625); tobacco mosaic virus leader (TMV) (Gallie et al (1989) in *Molecular Biology of RNA,* ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In the same manner, a plant can be transformed with the nucleotide sequences of the invention to provide complete detoxification of fumonisin in the transformed plant and plant products. Such plants include, for example, species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco, and Populus.

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, nonrecombinant viral infection, nonrecombinant bacterial transformation, nonrecombinant transposition, or spontaneous mutation.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) In vitro *Cell Dev. Biol.* 27P:175–182 (soybean); Singh et al. (1998) *Theor. Appl Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci.* USA 84:5345–5349 (Liliaceae); De Wet et al. (1985) in *The Experimental Manipulation of Ovule Tissues,* ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The degradative enzymes can be fermented in a bacterial host and the resulting bacteria processed and used as a microbial spray. Any suitable microorganism can be used for this purpose. See, for example, Gaertner et al. (1993) in *Advanced Engineered Pesticides,* Kim (Ed.).

The genes of the invention can be introduced into microorganisms that multiply on plants (epiphytes) to deliver enzymes to potential target crops. Epiphytes can be gram-positive or gram-negative bacteria, for example.

The microorganisms that have been genetically altered to contain at least one degradative gene and protein may be used for protecting agricultural crops and products. In one aspect of the invention, whole, i.e., unlysed, cells of the transformed organism are treated with reagents that prolong the activity of the enzyme produced in the cell when the cell is applied to the environment of a target plant. A secretion signal sequence may be used in combination with the gene of interest such that the resulting enzyme is secreted outside the host cell for presentation to the target plant.

Plant signal sequences, including, but not limited to, signal-peptide encoding DNA/RNA sequences which target proteins to the extracellular matrix of the plant cell (Dratewka-Kos et al., (1989) *J. Biol. Chem.* 264:4896–4900), the *Nicotiana plumbaginifolia* extension gene (DeLoose, et al. (1991) *Gene* 99:95–100), signal peptides which target proteins to the vacuole like the sweet potato sporamin gene (Matsuka et al. (1991) *PNAS* 88:834) and the barley lectin gene (Wilkins et al. (1990) *Plant Cell* 2:301–313), signal peptides which cause proteins to be secreted such as that of PRIb (Lind et al. (1992) *Plant Mol. Biol.* 18:47–53), or the barley alpha amylase (BAA) (Rahmatullah et al. (1989) *Plant Mol. Biol.* 12:119) and hereby incorporated by reference, or from the present invention the signal peptide from the ESP1 or BEST1 gene, or signal peptides which target proteins to the plastids such as that of rapeseed enoyl-Acp reductase (Verwaert et al. (1994) *Plant Mol. Biol.* 26:189–202) are useful in the invention.

In this manner, at least one of the genes encoding a degradation enzyme of the invention may be introduced via a suitable vector into a microbial host, and said transformed host applied to the environment or plants or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the polypeptide pesticide, and, desirably, to provide for improved protection of the enzymes of the invention from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Pichia, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pullulans.*

Illustrative prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae; and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Other considerations include ease of formulation and handling, economics, storage stability, and the like.

A number of ways are available for introducing a gene expressing the degradation enzyme into the microorganism host under conditions that allow for stable maintenance and expression of the gene. For example, expression cassettes can be constructed that include the DNA constructs of interest operably linked with the transcriptional and translational regulatory signals for expression of the DNA constructs, and a DNA sequence homologous with a sequence in the host organism, whereby integration will occur, and/or a replication system that is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. supra; Maniatis et al., eds. (1982) *Molecular Cloning: A Laboratory Manual* (Cold Spring Harbor Laboratory, Cold Spring Harbor, N.Y.); Davis et al., eds. (1980) *Advanced Bacterial Genetics* (Cold Spring Harbor Laboratory, Cold Spring Harbor, N.Y.); and the references cited therein.

It is recognized that the construction of a catabolic pathway in a transformed organism is a complicated feat. Therefore, any means for assembling the enzymes of interest into an organism of interest is encompassed. For example, a single nucleotide sequence encoding all of the desired enzymes or multiples thereof may be transformed into the host organism. When microorganisms are to be applied to the environment or to a plant, several microorganisms, each transformed with one, two, three, or more nucleotide sequences of the invention, may be utilized. In this manner, all of the enzymes necessary to bring about detoxification of fumonisin and related products may be presented to the environment or to the plant by applying a mixture of transformed organisms or a single organism capable of expressing the entire pathway or at least expressing enough of the pathway to detoxify fumonisin.

In plants, nucleotide sequences for an enzyme may be transformed into a plant and crossed with plants expressing a different enzyme. In this manner, progeny can be obtained having the entire sequence or enough of the sequence to detoxify fumonisin. Alternatively, a plant can be transformed with nucleotides encoding several enzymes at the same time. In some tissue culture systems it is possible to transform callus with one nucleotide sequence, establish a stable culture line, and then transform the callus a second time with a second nucleotide sequence. The process may be repeated to introduce additional sequences.

To facilitate the expression of more than one enzyme in a cell, e.g. a plant cell, fusion proteins may be created. Generally, a spacer region is included between the proteins. The spacer region may comprise a cleavage site for cleavage by an endogenous or introduced protease.

The present invention also relates to a method of detoxifying a fumonisin or a structurally related mycotoxin with the enzymes from *Exophiala spinifera* (American Type Culture Collection Accession No. 74269), during the processing of grain for animal or human food consumption, during the processing of plant material for silage, or in food crops contaminated with a toxin-producing microbe, such as but not limited to, tomato. Since the atmospheric ammoniation of corn has proven to be an ineffective method of detoxification (see Haumann (1995) *INFORM* 6:248–257), such a methodology during processing is particularly critical where transgenic detoxification is not applicable.

In this embodiment, the fumonisin degradative enzymes found in *Exophiala spinifera* (American Type Culture Collection Accession No. 74269), are presented to grain, plant material for silage, or a contaminated food crop, or during the processing procedure, at the appropriate stages of the procedure and in amounts effective for detoxification of fumonisins and structurally related mycotoxins. Detoxification by this method can occur not only during the processing, but also any time prior to or during the feeding of the grain or plant material to an animal or incorporation of the grain or food crop into a human food product, or before or during ingestion of the food crop. The enzymes or microorganisms can be introduced during processing in appropriate manners, for example, as a wash or spray, or in dried or lyophilized form or powered form, depending upon the nature of the milling process and/or the stage of processing at which the enzymatic treatment is carried out. See generally, Hoseney, R. C. (1990) *Principles of Cereal Science and Technology,* American Assn. of Cereal Chemists, Inc. (especially Chapters 5, 6 and 7); Jones, J. M. (1992) *Food Safety,* Eagan Press, St. Paul, Minn. (especially Chapters 7 and 9); and Jelen, P. (1985) *Introduction to Food Processing,* Restan Publ. Co., Reston, Va. Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase from *Exophiala spinifera* (American Type Culture Collection Accession No. 74269), showed a range of activity from about pH 3 to about pH 6, and the esterase from the bacterium of the American Type Culture Collection Accession No. 55552 showed a range of activity from about pH 6 to about pH 9 (U.S. Pat. No. 5,716,820, supra). The APAO enzyme from *Exophiala spinifera* (American Type Culture Collection Accession No. 74269) has a pH range of activity from pH 6 to pH 9.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides, or mixtures of several of these preparations, if desired, together with further agriculturally acceptable carriers, surfactants, or application-promoting adjuvants customarily employed in the art of formulation. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers.

The enzymes can be introduced during processing in appropriate manners, for example as a wash or spray, or in dried or lyophilized form or powered form, depending upon the nature of the milling process and/or the stage of processing at which the enzymatic treatment is carried out. See generally, Hoseney (1990) *Principles of Cereal Science and Technology* (American Association of Cereal Chemists, Inc.), especially Chapters 5, 6, and 7; Jones (1992) *Food Safety* (Eagan Press, St. Paul, Minn.), especially Chapters 7 and 9; and Jelen (1985) *Introduction to Food Processing* (Restan Publishing Company, Reston, Va.). Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The enzymes from *Exophiala spinifera,* American Type Culture Collection Accession No. 74269, showed a range of activity for esterase from about pH 3 to about pH 7 (U.S. Pat. No. 5,716,820, supra). The APAO enzyme from *Exophiala spinifera,* American Type Culture Collection Accession No. 74269, has a pH range of activity from pH 6 to pH 9.

In another embodiment, ruminal microorganisms can be genetically engineered to contain and express at least one of the fumonisin degradation enzymes of the invention. The genetic engineering of microorganisms is now an art-recognized technique, and ruminal microorganisms so engineered can be added to feed in any art-recognized manner, for example as a probiotic or inoculant. In addition, microorganisms, plants, or other organisms or their cultured cells in vitro capable of functioning as bioreactors can be engineered so as to be capable of mass producing the degradative enzymes of *Exophiala spinifera* (American Type Culture Collection Accession No. 74269).

Another embodiment of the present invention is the use of the enzymes of the present invention as detection reagents for fumonisins and related compounds. The enzymes of the present invention can be used as detection reagents because of the high specificity of the esterase and deaminase enzymes, and the fact that hydrolysis followed by amine oxidation can be monitored by detection of hydrogen peroxide or ammonia using standard reagents (analogous to a glucose detection assay using glucose oxidase). Hydrogen peroxide is often measured by linking a hydrogen peroxide-dependent peroxidase reaction to a colored or otherwise detectable peroxidase product (e.g., Demmano et al. (1996) *European Journal of Biochemistry* 238(3):785–789). Ammonia can be measured using ion-specific electrodes: Fritsche et al. (1991) *Analytica Chimica Acta* 244(2) :179–182; West et al. (1992) *Analytical Chemistry* 64(5) :533–540, and all herein incorporated by reference) or by GC or other chromatographic method.

For example, recombinant or non-recombinant, active fumonisin esterase, APAO, and proteins of the invention are added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to AP1, the AP1 to 2-OP, ammonia, and hydrogen peroxide, and to further degradation products. Then suitable reagents are added for quantification of the hydrogen peroxide or ammonia that were generated stoichiometrically from fumonisins. By comparison with control tubes that received no esterase or APAO enzyme, the amount of fumonisin present can be calculated in direct molar proportion to the hydrogen peroxide or ammonia detected, relative to a standard curve.

This invention can be better understood by reference to the following nonlimiting examples. It will be appreciated by those skilled in the art that other embodiments of the invention may be practiced without departing from the spirit and the scope of the invention as herein disclosed and claimed.

EXPERIMENTAL

EXAMPLE 1

Fungal and Bacterial Isolates

Exophiala isolates from maize were isolated as described in U.S. Pat. No. 5,716,820, U.S. Pat. No. 6,025,188, and U.S. Pat. No. 6,229,071, herein incorporated by reference.

Isolation Methods

Direct isolation of black yeasts from seed was accomplished by plating 100 microliters of seed wash fluid onto YPD or Sabouraud agar augmented with cycloheximide (500 mg/liter) and chloramphenicol (50 mg/liter). Plates were incubated at room temperature for 7–14 days, and individual pigmented colonies that arose were counted and cultured for analysis of fumonisin-degrading ability as described above.

Analysis of Fumonisins and Metabolism Products

Analytical thin-layer chromatography was carried out on 100% silanized $C_{18}$ silica plates (Sigma #T-7020; 10×10 cm; 0.1 mm thick) by a modification of the published method of Rottinghaus (Rottinghaus et al. (1992) *J. Vet. Diagn. Invest.* 4:326, and herein incorporated by reference).

To analyze fumonisin esterase activity, sample lanes were pre-wet with methanol to facilitate sample application. After application of from 0.1 to 2 μl of aqueous sample, the plates were air-dried and developed in MeOH:4% KCl (3:2) or MeOH:0.2 M KOH (3:2) and then sprayed successively with 0.1 M sodium borate (pH 9.5) and fluorescamine (0.4 mg/ml in acetonitrile). Plates were air-dried and viewed under long-wave UV.

For analysis of APAO activity, an alternative method was used. Equal volumes of sample and $^{14}$C-AP1 (1 mg/ml, pH 8) substrate were incubated at room temperature for six days. Analytical thin-layer chromatography was then carried out on C60 HPK silica gel plates (Whatman #4807–700; 10×10 cm; 0.2 mm thick). After application of from 0.1 to 2 μl of aqueous sample, the plates were air dried and developed in $CHCl_3$:MeOH:$CH_3COOH$:$H_2O$ (55:36:8:1). Plates were then air dried and exposed to PhosphorImager screen or autoradiographic film. A Storm PhosphorImager was used to scan the image produced on the screen.

Alkaline Hydrolysis of FB1 to AP1

FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to room temperature and mixed with an equal volume of ethyl acetate, centrifuged at 1000 RCF for 5 minute and the organic (upper) layer recovered. The pooled ethyl acetate layers from two successive extractions were dried under $N_2$ and resuspended in distilled $H_2O$. The resulting material (the aminopentol of FB1 or "AP1") was analyzed by TLC.

Enzyme Activity of Culture Filtrate and Mycelium

*Exophiala spinifera* isolate 2141.10 was grown on YPD agar for 1 week, and conidia were harvested, suspended in sterile water, and used at 105 conidia per ml to inoculate sterile Fries mineral salts medium containing 1 mg/ml purified FB1 (Sigma Chemical Co.). After 2 weeks incubation at 28° C. in the dark, cultures were filtered through 0.45 micron cellulose acetate filters and rinsed with Fries mineral salts. Fungal mycelium was suspended in 15 mL of 0.1% FB1, pH 5.2+1 mM EDTA+3 $\mu$g/mL Pepstatin A+1.5 $\mu$g/mL Leupeptin and disrupted in a Bead Beater™ using 0.1 mm beads and one minute pulses, with ice cooling. Hyphal pieces were collected by filtering through Spin X™ (0.22 $\mu$m), and both mycelial supernatant and original culture filtrates were assayed for fumonisin modification by methods outlined above.

Preparation of Crude Culture Filtrate

Agar cultures grown as above were used to inoculate YPD broth cultures (500 ml) in conical flasks at a final concentration of $10^5$ conidia per ml culture. Cultures were incubated 5 days at 28° C. without agitation and mycelia harvested by filtration through 0.45 micron filters under vacuum. The filtrate was discarded, and the mycelial mat was washed and resuspended in sterile carbon-free, mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4.7H_2O$, pH 4.5) containing 0.5 mg/ml alkaline hydrolyzed crude FB1. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature and resuspended in 50 mM sodium acetate, pH 5.2 containing 10mM $CaCl_2$. The crude culture filtrate (approx. 200-fold concentrated) was stored at −20° C.

To obtain preparative amounts of enzyme-hydrolyzed fumonisin, 10 mg of FB1 (Sigma) was dissolved in 20 mL of 50 mM sodium acetate at pH 5.2+10 mM $CaCl_2$, and 0.25 mL of 200×concentrated crude culture filtrate of 2141.10 was added. The solution was incubated at 37° C. for 14 hours, and then cooled to room temperature. The reaction mixture was brought to approximately pH 9.5 by addition of 0.4 mL of 4 N KOH, and the mixture was extracted twice with 10 mL ethyl acetate. The combined organic layers were dried under $LN_2$ and resuspended in $dH_2O$. 2.5 milligrams of organic extracted material were analyzed by Fast Atom Bombardment (FAB) mass spectrometry. The resulting mass spectrum showed a major ion at M/z (+1)=406 mass units, indicating the major product of enzymatic hydrolysis was AP1, which has a calculated molecular weight of 405.

EXAMPLE 2

Preparation of AP1-induced and Non-induced Mycelium

Liquid cultures of *Exophiala spinifera* isolate 2141.10 were prepared from YPD agar plates (Yeast Extract 10 gm, Bacto-Peptone 20 gm, Dextrose 0.5 gm, Bacto-Agar 15 gm per liter of water). Aliquots (400–500 µL) of a water suspension of *E. spinifera* cells from YPD agar were spread uniformly onto 150×15 mm YPD agar plates with 4 mm sterile glass beads. The plates were incubated at room temperature for 6–7 days. The mycelia/conidia were transferred from the agar plates into Mineral Salts Medium (MSM) ($Na_2HPO_4 \cdot 7H_2O$ 0.2 gm, $NH_4Cl$ 1.0 gm, $CaCl_2 \cdot 2H_2O$ 0.01 gm, $FeSO_4 \cdot 7H_2O$ 0.02 gm per liter of distilled water, pH 4.5) and centrifuged at 5000 × g, 4° C., 20 minutes to pellet the cells. The cell pellet was rinsed once in 40 mL MSM and recentrifuged. The rinsed cell pellet was used to inoculate MSM at a 1:19 ratio of packed cells: MSM. The culture was supplemented with AP1 to a final concentration of 0.5–1.0 mg/ml and incubated at 28° C., 100 rpm, in the dark to induce catabolic enzymes. The supernatants were removed by filtration through 0.45 cellulose acetate. The remaining mycelial mat was washed with sterile MSM and then frozen in liquid nitrogen for storage.

EXAMPLE 3

Effect of FB1 and AP1 on Maize Coleoptiles

Maize coleoptiles from 4 day dark-grown germinated maize seeds were excised above the growing point and placed in 96-well microliter plates in the presence of 60 microliters of sterile distilled water containing FB1 or AP1 at approximately equimolar concentrations of 1.5, 0.5, 0.15, 0.05, 0.015, 0.005, 0.0015, or 0.0005 millimolar, along with water controls. After 2 days in the dark at 28° C. the coleoptiles were placed in the light and incubated another 3 days. Injury or lack thereof was evaluated as follows:

| | 0 | .0005 | .0015 | .005 | .015 | .05 | .15 | .5 | 1.5 | mM |
|---|---|---|---|---|---|---|---|---|---|---|
| FB1 | − | − | − | − | +/− | + | + | + | + | |
| AP1 | − | − | − | − | − | − | − | − | + | |

+ = brown necrotic discoloration of coleoptile
− = no symptoms (same as water control)

The results (see table above) indicate there is at least a 30-fold difference in toxicity between FB1 and AP1 to maize coleoptiles of this genotype. This is in general agreement with other studies where the toxicity of the two compounds was compared for plant tissues. In Lemna tissues, AP1 was approximately 40-fold less toxic (Vesonder et al. (1992) *Arch. Environ. Contam. Toxicol.* 23:464–467 (1992)). Studies with both AAL toxin and FB1 in tomato also indicate the hydrolyzed version of the molecule is much less toxic (Gilchrist et al. (1992) *Mycopathologia* 117: 57–64). Lamprecht et al. also observed an approximate 100-fold reduction in toxicity to tomato by AP1 versus FB1 (Lamprecht et al. (1994) *Phytopathology* 84:383–391).

EXAMPLE 4

Effect of FBI and AP1 on Maize Tissue Cultured Cells

Black Mexican Sweet, BMS

FB1 or AP1 at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar FB1, but no inhibition was observed until 40 micromolar AP1. This represents an approximate 100-fold difference in toxicity to maize tissue-cultured cells. Similarly Van Asch et al. observed significant inhibition of maize callus grown on solid medium at 1.4 micromolar FB1 (Van Asch et al. (1992) *Phytopathology* 82:1330–1332). AP1 was not tested in that study, however.

EXAMPLE 5

The polynucleotides were identified using a proprietary transcript imaging method that compares transcript patterns in two samples and allows cloning of differentially expressed fragments. This technology was developed by CuraGen® (New Haven, Conn.) (see PCT patent application Ser. No. WO 97/1 5690, published May 1, 1997 and claiming priority from U.S. application Ser. No. 08/663,823, which issued as U.S. Pat. No. 5,972,693, all of which are hereby incorporated by reference). Fluorescently-tagged, PCR amplified cDNA fragments representing expressed transcripts can be visualized as bands or peaks on a gel tracing, and the cDNA from differentially expressed (induced or suppressed) bands can be recovered from a duplicate gel, cloned, and sequenced. Known cDNAs can be identified without the need for cloning, by matching the predicted size and partially known sequence of specific bands on the tracing.

Two RNA samples were obtained from cultures of E. spinifera grown for a specified period in a mineral salts medium containing either AP1 (induced condition) or gamma-aminobutyric acid (ABA; non-induced condition) as a sole carbon source. In the induced condition, fumonisin esterase, amine oxidase, enzyme activities are detected, whereas in the non-induced condition these activities are not detected. The methods used for induction of and detection of enzyme activity are described earlier (see Example 2 and Example 5). RNA was extracted from induced mycelium by Tri-Reagent methods (Molecular Research Center Inc., Cincinnati, Ohio) only using frozen tissue samples ground with a mortar and pestle 2-fold and up to 79-fold and greater until slushy and adding an additional extraction after the phase separation by extracting the aqueous phase one time with phenol, and two times with a phenol:chloroform:isoamyl alcohol mixture. The RNAs were submitted for CuraGen® transcript imaging to detect cDNA fragments that are induced specifically in the presence AP1. In the resulting gel tracing several bands were found which showed induction of at least 10-fold in AP1-grown cells as compared to cells grown in ABA. One set of induced fragments can be matched to the fumonisin esterase cDNA. The cloned bands and possible functions are provided in Table 2. Highly induced bands and their likely function are provided in Tables 2 and 3.

TABLE 2

| Clone ID | Best BLAST Hit | BLAST Hit Name, source, size | Prob | from–to | Function |
|---|---|---|---|---|---|
| | | Monooxygenase | | | |
| M1a0-388 | A28550 | cyclohexanone monooxygenase, *Acinetobacter* (flavin monooxygenase or FMO)EC 1.14.13.22 Length = 543 | 1.4e–22 | 339–414 | Baeyer-Villiger oxidation of 2-OP1 (AP1-N1), utilizing molecular oxygen and reduced NADPH Or NADH |
| | | Aldehyde dehydrogenase (EC 1.) | | | |
| k0n0-235 passed | Y09876 | Aldehyde dehydrogenase (*Nicotiana tabacum*); Length = 542 | 1.1e–07 | 152–191 | Oxidation of aldehyde product of FMO to carboxylic acid |
| | | Permease | | | |
| r0v0-239 | S64084 | Choline transport protein, yeast Length = 563 | 9.3e–05 | 337–397 | Transport of 2-OP1 into the cytoplasm |
| r0w0-424 w0h0-268 | S51169 | amino acid transporter AAP4-*Arabidopsis thaliana* len = 466 | 0.98 | 8–76 | Transport of 2-OP1 into the cytoplasm |
| r0w0-205 p0t0-308 (contig) | P53744 | KAPA/DAPA permease, yeast BIO5 Length = 561 | 2.1e–07 | 446–488 | Transport of 2-OP1 into the cytoplasm |
| | | Transmembrane pump (P-glycoprotein homolog) | | | |
| r0g1-420 | S20548 | Leptomycin resistance protein, pmdl, *Schizosaccharomyces pombe*. Length = 1362 | 1.8 e–37 | 1255–1359 or 564–668 | Transmembrane pump that removes FB1 from the cytoplasm as a means of protection against its toxic activity |
| g0s0-142 | | Leptomycin resistance protein, pmdl, *Schizosaccharomyces pombe*. Length = 1362 | | 527–588 | Transmembrane pump that removes FB1 from the cytoplasm as a means of protection against its toxic activity |
| 10c0-129 | | Leptomycin resistance protein, pmdl, *Schizosaccharomyces pombe*. Length = 1362 | | | |
| r0s0-180 | | Leptomycin resistance protein, pmdl, *Schizosaccharomyces pombe*. Length = 1362 | | 959–1009 | Transmembrane pump that removes FB1 from the cytoplasm as a means of protection against its toxic activity |
| r0c0-193 | | Leptomycin resistance protein, pmdl, *Schizosaccharomyces pombe*. Length = 1362 | | 885–945 | Transmembrance pump that removes FB1 from the cytoplasm as a means of protection against its toxic activity |
| r0s0-330 | | Leptomycin resistance protein, pmdl, *Schizosaccharomyces pombe*. Length = 1362 | | 1024–1110 | Transmembrance pump that removes FB1 from the cytoplasm as a means of protection against its toxic activity |
| Loc0-129 | S20548 | Leptomycin resistance protein, pmdl, *Schizosaccharomyces pombe*. Length = 1362 | .0082 | 949–988 | Transmembrance pump that removes FB1 from the cytoplasm as a means of protection against its toxic activity |
| r0h1-262 | | Leptomycin resistance protein, pmdl, *Schizosaccharomyces pombe*. Length = 1362 | | 1135–1218 | Transmembrane pump that removes FB1 from the cytoplasm as a means of protection against its toxic activity |
| i0c0-116 | e219956 | ATP binding cassette multidrug transporter, *Emericella nidulans* Length = 1466 | | 1026–1114 | Transmembrane pump that removes FB1 from the cytoplasm as a means of protection against its toxic activity |

TABLE 3

| Cloned Bands | Homology, Comments | Predicted function | Predicted Product |
|---|---|---|---|
| | | 1. Transmembrane pump (P-glycoprotein homolog) | |
| r0g1-420 g0s0-142 l0c0-129 r0s0-180 r0c0-193 r0s0-330 r0h1-262 i0c0-116 | Homology to Leptomycin resistance protein, Pmd1, *Schizosaccharomyces pombe*, Length = 1362, or other ABC transporter gene family member. { } All 9 bands show homology to members of the ABC transporter superfamily. | FB1 Pump: Transmembrane pump that removes FB1 from the cytoplasm as a means of protection against its toxicity |

TABLE 3-continued

| Cloned Bands | Homology, Comments | Predicted function | Predicted Product |
|---|---|---|---|
| r0v0-239 r0w0-205 p0t0-308.4 r0w0-424? w0h0-268? | Homology to choline transport protein, yeast Length = 563 { }Two bands (r0w0-205 and p0t0-308) contig with each other. | 2-OP permease: Transport of 2-OP and/or AP1 into the cytoplasm | 2. Small Molecule Permease<br>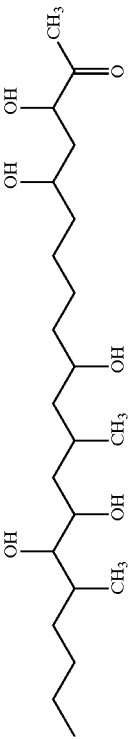<br>AP1 permease activity (proposed) |
| m1a0-388 | Homology to cyclohexanone monooxygenase., Acinetobacter. Oxidation of ketone resulting in carbon-carbon bond breakage to form aldehyde. Utilizes NAD+ or NADP+ | 2-OP monooxygenase: Intracellular oxidation of 2-OP1 to a hydroxy aldehyde (HA-1) plus acetic acid | 3. Flavin Monooxygenase (EC 1.14.13.22)<br>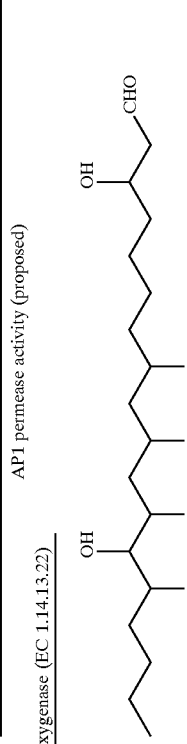 + CH$_3$COO—<br>Hydroxy aldehyde (proposed) |
| k0n0-235 | Homology to aldehyde dehydrogenase (*Nicotiana tabacum*); Length = 542 | HA-1 deydrogenase: Oxidation of aldehyde product of FMO to a hydroxy carboxylic acid (HCA-1) | 4. Aldehyde dehydrogenase<br>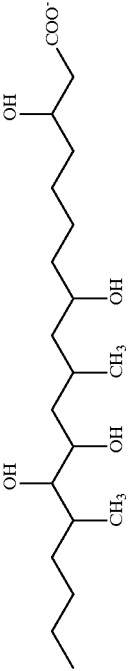<br>Hydroxy-carboxylic acid (proposed) |

Using sequence derived from each clone, a partial cDNA was obtained by 3' and 5' RACE-PCR (Chenchik et al. (1995) *CLONTECHniques X* 1:5–8); Chenchik et al. (1996) in *A Laboratory Guide to RNA: Isolation, Analysis, and Synthesis,* ed. Krieg (Wiley-Liss, Inc.), pp. 273–321. A RACE cloning kit from CLONTECH was used to obtain the RACE amplicons. Briefly, poly A+ RNA is transcribed to make first strand cDNA using a "lock-docking" poly T, cDNA synthesis primer, the second strand is synthesized, and the Marathon cDNA adaptor is ligated to both ends of the ds cDNA. Diluted template is then used with the Marathon adapter primer and in separate reactions either a 5' Gene Specific Primer (GSP) or a 3'GSP is used to produce the 3' or 5' RACE amplicon. After characterization of the RACE product(s) and sequencing, full-length cDNAs may be generated by 1) end-to-end PCR using distal 5' and 3' GSPs with the adapter-ligated ds cDNA as template, or 2) the cloned 5' and 3'-RACE fragments may be digested with a restriction enzyme that cuts uniquely in the region of overlap, and the fragments isolated and ligated. Subsequently, the RACE-generated full-length cDNAs from 1) and 2) may be cloned into a suitable vector.

EXAMPLE 6

Pichia Expression of Degradative Enzymes

For cloning into *Pichia pastoris* expression vector, pPicZalphaA, oligonucleotide primers were designed that contain a 22 bp overlap of the 5' end (sense strand) and 3' end (antisense strand), respectively of the open reading frame of the degradative nucleotide of interest, including the stop codon. In addition, each oligo has a 5' extension with digestible restriction sites that allows cloning of the amplified insert in-frame both into EcoRI/NotI digested pPicZalphaA. pPicZalphaA is an *E. coli* compatible Pichia expression vector containing a functional yeast alpha-factor secretion signal and peptide processing sites, allowing high efficiency, inducible secretion into the culture medium of Pichia. After the generation of the 5' and 3' RACE products, the resulting band was cloned into EcoRI/NotI digested pPicZalphaA plasmid.

Pichia can be transformed as described in Invitrogen Manual, Easy Select™ Pichia Expression Kit, Version B, #161219, with the enzyme polynucleotide of interest with either an intron (negative control, no expression) or without an intron (capable of making an active protein). The Pichia culture fluids and pellets are assayed for enzyme activity as described earlier. The six day culture fluids from the same cultures are used to spike with crude fungal enzyme for positive controls.

The sample 50 μl cell pellets are resuspended in 150 μl cold 50 mM Na-phosphate, pH8.0 and divided into two fresh 500 μL tubes. One tube is kept on ice with no treatment, the pellet suspension, and one tube is used for lysis. An equal volume of 0.1 mm zirconia-silica beads is added to each tube. The tubes are BeadBeat™ for 15 seconds then cooled on ice 5 minutes. This is repeated three times. The crude lysate is then transferred to another tube for assay or lysate suspension.

The TLC assays are performed as follows:
1) pellet suspensions ("PELL"); 10 uL
2) lysate suspensions ("LYS"); 10 uL
3) media controls-mixed 5 uL media with 5 uL crude fungal enzyme (if available); 10 uL
4) positive control-used crude fungal enzyme undiluted; 10 uL
5) substrate control-used 50mM Na-phosphate, pH8.0; 10 uL cofactor (if required) is added to each reaction mixture
incubate 10 uL each sample+10 uL $^{14}$C-substrate (fumonisin, metabolite, or other potential substrate) (1 mg/mL, pH8) at room temperature for 6 days
spot 1.0 uL onto C18 and C60 TLC plates
develop C18 plates in MeOH:4% KCl (3:2)
develop C60 plates in $CHCl_3$:MeOH:$CH_3COOH$:$H_2O$ (55:36:8:1)
air-dry plates
expose plates to PhosphorScreen 2–3 days
use Storm PhosphorImager (Molecular Dynamics) to develop images

EXAMPLE 7

Expression of Degradative Enzymes in *E. coli*

A vector for expressing the enzymes in *E. coli* is a prokaryotic glutathione S-transferase (GST) fusion vector for inducible, high-level intracellular expression of genes or gene fragments as fusions with *Schistosoma japonicum* GST. GST gene fusion vectors include the following features: a lac promoter for inducible, high-level expression; an internal lac Iq gene for use in any *E. coli* host; and the thrombin factor Xa or PreScission Protease recognition sites for cleaving the desired protein from the fusion product. The insert of interest is cloned into the 5' EcoRI site and a 3' NotI site allowing in-frame expression of the fusion peptide. The generation of such an insert is described in the previous example.

*E. coli* is transformed with the vector containing the coding sequence for the degradative enzyme as described in BRL catalogue, Life Technologies, Inc., catalogue; Hanahan (1983) *J. Mol. Biol.* 166:557; Jessee et al. (1984) *J. Focus* 6:4; King et al. (1986) *Focus* 8:1, and hereby incorporated by reference. The transformed *E. coil* is induced by addition of IPTG (isopropyl b-D-thiogalactopyranoside). Samples of soluble extract and Samples of insoluble inclusion bodies are tested for enzyme activity as described in Example 7.

EXAMPLE 8

Transformation and Regeneration of Transgenic Plants

Figure 2:
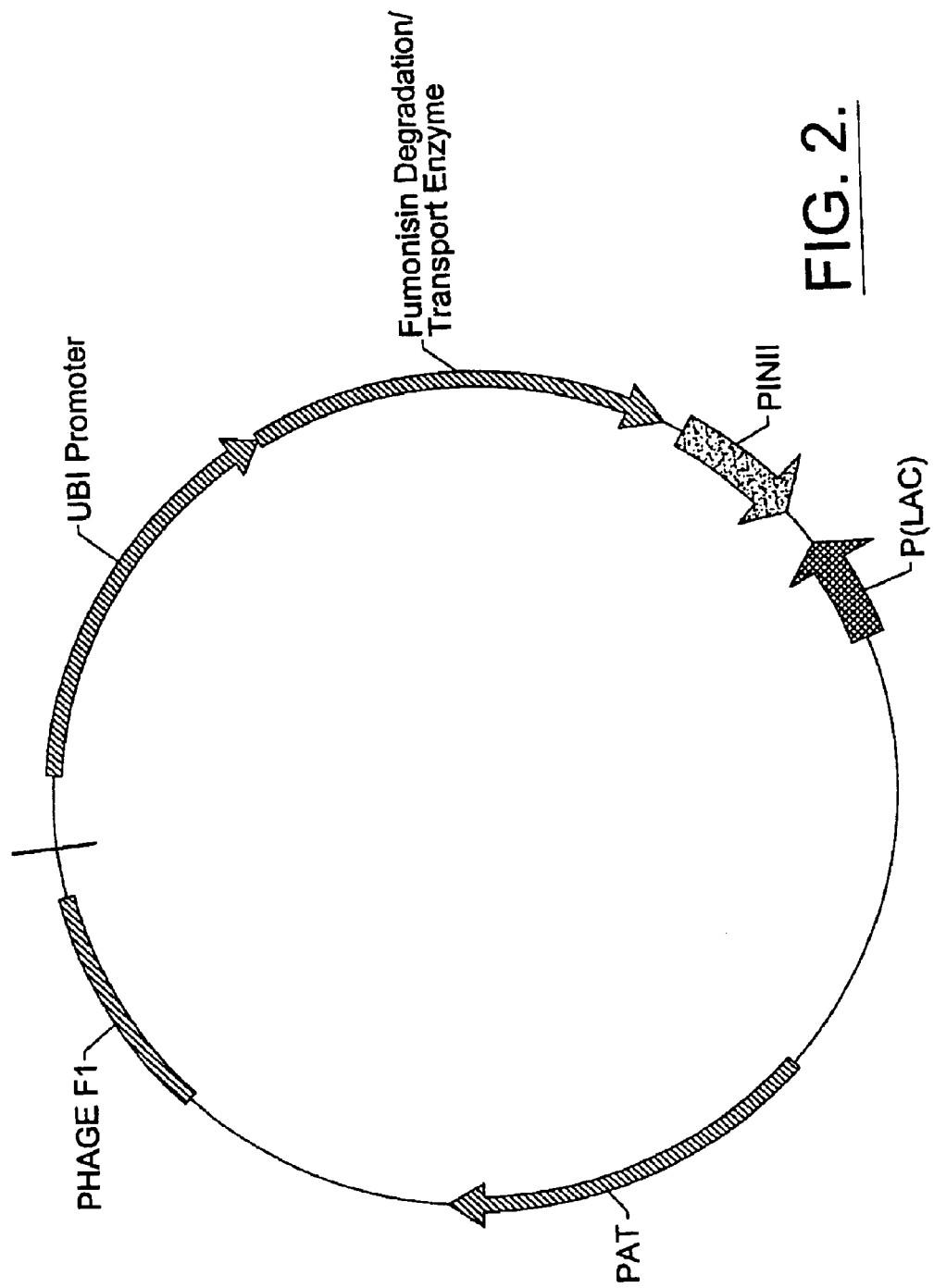
FIG. 2 schematically illustrates a plasmid vector comprising the gene for one of the fumonisin degradative enzymes of the invention operably linked to the ubiquitin promoter.

Immature maize embryos from greenhouse donor plants are bombarded with a plasmid containing the fumonisin-degradation/transporter enzyme nucleotide sequences operably linked to a ubiquitin promoter (FIG. 2). This plasmid also contains the selectable marker gene PAT (Wohlleben et al. (1988) *Gene* 70:25–37) that confers resistance to the herbicide Bialaphos. The preferred construct for expression in maize is the nucleotide sequence of the degradative enzyme either fused to the barley alpha amylase signal sequence or organellar targeting sequence, or left intact for expression in the cytoplasm. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the fumonisin-degradation/transporter enzyme operably linked to the ubiquitin promoter is made. This plasmid DNA also contains a PAT selectable marker. The plasmid is precipitated onto 1.1 μm (average diameter) tungsten pellets using a CaCl₂ precipitation procedure as follows:

- 100 μl prepared tungsten particles in water
- 10 μl (1 μg) DNA in TrisEDTA buffer (1 μg total)
- 100 μl 2.5 M CaCl₂
- 10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34–1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for the expression of a fumonisin-degrading/transporter protein.

APPENDIX

272 V

| Ingredient | Amount | Unit |
| --- | --- | --- |
| D-I H₂O | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:
@ = Add after bringing up to volume
Dissolve ingredients in polished D-I H₂O in sequence
Adjust to pH 5.6
Bring up to volume with polished D-I H₂O after adjusting pH
Sterilize and cool to 60° C.
## = Dissolve 0.100 g of Nicotinic Acid; 0.020 g of Thiamine.HCL; 0.100 g of Pyridoxine.HCL; and 0.400 g of Glycine in 875.00 ml of polished D-I H₂O in sequence. Bring up to volume with polished D-I H₂O. Make in 400 ml portions. Thiamine.HCL & Pyridoxine.HCL are in Dark Desiccator. Store for one month, unless contamination or precipitation occurs, then make fresh stock.
Total Volume (L) = 1.00

APPENDIX-continued

288 J

| Ingredient | Amount | Unit |
| --- | --- | --- |
| D-I H₂O | 950.000 | Ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions:
@ = Add after bringing up to volume
Dissolve ingredients in polished D-I H₂O in sequence
Adjust to pH 5.6
Bring up to volume with polished D-I H₂O after adjusting pH
Sterilize and cool to 60° C.
Add 3.5 g/L of Gelrite for cell biology.
## = Dissolve 0.100 g of Nicotinic Acid; 0.020 g of Thiamine.HCL; 0.100 g of Pyridoxine.HCL; and 0.400 g of Glycine in 875.00 ml of polished D-I H₂O in sequence.
Bring up to volume with polished D-I H₂O. Make in 400 ml portions. Thiamine.HCL & Pyridoxine.HCL are in Dark Desiccator.
Store for one month, unless contamination or
precipitation occurs, then make fresh stock.
Total Volume (L) = 1.00

560 R

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@ = Add after bringing up to volume
# = Add after sterilizing and cooling to temp.
Dissolve ingredients in D-I H₂O in sequence
Adjust to pH 5.8 with KOH
Bring up to volume with D-I H₂O
Sterilize and cool to room temp.
Total Volume (L) = 1.00

560 Y

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
# = Add after sterilizing and cooling to temp.
Dissolve ingredients in D-I H₂O in sequence
Adjust to pH 5.8 with KOH
Bring up to volume with D-I H₂O
Sterilize and cool to room temp.
 Autoclave less time because of increased sucrose
Total Volume (L) = 1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of reducing pathogenicity to a plant of a fungus that produces fumonisin, comprising:

a) stably integrating into the genome of a plant cell a first nucleotide sequence operably linked to a promoter active in said plant cell, wherein said first nucleotide sequence has at least 95% sequence identity to the sequence set forth in SEQ ID NO: 16, 18, 20, 22, 24, 26, 28, 30, or 32 and encodes a polypeptide having amine oxidase activity;

b) optionally stably integrating into the genome of said plant cell a second nucleotide sequence operably linked to a promoter active in said plant cell, wherein said second nucleotide sequence has at least 95% sequence identity to the sequence set forth in SEQ ID NO: 12 or 14 and encodes a polypeptide having fumonisin esterase activity;

c) stably integrating into the genome of said plant cell a nucleotide sequence operably linked to a promoter active in said plant cell, wherein said nucleotide sequence has at least 95% sequence identity to the sequence set forth in SEQ ID NO: 2, 4, 7, or 10, and encodes a polypeptide having fumonisin detoxification activity; and d) regenerating a transformed plant from said plant cell, whereby the pathogenicity of said fungus to said transformed plant is reduced in comparison to the pathogenicity of said fungus to a plant that has not been transformed.

2. The method of claim 1, wherein said second nucleotide sequence comprises the sequence set forth in SEQ ID NO: 12 or 14.

3. The method of claim 1, wherein the nucleotide sequence of step (c) comprises the sequence set forth in SEQ ID NO: 2, 4, 7, or 10.

4. The method of claim 1, wherein said first nucleotide sequence comprises the sequence set forth in SEQ ID NO: 16, 18, 20, 22, 24, 26, 28, 30, or 32.

5. The method of claim 1, wherein said plant cell is a cell from a monocot.

6. The method of claim 5, wherein said monocot is maize.

7. The method of claim 1, wherein said plant cell is a cell from a dicot.

8. The method of claim 1, wherein the promoter of step (a) is an inducible promoter.

9. The method of claim 1, wherein the promoter of step (a) is a tissue-preferred promoter.

10. A plant having stably integrated into its genome:
 a) a first nucleotide sequence operably linked to a promoter active in said plant, wherein said first nucleotide sequence has at least 95% sequence identity to the sequence set forth in SEQ ID NO: 16, 18, 20, 22, 24, 26, 28, 30, or 32 and encodes a polypeptide having amine oxidase activity;
 b) optionally, a second nucleotide sequence operably linked to a promoter active in said plant, wherein said second nucleotide sequence has at least 95% sequence identity to the sequence set forth in SEQ ID NO: 12 or 14 and encodes a polypeptide having fumonisin esterase activity; and,
 c) a nucleotide sequence operably linked to a promoter active in said plant, wherein said nucleotide sequence has at least 95% identity to the sequence set forth in SEQ ID NO: 2, 4, 7, or 10, and encodes a polypeptide having fumonisin detoxification activity.

11. The plant of claim 10, wherein said second nucleotide sequence is set forth in SEQ ID NO: 12 or 14.

12. The plant of claim 10, wherein said first nucleotide sequence encodes a polypeptide having the sequence set forth in SEQ ID NO: 17, 19, 21, 23, 25, 27, 29, 31, or 33.

13. The plant of claim 10, wherein said first nucleotide sequence comprises the sequence set forth in SEQ ID NO: 16, 18, 20, 22, 24, 26, 28, 30, or 32.

14. The plant of claim 10, wherein said plant is a monocot.

15. The plant of claim 14, wherein said monocot is maize.

16. The plant of claim 10, wherein said plant is a dicot.

17. Transformed seed of the plant of claim 10.

18. A plant cell having stably integrated into its genome:
 a) a first nucleotide sequence operably linked to a promoter active in said plant cell, wherein said first nucleotide sequence has at least 95% sequence identity to the sequence set forth in SEQ ID NO: 16, 18, 20, 22, 24, 26, 28, 30, or 32 and encodes a polypeptide having amine oxidase activity;
 b) optionally, a second nucleotide sequence operably linked to a promoter active in said plant cell, wherein said second nucleotide sequence has at least 95% sequence identity to the sequence set forth in SEQ ID NO: 12 or 14 and encodes a polypeptide having fumonisin esterase activity; and,
 c) a nucleotide sequence operably linked to a promoter active in said plant cell, wherein said nucleotide sequence has at least 95% identity to the sequence set forth in SEQ ID NO: 2, 4, 7, or 10 and encodes a polypeptide having fumonisin detoxification activity.

19. A method of reducing pathogenicity to a plant of a fungus that produces fumonisin, comprising stably integrating into the genome of a plant cell:
 a) a first nucleotide sequence operably linked to a promoter active in said plant cell, wherein said first nucleotide sequence encodes a polypeptide having at least 95% sequence identity to the sequence set forth in SEQ ID NO: 17, 19, 21, 23, 25, 27, 29, 31, or 33 and having amine oxidase activity;
 b) optionally, a second nucleotide sequence operably linked to a promoter active in said plant cell, wherein said second nucleotide sequence encodes a polypeptide having at least 95% sequence identity to the sequence set forth in SEQ ID NO: 13 or 15 and having fumonisin esterase activity;
 c) a nucleotide sequence operably linked to a promoter active in said plant cell, wherein said nucleotide sequence encodes a polypeptide having at least 95% sequence identity to the sequence set forth in SEQ ID NO: 3, 5, 8, or 11, and having fumonisin detoxification activity; and
 d) regenerating a transformed plant from said plant cell, whereby the pathogenicity of said fungus to said transformed plant is reduced in comparison to the pathogenicity of said fungus to a plant that has not been transformed.

20. A plant having stably integrated into its genome
 a) a first nucleotide sequence operably linked to a promoter active in a plant cell, wherein said first nucleotide sequence encodes a polypeptide having at least 95% sequence identity to the sequence set forth in SEQ ID NO: 17, 19, 21, 23, 25, 27, 29, 31, or 33 and having amine oxidase activity
 b) optionally, a second nucleotide sequence operably linked to a promoter active in a plant cell, wherein said second nucleotide sequence encodes a polypeptide having at least 95% sequence identity to the sequence set forth in SEQ ID NO: 13 or 15 and having fumonisin esterase activity; and,
 c) a nucleotide sequence operably linked to a promoter active in a plant cell, wherein said nucleotide sequence encodes a polypeptide having at least 95% sequence identity to the sequence set forth in SEQ ID NO: 3, 5, 8, or 11 and having fumonisin detoxification activity.

21. The method of claim 1, wherein the nucleotide sequence of step (c) has at least 98% identity to the sequence set forth in SEQ ID NO: 2, 4, 7, or 10.

22. The method of claim 1, wherein the nucleotide sequence of step (c) encodes the polypeptide set forth in SEQ ID NO: 3, 5, 8, or 11.

23. The plant cell of claim 18, wherein said first nucleotide sequence is set forth in SEQ ID NO: 16, 18, 20, 22, 24, 26, 28, 30, or 32.

24. The plant of claim 10, wherein the nucleotide sequence of step (c) encodes the polypeptide set forth in SEQ ID NO: 3, 5, 8, or 11.

25. The plant of claim 10, wherein the nucleotide sequence of step (c) is the sequence set forth in SEQ ID NO: 2, 4, 7, or 10.

26. The plant cell of claim 18, wherein said first nucleotide sequence has at least 98% sequence identity to the sequence set forth in SEQ ID NO: 16, 18, 20, 22, 24, 26, 28, 30, or 32, said second nucleotide sequence has at least 98% sequence identity to the sequence set forth in SEQ ID NO: 12 or 14, and the nucleotide sequence of step (c) has at least 98% identity to the sequence set forth in SEQ ID NO: 2, 4, 7, or 10.

27. The plant cell of claim 18, wherein the nucleotide sequence of step (c) encodes the polypeptide set forth in SEQ ID NO: 3, 5, 8, or 11.

28. The plant cell of claim 18, wherein said first nucleotide sequence encodes a polypeptide having at least 95% sequence identity to the sequence set forth in SEQ ID NO: 17, 19, 21, 23, 25, 27, 29, 31, or 33, said second nucleotide sequence encodes a polypeptide having at least 95% sequence identity to the sequence set forth in SEQ ID NO: 13 or 15, and the nucleotide sequence of step (c) encodes a polypeptide having at least 95% sequence identity to the sequence set forth in SEQ ID NO: 3, 5, 8, or 11.

29. The method of claim 1, wherein said first nucleotide sequence encodes a polypeptide having the sequence set forth in SEQ ID NO: 17, 19, 21, 23, 25, 27, 29, 31, or 33, said second nucleotide sequence encodes a polypeptide having the sequence set forth in SEQ ID NO: 13 or 15, and the nucleotide sequence of step (c) encodes a polypeptide having the sequence set forth in SEQ ID NO: 3, 5, 8, or 11.

30. The plant cell of claim 18, wherein said first nucleotide sequence encodes a polypeptide comprising the sequence set forth in SEQ ID NO: 17, 19, 21, 23, 25, 27, 29, 31, or 33, said second nucleotide sequence encodes a polypeptide comprising the sequence set forth in SEQ ID NO: 13 or 15, and the nucleotide sequence of step (c) encodes a polypeptide comprising the sequence set forth in SEQ ID NO: 3, 5, 8, or 11.

31. The plant cell of claim 18, wherein the nucleotide sequence of step (c) is set forth in SEQ ID NO: 2,4, 7, or 10.

32. The plant of claim 10, wherein said first nucleotide sequence encodes a polypeptide comprising the sequence set forth in SEQ ID NO: 17, 19, 21, 23, 25, 27, 29, 31, or 33, said second nucleotide sequence encodes a polypeptide comprising the sequence set forth in SEQ ID NO: 13 or 15, and the nucleotide sequence of step (c) encodes a polypeptide comprising the sequence set forth in SEQ ID NO: 3, 5, 8, or 11.

33. The plant cell of claim 18, wherein said second nucleotide sequence is set forth in SEQ ID NO: 12 or 14.

* * * * *

SEQUENCE LISTING

<160> NUMBER OF SEQ ID NOS: 33

<210> SEQ ID NO 1
<211> LENGTH: 1691
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: flavin monooxygenase with intron

<400> SEQUENCE: 1

```
atgtcggcca ccagcaactc cagaggcgat tgttccgtcg catgcgacgc catcatcgtt      60
ggagccggcc tcagcggcat ctctgctgtg tacaaattgc gaaagctcag actcaacgcc     120
aaaatcttcg agggagcccc cgattttggc ggcgtctggc actggaaccg ctaccctggc     180
gctcgtgttg attcggagac gcccttctac caactgaaca ttcccgaagt atggaaagac     240
tggacctggt cttgccgcta tcctgaccag aaagagttgc tgtcatatgt tcaccactgt     300
gacaagatcc ggggcttgag aaaagacgtc tacttcggag ctgaggtggt tgatgcgcgg     360
tatgccagag atctgggcac ctggactgtc aagacgtcgg ctggccatgt tgcgacggca     420
aagtatctca ttctcgctac ggggttgctc cacaggaagc acactcccgc actccccggc     480
ctcgccgatt caacgggaa ggtgattcat tcgagtgcct ggcacgaaga cttcgacgca     540
gagggccaga gagtcgccgt catcggtgcc ggggccacaa gcatccagat tgttcaggag     600
ttggccaaga aggctgacca ggtaaccatg tttatgcgaa ggccgagcta ttgtctgccc     660
atgcggcaac gaacgatgga taggaacgaa cagacagcct ggaaggccta ctacccccacg     720
ctgtttgaag cgagtcgaaa gtctcggatt ggattcccgg tccaggcacc gtcggttggc     780
atctttgaag tcagccccga gcagcgggag gcctatttcg aagagttgtg ggagcgtggg     840
gcctttaatt ttcttgcttg ccagtaccga gaagtcatgg ttgacaaaaa ggccaaccga     900
ctggtctatg acttctgggc caaaaagact cgatctcgta tcgtcaatcc ggcaaagaga     960
gatctcatgg ctcctctgga gccgccgtac tggttcggta ccaagcgctc cccactggag    1020
agcgactact acgaaatgct ggacaagccg agcgtcgaaa ttgtgaatct agaacaatcg    1080
cccattgtgg ctgttacaaa gacaggtgtg ctcttgagtg acggcagcaa gagggaatgc    1140
gacacgatcg tgctggcgac gggtttcgac agtttcactg gctcgtgagt gtgctcgatc    1200
atgctccga gtccggacgt ttggctgacc ttgaaagatt gacacatatg ggcttgaaaa    1260
acaagcacgg agtggacctg aaggaggtgt ggaaagatgg catatctact tatatgggag    1320
tcttctctca tggcttcccc aatgccttct tcgtcgccac ggctcaagcc ccgaccgtcc    1380
tttccaacgg cccaacgatc atagaaaccc aagtcgactt gatcgccgat acaattgcaa    1440
agttggaggc cgagcacgcc acgtccgttg aggcgacgaa atcagcacaa gaggcatggt    1500
cgattatgat tgccaagatg aacgagcaca ctctgttccc cttgacggat tcgtggtgga    1560
ctggaggcaa catccctggg aaagcaacac gtgctttaac cttcataggc gggattgctc    1620
```

-continued

```
tctatgagca gatctgtcaa gagaaggtgg ccaattggga tgggtttgat gtgcttcatg    1680
ctccctgcta a                                                         1691

<210> SEQ ID NO 2
<211> LENGTH: 1638
<212> TYPE: DNA
<213> ORGANISM: Exophiala spinifera
<220> FEATURE:
<221> NAME/KEY: CDS
<222> LOCATION: (1)...(1638)
<220> FEATURE:
<221> NAME/KEY: misc_feature
<222> LOCATION: (0)...(0)
<223> OTHER INFORMATION: flavin monooxygenase, fully spliced

<400> SEQUENCE: 2 atg tcg gcc acc agc aac tcc aga ggc gat tgt tcc gtc gca tgc gac      48
Met Ser Ala Thr Ser Asn Ser Arg Gly Asp Cys Ser Val Ala Cys Asp
 1               5                  10                  15 gcc atc atc gtt gga gcc ggc ctc agc ggc atc tct gct gtg tac aaa      96
Ala Ile Ile Val Gly Ala Gly Leu Ser Gly Ile Ser Ala Val Tyr Lys
             20                  25                  30 ttg cga aag ctc aga ctc aac gcc aaa atc ttc gag gga gcc ccc gat     144
Leu Arg Lys Leu Arg Leu Asn Ala Lys Ile Phe Glu Gly Ala Pro Asp
         35                  40                  45 ttt ggc ggc gtc tgg cac tgg aac cgc tac cct ggc gct cgt gtt gat     192
Phe Gly Gly Val Trp His Trp Asn Arg Tyr Pro Gly Ala Arg Val Asp
     50                  55                  60 tcg gag acg ccc ttc tac caa ctg aac att ccc gaa gta tgg aaa gac     240
Ser Glu Thr Pro Phe Tyr Gln Leu Asn Ile Pro Glu Val Trp Lys Asp
 65                  70                  75                  80 tgg acc tgg tct tgc cgc tat cct gac cag aaa gag ttg ctg tca tat     288
Trp Thr Trp Ser Cys Arg Tyr Pro Asp Gln Lys Glu Leu Leu Ser Tyr
                 85                  90                  95 gtt cac cac tgt gac aag atc cgg ggc ttg aga aaa gac gtc tac ttc     336
Val His His Cys Asp Lys Ile Arg Gly Leu Arg Lys Asp Val Tyr Phe
            100                 105                 110 gga gct gag gtg gtt gat gcg cgg tat gcc aga gat ctg ggc acc tgg     384
Gly Ala Glu Val Val Asp Ala Arg Tyr Ala Arg Asp Leu Gly Thr Trp
        115                 120                 125 act gtc aag acg tcg gct ggc cat gtt gcg acg gca aag tat ctc att     432
Thr Val Lys Thr Ser Ala Gly His Val Ala Thr Ala Lys Tyr Leu Ile
    130                 135                 140 ctc gct acg ggg ttg ctc cac agg aag cac act ccc gca ctc ccc ggc     480
Leu Ala Thr Gly Leu Leu His Arg Lys His Thr Pro Ala Leu Pro Gly
145                 150                 155                 160 ctc gcc gat ttc aac ggg aag gtg att cat tcg agt gcc tgg cac gaa     528
Leu Ala Asp Phe Asn Gly Lys Val Ile His Ser Ser Ala Trp His Glu
                165                 170                 175 gac ttc gac gca gag ggc cag aga gtc gcc gtc atc ggt gcc ggg gcc     576
Asp Phe Asp Ala Glu Gly Gln Arg Val Ala Val Ile Gly Ala Gly Ala
            180                 185                 190 aca agc atc cag att gtt cag gag ttg gcc aag aag gct gac cag gta     624
Thr Ser Ile Gln Ile Val Gln Glu Leu Ala Lys Lys Ala Asp Gln Val
        195                 200                 205 acc atg ttt atg cga agg ccg agc tat tgt ctg ccc atg cgg caa cga     672
Thr Met Phe Met Arg Arg Pro Ser Tyr Cys Leu Pro Met Arg Gln Arg
    210                 215                 220 acg atg gat agg aac gaa cag aca gcc tgg aag gcc tac tac ccc acg     720
Thr Met Asp Arg Asn Glu Gln Thr Ala Trp Lys Ala Tyr Tyr Pro Thr
225                 230                 235                 240
```

-continued

| | |
|---|---|
| ctg ttt gaa gcg agt cga aag tct cgg att gga ttc ccg gtc cag gca<br>Leu Phe Glu Ala Ser Arg Lys Ser Arg Ile Gly Phe Pro Val Gln Ala<br>　　　　　245　　　　　　　　　250　　　　　　　　　255 | 768 |
| ccg tcg gtt ggc atc ttt gaa gtc agc ccc gag cag cgg gag gcc tat<br>Pro Ser Val Gly Ile Phe Glu Val Ser Pro Glu Gln Arg Glu Ala Tyr<br>260　　　　　　　　　265　　　　　　　　　270 | 816 |
| ttc gaa gag ttg tgg gag cgt ggg gcc ttt aat ttt ctt gct tgc cag<br>Phe Glu Glu Leu Trp Glu Arg Gly Ala Phe Asn Phe Leu Ala Cys Gln<br>　　　275　　　　　　　　　280　　　　　　　　　285 | 864 |
| tac cga gaa gtc atg gtt gac aaa aag gcc aac cga ctg gtc tat gac<br>Tyr Arg Glu Val Met Val Asp Lys Lys Ala Asn Arg Leu Val Tyr Asp<br>290　　　　　　　　　295　　　　　　　　　300 | 912 |
| ttc tgg gcc aaa aag act cga tct cgt atc gtc aat ccg gca aag aga<br>Phe Trp Ala Lys Lys Thr Arg Ser Arg Ile Val Asn Pro Ala Lys Arg<br>305　　　　　　　　　310　　　　　　　　　315　　　　　　　　　320 | 960 |
| gat ctc atg gct cct ctg gag ccg ccg tac tgg ttc ggt acc aag cgc<br>Asp Leu Met Ala Pro Leu Glu Pro Pro Tyr Trp Phe Gly Thr Lys Arg<br>　　　　　325　　　　　　　　　330　　　　　　　　　335 | 1008 |
| tcc cca ctg gag agc gac tac tac gaa atg ctg gac aag ccg agc gtc<br>Ser Pro Leu Glu Ser Asp Tyr Tyr Glu Met Leu Asp Lys Pro Ser Val<br>　　　340　　　　　　　　　345　　　　　　　　　350 | 1056 |
| gaa att gtg aat cta gaa caa tcg ccc att gtg gct gtt aca aag aca<br>Glu Ile Val Asn Leu Glu Gln Ser Pro Ile Val Ala Val Thr Lys Thr<br>355　　　　　　　　　360　　　　　　　　　365 | 1104 |
| ggt gtg ctc ttg agt gac ggc agc aag agg gaa tgc gac acg atc gtg<br>Gly Val Leu Leu Ser Asp Gly Ser Lys Arg Glu Cys Asp Thr Ile Val<br>370　　　　　　　　　375　　　　　　　　　380 | 1152 |
| ctg gcg acg ggt ttc gac agt ttc act ggc tca ttg aca cat atg ggc<br>Leu Ala Thr Gly Phe Asp Ser Phe Thr Gly Ser Leu Thr His Met Gly<br>385　　　　　　　　　390　　　　　　　　　395　　　　　　　　　400 | 1200 |
| ttg aaa aac aag cac gga gtg gac ctg aag gag gtg tgg aaa gat ggc<br>Leu Lys Asn Lys His Gly Val Asp Leu Lys Glu Val Trp Lys Asp Gly<br>　　　　　405　　　　　　　　　410　　　　　　　　　415 | 1248 |
| ata tct act tat atg gga gtc ttc tct cat ggc ttc ccc aat gcc ttc<br>Ile Ser Thr Tyr Met Gly Val Phe Ser His Gly Phe Pro Asn Ala Phe<br>　　　420　　　　　　　　　425　　　　　　　　　430 | 1296 |
| ttc gtc gcc acg gct caa gcc ccg acc gtc ctt tcc aac ggc cca acg<br>Phe Val Ala Thr Ala Gln Ala Pro Thr Val Leu Ser Asn Gly Pro Thr<br>435　　　　　　　　　440　　　　　　　　　445 | 1344 |
| atc ata gaa acc caa gtc gac ttg atc gcc gat aca att gca aag ttg<br>Ile Ile Glu Thr Gln Val Asp Leu Ile Ala Asp Thr Ile Ala Lys Leu<br>450　　　　　　　　　455　　　　　　　　　460 | 1392 |
| gag gcc gag cac gcc acg tcc gtt gag gcg acg aaa tca gca caa gag<br>Glu Ala Glu His Ala Thr Ser Val Glu Ala Thr Lys Ser Ala Gln Glu<br>465　　　　　　　　　470　　　　　　　　　475　　　　　　　　　480 | 1440 |
| gca tgg tcg att atg att gcc aag atg aac gag cac act ctg ttc ccc<br>Ala Trp Ser Ile Met Ile Ala Lys Met Asn Glu His Thr Leu Phe Pro<br>　　　　　485　　　　　　　　　490　　　　　　　　　495 | 1488 |
| ttg acg gat tcg tgg tgg act gga ggc aac atc cct ggg aaa gca aca<br>Leu Thr Asp Ser Trp Trp Thr Gly Gly Asn Ile Pro Gly Lys Ala Thr<br>　　　500　　　　　　　　　505　　　　　　　　　510 | 1536 |
| cgt gct tta acc ttc ata ggc ggg att gct ctc tat gag cag atc tgt<br>Arg Ala Leu Thr Phe Ile Gly Gly Ile Ala Leu Tyr Glu Gln Ile Cys<br>515　　　　　　　　　520　　　　　　　　　525 | 1584 |
| caa gag aag gtg gcc aat tgg gat ggg ttt gat gtg ctt cat gct ccc<br>Gln Glu Lys Val Ala Asn Trp Asp Gly Phe Asp Val Leu His Ala Pro<br>530　　　　　　　　　535　　　　　　　　　540 | 1632 |
| tgc taa<br>Cys * | 1638 |

-continued

545

<210> SEQ ID NO 3
<211> LENGTH: 545
<212> TYPE: PRT
<213> ORGANISM: Exophiala spinifera

<400> SEQUENCE: 3

```
Met Ser Ala Thr Ser Asn Ser Arg Gly Asp Cys Ser Val Ala Cys Asp
  1               5                  10                  15

Ala Ile Ile Val Gly Ala Gly Leu Ser Gly Ile Ser Ala Val Tyr Lys
             20                  25                  30

Leu Arg Lys Leu Arg Leu Asn Ala Lys Ile Phe Glu Gly Ala Pro Asp
         35                  40                  45

Phe Gly Gly Val Trp His Trp Asn Arg Tyr Pro Gly Ala Arg Val Asp
 50                  55                  60

Ser Glu Thr Pro Phe Tyr Gln Leu Asn Ile Pro Glu Val Trp Lys Asp
 65                  70                  75                  80

Trp Thr Trp Ser Cys Arg Tyr Pro Asp Gln Lys Glu Leu Leu Ser Tyr
                 85                  90                  95

Val His His Cys Asp Lys Ile Arg Gly Leu Arg Lys Asp Val Tyr Phe
            100                 105                 110

Gly Ala Glu Val Val Asp Ala Arg Tyr Ala Arg Asp Leu Gly Thr Trp
        115                 120                 125

Thr Val Lys Thr Ser Ala Gly His Val Ala Thr Ala Lys Tyr Leu Ile
    130                 135                 140

Leu Ala Thr Gly Leu Leu His Arg Lys His Thr Pro Ala Leu Pro Gly
145                 150                 155                 160

Leu Ala Asp Phe Asn Gly Lys Val Ile His Ser Ala Trp His Glu
                165                 170                 175

Asp Phe Asp Ala Glu Gly Gln Arg Val Ala Val Ile Gly Ala Gly Ala
            180                 185                 190

Thr Ser Ile Gln Ile Val Gln Glu Leu Ala Lys Lys Ala Asp Gln Val
        195                 200                 205

Thr Met Phe Met Arg Arg Pro Ser Tyr Cys Leu Pro Met Arg Gln Arg
    210                 215                 220

Thr Met Asp Arg Asn Glu Gln Thr Ala Trp Lys Ala Tyr Tyr Pro Thr
225                 230                 235                 240

Leu Phe Glu Ala Ser Arg Lys Ser Arg Ile Gly Phe Pro Val Gln Ala
                245                 250                 255

Pro Ser Val Gly Ile Phe Glu Val Ser Pro Glu Gln Arg Glu Ala Tyr
            260                 265                 270

Phe Glu Glu Leu Trp Glu Arg Gly Ala Phe Asn Phe Leu Ala Cys Gln
        275                 280                 285

Tyr Arg Glu Val Met Val Asp Lys Lys Ala Asn Arg Leu Val Tyr Asp
    290                 295                 300

Phe Trp Ala Lys Lys Thr Arg Ser Arg Ile Val Asn Pro Ala Lys Arg
305                 310                 315                 320

Asp Leu Met Ala Pro Leu Glu Pro Tyr Trp Phe Gly Thr Lys Arg
                325                 330                 335

Ser Pro Leu Glu Ser Asp Tyr Tyr Glu Met Leu Asp Lys Pro Ser Val
            340                 345                 350

Glu Ile Val Asn Leu Glu Gln Ser Pro Ile Val Ala Val Thr Lys Thr
        355                 360                 365
```

-continued

```
Gly Val Leu Leu Ser Asp Gly Ser Lys Arg Glu Cys Asp Thr Ile Val
    370                 375                 380

Leu Ala Thr Gly Phe Asp Ser Phe Thr Gly Ser Leu Thr His Met Gly
385                 390                 395                 400

Leu Lys Asn Lys His Gly Val Asp Leu Lys Glu Val Trp Lys Asp Gly
                405                 410                 415

Ile Ser Thr Tyr Met Gly Val Phe Ser His Gly Phe Pro Asn Ala Phe
            420                 425                 430

Phe Val Ala Thr Ala Gln Ala Pro Thr Val Leu Ser Asn Gly Pro Thr
        435                 440                 445

Ile Ile Glu Thr Gln Val Asp Leu Ile Ala Asp Thr Ile Ala Lys Leu
    450                 455                 460

Glu Ala Glu His Ala Thr Ser Val Glu Ala Thr Lys Ser Ala Gln Glu
465                 470                 475                 480

Ala Trp Ser Ile Met Ile Ala Lys Met Asn Glu His Thr Leu Phe Pro
                485                 490                 495

Leu Thr Asp Ser Trp Trp Thr Gly Gly Asn Ile Pro Gly Lys Ala Thr
            500                 505                 510

Arg Ala Leu Thr Phe Ile Gly Gly Ile Ala Leu Tyr Glu Gln Ile Cys
        515                 520                 525

Gln Glu Lys Val Ala Asn Trp Asp Gly Phe Asp Val Leu His Ala Pro
    530                 535                 540

Cys
545

<210> SEQ ID NO 4
<211> LENGTH: 1464
<212> TYPE: DNA
<213> ORGANISM: Exophiala spinifera
<220> FEATURE:
<221> NAME/KEY: CDS
<222> LOCATION: (1)...(1464)
<220> FEATURE:
<221> NAME/KEY: misc_feature
<222> LOCATION: (0)...(0)
<223> OTHER INFORMATION: aldehyde dehydrogenase, fully spliced DNA

<400> SEQUENCE: 4 atg gtt ctt tcg cct gac gaa tac aag agt gaa ctc ttc atc aac aat      48
Met Val Leu Ser Pro Asp Glu Tyr Lys Ser Glu Leu Phe Ile Asn Asn
 1               5                  10                  15 gaa ttc gtc tcc tcc aag ggg tcc gag aga tta acg ctc acg aac ccg      96
Glu Phe Val Ser Ser Lys Gly Ser Glu Arg Leu Thr Leu Thr Asn Pro
            20                  25                  30 tgg gac gaa tcc acc gtt gcc act gat gtt cac gtg gcc aac gcg gcc     144
Trp Asp Glu Ser Thr Val Ala Thr Asp Val His Val Ala Asn Ala Ala
        35                  40                  45 gat gtc gac agt gca gta gcc gct tcg gtg cag gcg gtc aaa aag ggc     192
Asp Val Asp Ser Ala Val Ala Ala Ser Val Gln Ala Val Lys Lys Gly
    50                  55                  60 cca tgg aag aag ttc aca ggt gca caa cgc gcg gcg tgc atg ctt aag     240
Pro Trp Lys Lys Phe Thr Gly Ala Gln Arg Ala Ala Cys Met Leu Lys
65                  70                  75                  80 ttc gcg gac ctc gcc gag aag aac gcc gag aag ctc gct cgt ctg gag     288
Phe Ala Asp Leu Ala Glu Lys Asn Ala Glu Lys Leu Ala Arg Leu Glu
                85                  90                  95 tcg ctg ccc acc ggt aga ccg gtg tcg atg atc act cat ttc gac att     336
Ser Leu Pro Thr Gly Arg Pro Val Ser Met Ile Thr His Phe Asp Ile
            100                 105                 110
```

-continued

```
cca aac atg gtc tcc gtg ttt cgc tac tat gca ggc tgg gcc gac aag    384
Pro Asn Met Val Ser Val Phe Arg Tyr Tyr Ala Gly Trp Ala Asp Lys
        115                 120                 125 atc gcc gga aag acc ttt ccc gag gac aac ggc aag ccg aat tgg cgt    432
Ile Ala Gly Lys Thr Phe Pro Glu Asp Asn Gly Lys Pro Asn Trp Arg
130                 135                 140 tac gag ccg atg ggg gtg tgt gct ggt att gcc agc tgg aac gcg act    480
Tyr Glu Pro Met Gly Val Cys Ala Gly Ile Ala Ser Trp Asn Ala Thr
145                 150                 155                 160 ttt ctt tac gtc ggc tgg aag ata gcc ccc gcc ctc gcc gcc ggc tgc    528
Phe Leu Tyr Val Gly Trp Lys Ile Ala Pro Ala Leu Ala Ala Gly Cys
                165                 170                 175 tcc ttc atc ttc aaa gcc tcg gag aaa tcc ccg ctg ggc gtt ctg ggc    576
Ser Phe Ile Phe Lys Ala Ser Glu Lys Ser Pro Leu Gly Val Leu Gly
            180                 185                 190 ctc gct cct ctc ttc gca gaa gcc gga ttc cct cct gga gtc gtg cag    624
Leu Ala Pro Leu Phe Ala Glu Ala Gly Phe Pro Pro Gly Val Val Gln
        195                 200                 205 ttc ctc act gga gca cga gtg acg ggt gaa gca ttg gcg tcg cac atg    672
Phe Leu Thr Gly Ala Arg Val Thr Gly Glu Ala Leu Ala Ser His Met
    210                 215                 220 gac att gcg aag atc agc ttc aca aga tct gtc ggc ggt ggc cgc gcc    720
Asp Ile Ala Lys Ile Ser Phe Thr Arg Ser Val Gly Gly Gly Arg Ala
225                 230                 235                 240 gtc aag caa gca aca ctc aag tcc aac atg aag cgc gtc act cta gaa    768
Val Lys Gln Ala Thr Leu Lys Ser Asn Met Lys Arg Val Thr Leu Glu
                245                 250                 255 ctg ggg gaa aag cca acc atc gtc ttc aac gaa gct cct ctc gaa cgg    816
Leu Gly Glu Lys Pro Thr Ile Val Phe Asn Glu Ala Pro Leu Glu Arg
            260                 265                 270 cag tcg ggg gaa tcg gca aag gat ttc tca aaa ttc ggg caa att tgg    864
Gln Ser Gly Glu Ser Ala Lys Asp Phe Ser Lys Phe Gly Gln Ile Trp
        275                 280                 285 gtc ccc ccc tcc tgt ttg cta gtg caa tgg gga aat tta gcg gag aaa    912
Val Pro Pro Ser Cys Leu Leu Val Gln Trp Gly Asn Leu Ala Glu Lys
    290                 295                 300 ttc cat gga gtc cgt cat ggc tca ttt gga ggc tgt cag aga tgg ctt    960
Phe His Gly Val Arg His Gly Ser Phe Gly Gly Cys Gln Arg Trp Leu
305                 310                 315                 320 ggc cag aac cca ttg gaa ccc aag agg acg cat ggt ccc ttc gtc gac    1008
Gly Gln Asn Pro Leu Glu Pro Lys Arg Thr His Gly Pro Phe Val Asp
                325                 330                 335 aag tcc cag tac gac aga gtc ttg ggt aac att gac gtt ggc aag gat    1056
Lys Ser Gln Tyr Asp Arg Val Leu Gly Asn Ile Asp Val Gly Lys Asp
            340                 345                 350 acc gcg cag ctc ctc act ggc gtt ggt aga aag ggc gac aag gga ttc    1104
Thr Ala Gln Leu Leu Thr Gly Val Gly Arg Lys Gly Asp Lys Gly Phe
        355                 360                 365 gcg att gaa ccg acg ata ttt gtc aat ccc aaa cca ggc agc aaa att    1152
Ala Ile Glu Pro Thr Ile Phe Val Asn Pro Lys Pro Gly Ser Lys Ile
    370                 375                 380 tgg ttt gag gag atc ttt ggc ccc gtc ttg tcc att aag acg ttc aag    1200
Trp Phe Glu Glu Ile Phe Gly Pro Val Leu Ser Ile Lys Thr Phe Lys
385                 390                 395                 400 acg gaa gaa gag gcc att gag att gcc aat gac acg act tat ggg cta    1248
Thr Glu Glu Glu Ala Ile Glu Ile Ala Asn Asp Thr Thr Tyr Gly Leu
                405                 410                 415 gcc tcg gtc att tat acc aaa tct ctc aac agg ggt ctc cgt gtc tcg    1296
Ala Ser Val Ile Tyr Thr Lys Ser Leu Asn Arg Gly Leu Arg Val Ser
            420                 425                 430
```

-continued

```
tcg gcg ctc gag acc ggt ggc gtc tcg atc aac ttc ccc ttt atc ccc    1344
Ser Ala Leu Glu Thr Gly Gly Val Ser Ile Asn Phe Pro Phe Ile Pro
        435                 440                 445 gag aca caa act ccg ttt ggc ggc atg aaa caa tcg ggc tca ggc aga    1392
Glu Thr Gln Thr Pro Phe Gly Gly Met Lys Gln Ser Gly Ser Gly Arg
450                 455                 460 gag cta ggc gaa gaa ggg ctc aag gcg tac ttg gag ccc aag acc att    1440
Glu Leu Gly Glu Glu Gly Leu Lys Ala Tyr Leu Glu Pro Lys Thr Ile
465                 470                 475                 480 aat atc cac gtc aac ata gag tga                                    1464
Asn Ile His Val Asn Ile Glu *
                485
```

<210> SEQ ID NO 5
<211> LENGTH: 487
<212> TYPE: PRT
<213> ORGANISM: Exophiala spinifera

<400> SEQUENCE: 5

```
Met Val Leu Ser Pro Asp Glu Tyr Lys Ser Glu Leu Phe Ile Asn Asn
  1               5                  10                  15

Glu Phe Val Ser Ser Lys Gly Ser Glu Arg Leu Thr Leu Thr Asn Pro
                 20                  25                  30

Trp Asp Glu Ser Thr Val Ala Thr Asp Val His Val Ala Asn Ala Ala
             35                  40                  45

Asp Val Asp Ser Ala Val Ala Ser Val Gln Ala Val Lys Lys Gly
         50                  55                  60

Pro Trp Lys Lys Phe Thr Gly Ala Gln Arg Ala Ala Cys Met Leu Lys
 65                  70                  75                  80

Phe Ala Asp Leu Ala Glu Lys Asn Ala Glu Lys Leu Ala Arg Leu Glu
                 85                  90                  95

Ser Leu Pro Thr Gly Arg Pro Val Ser Met Ile Thr His Phe Asp Ile
                100                 105                 110

Pro Asn Met Val Ser Val Phe Arg Tyr Tyr Ala Gly Trp Ala Asp Lys
            115                 120                 125

Ile Ala Gly Lys Thr Phe Pro Glu Asp Asn Gly Lys Pro Asn Trp Arg
130                 135                 140

Tyr Glu Pro Met Gly Val Cys Ala Gly Ile Ala Ser Trp Asn Ala Thr
145                 150                 155                 160

Phe Leu Tyr Val Gly Trp Lys Ile Ala Pro Ala Leu Ala Ala Gly Cys
                165                 170                 175

Ser Phe Ile Phe Lys Ala Ser Glu Lys Ser Pro Leu Gly Val Leu Gly
                180                 185                 190

Leu Ala Pro Leu Phe Ala Glu Ala Gly Phe Pro Pro Gly Val Val Gln
            195                 200                 205

Phe Leu Thr Gly Ala Arg Val Thr Gly Glu Ala Leu Ala Ser His Met
        210                 215                 220

Asp Ile Ala Lys Ile Ser Phe Thr Arg Ser Val Gly Gly Gly Arg Ala
225                 230                 235                 240

Val Lys Gln Ala Thr Leu Lys Ser Asn Met Lys Arg Val Thr Leu Glu
                245                 250                 255

Leu Gly Glu Lys Pro Thr Ile Val Phe Asn Glu Ala Pro Leu Glu Arg
                260                 265                 270

Gln Ser Gly Glu Ser Ala Lys Asp Phe Ser Lys Phe Gly Gln Ile Trp
            275                 280                 285
```

```
Val Pro Pro Ser Cys Leu Leu Val Gln Trp Gly Asn Leu Ala Glu Lys
    290                 295                 300
Phe His Gly Val Arg His Gly Ser Phe Gly Gly Cys Gln Arg Trp Leu
305                 310                 315                 320
Gly Gln Asn Pro Leu Glu Pro Lys Arg Thr His Gly Pro Phe Val Asp
                325                 330                 335
Lys Ser Gln Tyr Asp Arg Val Leu Gly Asn Ile Asp Val Gly Lys Asp
                340                 345                 350
Thr Ala Gln Leu Leu Thr Gly Val Gly Arg Lys Gly Asp Lys Gly Phe
            355                 360                 365
Ala Ile Glu Pro Thr Ile Phe Val Asn Pro Lys Pro Gly Ser Lys Ile
    370                 375                 380
Trp Phe Glu Glu Ile Phe Gly Pro Val Leu Ser Ile Lys Thr Phe Lys
385                 390                 395                 400
Thr Glu Glu Glu Ala Ile Glu Ile Ala Asn Asp Thr Thr Tyr Gly Leu
                405                 410                 415
Ala Ser Val Ile Tyr Thr Lys Ser Leu Asn Arg Gly Leu Arg Val Ser
                420                 425                 430
Ser Ala Leu Glu Thr Gly Gly Val Ser Ile Asn Phe Pro Phe Ile Pro
            435                 440                 445
Glu Thr Gln Thr Pro Phe Gly Gly Met Lys Gln Ser Gly Ser Gly Arg
    450                 455                 460
Glu Leu Gly Glu Gly Leu Lys Ala Tyr Leu Glu Pro Lys Thr Ile
465                 470                 475                 480
Asn Ile His Val Asn Ile Glu
                485

<210> SEQ ID NO 6
<211> LENGTH: 1764
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: permease, partially spliced cDNA

<400> SEQUENCE: 6
aactatggac tccagaccaa gtggatacgg cgagaaaggc gggacaaggc agacaacgaa    60
gaacacagag acggcggcgg caggtggtgc gtccgagtcc ctgaacgttc ctctggagaa   120
gaaacaattt ggcaccatca ccatcgtgtc cttggccttt gtgatttgca acagttgggc   180
tggtatctca ggcagtctcc agctcgccct actagcgggg gggcccgtca ctctccttta   240
cggcatccta atcagtactc tcgtctacat ctgcatcgct ttctcattag ccgaactgac   300
cagcgtctac ccgactgccg gtggccaata tcattttgcg tcgatcctgg caccaaaatc   360
aatcaatcgg agcatttcat acgtgtgcgg actcgtgtcg ttgctttcat ggatcgctat   420
cggaagctca gtgaccatga tacctgctca acagatcccg gcgctgatag ccgcctatag   480
tcacacatac tcccaggatt cgtggcatgt cttcctcatc tacgagggag tcgcgctggt   540
ggtgctcttg ttcaacttgt ttgccctgaa agaaaccct  tgggttcatg aaatcggatt   600
cggcctcacg atcgctctct tcgtgatctc ctttatcgcc attctagcgc ggtccaaccc   660
caaggctcca aactcacagg tatggactgc ttggagcaac tatactggct ggtccgacgg   720
cgtctgcttc atcctgggcc tttcgacatc ctgcttcatg ttcattggct tggacgcagc   780
aatgcatctg gctgaagaat gcacagatgc tgctcgtacg gtacccaaag cagtggtcag   840
```

-continued

```
tgcaatcata attggcttct gcaccgcctt tccatataca atcgcagttc tgtatggaat    900
tacagatctc gactctattc taagttccgc cggctatatt ccattcgaga caatgacgca    960
gtcccttcgg tcgctcagtt ttgcaacggt cctctcatgt ggcggtatcg tgatggcctt   1020
cttcgccctc aacgctgtac aagagactgc gtctcgactc acctggagct ttgcccggga   1080
caatgggctg gtattttcca ctcatctcga acgcattcat ccccgctggc aagttcctgt   1140
ttggtctcta ttcgcgacct ggggaattct ggccacatgc ggatgtatat ttctaggttc   1200
tagcacagct ttcaatgcct tggtcaattc cgccgttgta ctccagcaac tctccttcct   1260
gatcccaatc gccctactcc tctaccaaaa gcgagatcca aagttcttgc cgagcactcg   1320
tgcttttgtg ttaccgcgtg aatcgggtt tctggtcaat gtgctagcgg tggtcttcac    1380
gtccgtcacc actgtgtttt tcagcttccc actgaccgtg cctacggccg cgtcaaccat   1440
gaattacaca agtgcgatta taggcgttgc acttgctctt ggtgtcttga actgggtcgt   1500
gcatgccagg aagcattatc agggaccca cttggagctt gacggacggg tcgtcggagc    1560
agaatttcaa gttgggccat gaattggacg aaatggagac gcgtgtgcaa tgtcaaaaat   1620
tgctggggtg gtactgagag tctggattag ctgcaacgcg ggacaaccga gggtagaaca   1680
ctctgcaatc gagcaggaca atatcaatta ggcaachasv caaaaaaaaa aaaaaaaaa    1740 aaaaaagcgg ccgctgaatt ctag                                          1764

<210> SEQ ID NO 7
<211> LENGTH: 1578
<212> TYPE: DNA
<213> ORGANISM: Exophiala spinifera
<220> FEATURE:
<221> NAME/KEY: CDS
<222> LOCATION: (1)...(1578)
<220> FEATURE:
<221> NAME/KEY: misc_feature
<222> LOCATION: (0)...(0)
<223> OTHER INFORMATION: permease, fully spliced cDNA

<400> SEQUENCE: 7 atg gac tcc aga cca agt gga tac ggc gag aaa ggc ggg aca agg cag    48
Met Asp Ser Arg Pro Ser Gly Tyr Gly Glu Lys Gly Gly Thr Arg Gln
  1               5                  10                  15 aca acg aag aac aca gag acg gcg gcg gca ggt ggt gcg tcc gag tcc    96
Thr Thr Lys Asn Thr Glu Thr Ala Ala Ala Gly Gly Ala Ser Glu Ser
             20                  25                  30 ctg aac gtt cct ctg gag aag aaa caa ttt ggc acc atc acc atc gtg   144
Leu Asn Val Pro Leu Glu Lys Lys Gln Phe Gly Thr Ile Thr Ile Val
         35                  40                  45 tcc ttg gcc ttt gtg att tgc aac agt tgg gct ggt atc tca ggc agt   192
Ser Leu Ala Phe Val Ile Cys Asn Ser Trp Ala Gly Ile Ser Gly Ser
     50                  55                  60 ctc cag ctc gcc cta cta gcg ggg ggg ccc gtc act ctc ctt tac ggc   240
Leu Gln Leu Ala Leu Leu Ala Gly Gly Pro Val Thr Leu Leu Tyr Gly
 65                  70                  75                  80 atc cta atc agt act ctc gtc tac atc tgc atc gct ttc tca tta gcc   288
Ile Leu Ile Ser Thr Leu Val Tyr Ile Cys Ile Ala Phe Ser Leu Ala
                 85                  90                  95 gaa ctg acc agc gtc tac ccg act gcc ggt ggc caa tat cat ttt gcg   336
Glu Leu Thr Ser Val Tyr Pro Thr Ala Gly Gly Gln Tyr His Phe Ala
            100                 105                 110 tcg atc ctg gca cca aaa tca atc aat cgg agc att tca tac gtg tgc   384
Ser Ile Leu Ala Pro Lys Ser Ile Asn Arg Ser Ile Ser Tyr Val Cys
        115                 120                 125
```

| | | |
|---|---|---|
| gga ctc gtg tcg ttg ctt tca tgg atc gct atc gga agc tca gtg acc<br>Gly Leu Val Ser Leu Leu Ser Trp Ile Ala Ile Gly Ser Ser Val Thr<br>130                      135                      140 | | 432 |
| atg ata cct gct caa cag atc ccg gcg ctg ata gcc gcc tat agt cac<br>Met Ile Pro Ala Gln Gln Ile Pro Ala Leu Ile Ala Ala Tyr Ser His<br>145                      150                      155                      160 | | 480 |
| aca tac tcc cag gat tcg tgg cat gtc ttc ctc atc tac gag gga gtc<br>Thr Tyr Ser Gln Asp Ser Trp His Val Phe Leu Ile Tyr Glu Gly Val<br>                      165                      170                      175 | | 528 |
| gcg ctg gtg gtg ctc ttg ttc aac ttg ttt gcc ctg aaa aga aac cct<br>Ala Leu Val Val Leu Leu Phe Asn Leu Phe Ala Leu Lys Arg Asn Pro<br>                      180                      185                      190 | | 576 |
| tgg gtt cat gaa atc gga ttc ggc ctc acg atc gct ctc ttc gtg atc<br>Trp Val His Glu Ile Gly Phe Gly Leu Thr Ile Ala Leu Phe Val Ile<br>                      195                      200                      205 | | 624 |
| tcc ttt atc gcc att cta gcg cgg tcc aac ccc aag gct cca aac tca<br>Ser Phe Ile Ala Ile Leu Ala Arg Ser Asn Pro Lys Ala Pro Asn Ser<br>210                      215                      220 | | 672 |
| cag gta tgg act gct tgg agc aac tat act ggc tgg tcc gac ggc gtc<br>Gln Val Trp Thr Ala Trp Ser Asn Tyr Thr Gly Trp Ser Asp Gly Val<br>225                      230                      235                      240 | | 720 |
| tgc ttc atc ctg ggc ctt tcg aca tcc tgc ttc atg ttc att ggc ttg<br>Cys Phe Ile Leu Gly Leu Ser Thr Ser Cys Phe Met Phe Ile Gly Leu<br>                      245                      250                      255 | | 768 |
| gac gca gca atg cat ctg gct gaa gaa tgc aca gat gct gct cgt acg<br>Asp Ala Ala Met His Leu Ala Glu Glu Cys Thr Asp Ala Ala Arg Thr<br>                      260                      265                      270 | | 816 |
| gta ccc aaa gca gtg gtc agt gca atc ata att ggc ttc tgc acc gcc<br>Val Pro Lys Ala Val Val Ser Ala Ile Ile Ile Gly Phe Cys Thr Ala<br>                275                      280                      285 | | 864 |
| ttt cca tat aca atc gca gtt ctg tat gga att aca gat ctc gac tct<br>Phe Pro Tyr Thr Ile Ala Val Leu Tyr Gly Ile Thr Asp Leu Asp Ser<br>290                      295                      300 | | 912 |
| att cta agt tcc gcc ggc tat att cca ttc gag aca atg acg cag tcc<br>Ile Leu Ser Ser Ala Gly Tyr Ile Pro Phe Glu Thr Met Thr Gln Ser<br>305                      310                      315                      320 | | 960 |
| ctt cgg tcg ctc agt ttt gca acg gtc ctc tca tgt ggc ggt atc gtg<br>Leu Arg Ser Leu Ser Phe Ala Thr Val Leu Ser Cys Gly Gly Ile Val<br>                      325                      330                      335 | | 1008 |
| atg gcc ttc ttc gcc ctc aac gct gta caa gag act gcg tct cga ctc<br>Met Ala Phe Phe Ala Leu Asn Ala Val Gln Glu Thr Ala Ser Arg Leu<br>                      340                      345                      350 | | 1056 |
| acc tgg agc ttt gcc cgg gac aat ggg ctg gta ttt tcc act cat ctc<br>Thr Trp Ser Phe Ala Arg Asp Asn Gly Leu Val Phe Ser Thr His Leu<br>                      355                      360                      365 | | 1104 |
| gaa cgc att cat ccc cgc tgg caa gtt cct gtt tgg tct cta ttc gcg<br>Glu Arg Ile His Pro Arg Trp Gln Val Pro Val Trp Ser Leu Phe Ala<br>370                      375                      380 | | 1152 |
| acc tgg gga att ctg gcc aca tgc gga tgt ata ttt cta ggt tct agc<br>Thr Trp Gly Ile Leu Ala Thr Cys Gly Cys Ile Phe Leu Gly Ser Ser<br>385                      390                      395                      400 | | 1200 |
| aca gct ttc aat gcc ttg gtc aat tcc gcc gtt gta ctc cag caa ctc<br>Thr Ala Phe Asn Ala Leu Val Asn Ser Ala Val Val Leu Gln Gln Leu<br>                      405                      410                      415 | | 1248 |
| tcc ttc ctg atc cca atc gcc cta ctc ctc tac caa aag cga gat cca<br>Ser Phe Leu Ile Pro Ile Ala Leu Leu Leu Tyr Gln Lys Arg Asp Pro<br>                      420                      425                      430 | | 1296 |
| aag ttc ttg ccg agc act cgt gct ttt gtg tta ccg cgt gga atc ggg<br>Lys Phe Leu Pro Ser Thr Arg Ala Phe Val Leu Pro Arg Gly Ile Gly<br>                      435                      440                      445 | | 1344 |

-continued

```
ttt ctg gtc aat gtg cta gcg gtg gtc ttc acg tcc gtc acc act gtg    1392
Phe Leu Val Asn Val Leu Ala Val Val Phe Thr Ser Val Thr Thr Val
450                 455                 460 ttt ttc agc ttc cca ctg acc gtg cct acg gcc gcg tca acc atg aat    1440
Phe Phe Ser Phe Pro Leu Thr Val Pro Thr Ala Ala Ser Thr Met Asn
465                 470                 475                 480 tac aca agt gcg att ata ggc gtt gca ctt gct ctt ggt gtc ttg aac    1488
Tyr Thr Ser Ala Ile Ile Gly Val Ala Leu Ala Leu Gly Val Leu Asn
                485                 490                 495 tgg gtc gtg cat gcc agg aag cat tat cag gga ccc cac ttg gag ctt    1536
Trp Val Val His Ala Arg Lys His Tyr Gln Gly Pro His Leu Glu Leu
            500                 505                 510 gac gga cgg gtc gtc gga gca gaa ttt caa gtt ggg cca tga            1578
Asp Gly Arg Val Val Gly Ala Glu Phe Gln Val Gly Pro *
        515                 520                 525
```

<210> SEQ ID NO 8
<211> LENGTH: 525
<212> TYPE: PRT
<213> ORGANISM: Exophiala spinifera

<400> SEQUENCE: 8

```
Met Asp Ser Arg Pro Ser Gly Tyr Gly Glu Lys Gly Gly Thr Arg Gln
 1               5                  10                  15

Thr Thr Lys Asn Thr Glu Thr Ala Ala Gly Gly Ala Ser Glu Ser
                20                  25                  30

Leu Asn Val Pro Leu Glu Lys Lys Gln Phe Gly Thr Ile Thr Ile Val
            35                  40                  45

Ser Leu Ala Phe Val Ile Cys Asn Ser Trp Ala Gly Ile Ser Gly Ser
        50                  55                  60

Leu Gln Leu Ala Leu Leu Ala Gly Gly Pro Val Thr Leu Leu Tyr Gly
65                  70                  75                  80

Ile Leu Ile Ser Thr Leu Val Tyr Ile Cys Ile Ala Phe Ser Leu Ala
                85                  90                  95

Glu Leu Thr Ser Val Tyr Pro Thr Ala Gly Gly Gln Tyr His Phe Ala
            100                 105                 110

Ser Ile Leu Ala Pro Lys Ser Ile Asn Arg Ser Ile Ser Tyr Val Cys
        115                 120                 125

Gly Leu Val Ser Leu Leu Ser Trp Ile Ala Ile Gly Ser Ser Val Thr
130                 135                 140

Met Ile Pro Ala Gln Gln Ile Pro Ala Leu Ile Ala Tyr Ser His
145                 150                 155                 160

Thr Tyr Ser Gln Asp Ser Trp His Val Phe Leu Ile Tyr Glu Gly Val
                165                 170                 175

Ala Leu Val Val Leu Leu Phe Asn Leu Phe Ala Leu Lys Arg Asn Pro
            180                 185                 190

Trp Val His Glu Ile Gly Phe Gly Leu Thr Ile Ala Leu Phe Val Ile
        195                 200                 205

Ser Phe Ile Ala Ile Leu Ala Arg Ser Asn Pro Lys Ala Pro Asn Ser
210                 215                 220

Gln Val Trp Thr Ala Trp Ser Asn Tyr Thr Gly Trp Ser Asp Gly Val
225                 230                 235                 240

Cys Phe Ile Leu Gly Leu Ser Thr Ser Cys Phe Met Phe Ile Gly Leu
                245                 250                 255

Asp Ala Ala Met His Leu Ala Glu Glu Cys Thr Asp Ala Ala Arg Thr
            260                 265                 270
```

-continued

```
Val Pro Lys Ala Val Ser Ala Ile Ile Ile Gly Phe Cys Thr Ala
        275                 280                 285
Phe Pro Tyr Thr Ile Ala Val Leu Tyr Gly Ile Thr Asp Leu Asp Ser
    290                 295                 300
Ile Leu Ser Ser Ala Gly Tyr Ile Pro Phe Glu Thr Met Thr Gln Ser
305                 310                 315                 320
Leu Arg Ser Leu Ser Phe Ala Thr Val Leu Ser Cys Gly Gly Ile Val
                325                 330                 335
Met Ala Phe Phe Ala Leu Asn Ala Val Gln Glu Thr Ala Ser Arg Leu
            340                 345                 350
Thr Trp Ser Phe Ala Arg Asp Asn Gly Leu Val Phe Ser Thr His Leu
        355                 360                 365
Glu Arg Ile His Pro Arg Trp Gln Val Pro Val Trp Ser Leu Phe Ala
    370                 375                 380
Thr Trp Gly Ile Leu Ala Thr Cys Gly Cys Ile Phe Leu Gly Ser Ser
385                 390                 395                 400
Thr Ala Phe Asn Ala Leu Val Asn Ser Ala Val Val Leu Gln Gln Leu
                405                 410                 415
Ser Phe Leu Ile Pro Ile Ala Leu Leu Leu Tyr Gln Lys Arg Asp Pro
            420                 425                 430
Lys Phe Leu Pro Ser Thr Arg Ala Phe Val Leu Pro Arg Gly Ile Gly
        435                 440                 445
Phe Leu Val Asn Val Leu Ala Val Val Phe Thr Ser Val Thr Thr Val
    450                 455                 460
Phe Phe Ser Phe Pro Leu Thr Val Pro Thr Ala Ala Ser Thr Met Asn
465                 470                 475                 480
Tyr Thr Ser Ala Ile Ile Gly Val Ala Leu Ala Leu Gly Val Leu Asn
                485                 490                 495
Trp Val Val His Ala Arg Lys His Tyr Gln Gly Pro His Leu Glu Leu
        500                 505                 510
Asp Gly Arg Val Val Gly Ala Glu Phe Gln Val Gly Pro
    515                 520                 525
```

<210> SEQ ID NO 9
<211> LENGTH: 3999
<212> TYPE: DNA
<213> ORGANISM: Exophiala spinifera
<220> FEATURE:
<221> NAME/KEY: misc_feature
<222> LOCATION: (0)...(0)
<223> OTHER INFORMATION: p-glycoprotein, with introns

<400> SEQUENCE: 9

| | | |
|---|---|---|
| tatttsccat ctmckatgaa tgcagatga atcggagaaa cctcgaccaa accaagatgg | 60 |
| cagtgagtcg tcctcacacc ctcccccaga aaaggaaacc gaaggcagta tttcagacta | 120 |
| tctacgaatc ttcagatatg ccgacaaata cgactggact ctcaatgtca tcgcgctcat | 180 |
| ctgcgccatc ggatccgggg cttcccttcc tctgatgtcg atcatcttcg gtagcttcac | 240 |
| caacaagttc aacaattaca attcgggcga cgggagtcct gaagcgttca aggccgatgt | 300 |
| ggatcatttc gtcctgtggt tcgtctacct ctttattggg aagtttgtcc tcacgtacgt | 360 |
| ttccacggct gccattacca tttcagctat acgaaccact cgaactcttc gacgagtgtt | 420 |
| ccttgaatgc accttgcggc aagaggtctg gcatttcgac aagcagagca atggagcaat | 480 |
| cgccactcag gtcactacca atggcaaccg tatacaaaca ggtattgccg agaaaattgt | 540 |

-continued

```
ctttaccgtg caggcacttt caatgttctt ttctgcattt gtggtcgctt tggcgtctca      600
gtggaagcta gctttaatca ccatgtccgt catccctgcc attttcctgg tcaccggcat      660
ctgcatagca attgatgccg ctcaggaggc caggatcacc aggatctact cacgcgccgc      720
tgtcctcgca gaagaagtct tatcatccat ccggacagtc catgctttct acgcccagaa      780
gaaaatggtc gaaaaatatg atgtcttttt gcagcaagca caccaagaag gaagaagaa       840 atcgccaaat tatgggtct tgttctcaac tgagtacttt tgcatttacg ctgctatcgc       900
actgggcctt ttgggaaagg ttttcgcat gtatcagaat ggcgaggttg ccgacgttgg       960
caaagtcttt actgttgcct ttccgtcacc tttagcagcc acgtccatct caatgcttgc     1020
gccttcaggt tcagtcgttt accaacgccg catcttcggc ctccgaatta ttcagtatca     1080
ttgacaaacc cacgcagctc gacccttctc gaccctttt ggaaagcagc cagagggctg      1140
cttaggtcaa attgagatcc aaaacctggc atttgcctac ccctcccgac catctgccca     1200
agtacttcga gatttcaact tgacaattcc agctggcaag acgacggccc tcgtcggtgc     1260
atcaggtagc ggcaaaagca caatggtcgg cttacttgaa cggtggtatc tgcccagttc     1320
ggggaggata ttacttgatg ggttggaact gggacaatac aatgtgaaat ggctgagaag     1380
ccgcattcgc ctcgttcaac aggaacctgt gttgtttcgt ggcacaatct tccagaacat     1440
tgccaacggt tcatggatg agcaacgaga tctgcctcgc gaaaacaaa tggagcttgt       1500 gcaaaaagct tgcaaagcag caatgccgac gtgttcatta atgagcttcc gaacggttat     1560
gagactgaag ttggcgagcg agccggagcc ttgagtggag gtcaacaagc cgaattgcaa     1620
tcgcacgaag tatcatatcg gatcccaaga tcctgttact cgatgaagct accagcgccc     1680
ttgacccgaa gcggagaaa gtggtccagg aggccttgaa ccgagtgtcc aaagaccgca     1740
ctactttggt cattgcccac aaactagcca ctgtcatacg actcactatt agggcgaatt     1800
gggccctcta gatgcatgct cgagcggccg ccagtgtgac gaattgatgc agaattcggc     1860
ttgtcattac gccgcactgg tgcgtgcaca ggaccctcggg gctgacgaac aagaagaaca    1920
tgagaagacc ctgcacgaaa aggcagcacg agaagctgct ggtgaacgac cggcacttga     1980
gcgcactcac accactgcca catctcaagc tggagacctg gagaagcgga aggtgccggt     2040
cgggactttg ggctactcgc tcctaaaatg catcctaatc atgttctacg aacaaaaaaa     2100
tctctactgg tgcttcttgt tgtcaacaat agcggttctg atatgcgcgg ccacatttcc     2160
aggacaagcc ctttgttttt cgagattgct cactgtcttc gagttgagtg gtcatgcggc     2220
acaggaacgg gcagacttt atagtctgat gttctttgtc gtggctctag aaatctagt      2280 aggatatttc acgattggct ggacatgcaa cgttgtttca caagttgtca cccatcgcta     2340
tcgagccgaa atgttccaac gagtactgga tcaagacatc gaattcttcg acatcccgga     2400
gaatacttct ggtgctctca catcgcaact gtcagctcta cccacgcagt gcaggagtt      2460 gatatcaaca aattcttctc attttatcg ttgtcgtaca acatcctctc gagcagtgct      2520
ctagcactag cctatggatg gaaactgggc ctggtggttg tgtttggtgc acttccaccc     2580
ctgcttttgg ctggctacct cagaattcgt cttgagacga agctagaagc cggaaactcg     2640
gcaaactttg cagaaagtgc tgggcttgca agcgaagcag ttaccgcgat ccggaccgtc     2700
tcatctttga ctctcgaagg scatgttctc aacagtact cggacatgtt gagcaaggtc      2760
gtgctaagat catccaaagc tttggtttgg acgatgtttt ggttctcact gtcacagtcg     2820
atcgagtttc tggctatggc cctgggaatt ttggtatggg aagtcgacta ctggcttcag     2880
gtgaggtacg acacaactca attttatatc atcttcgtgg gcgttttgtt tgccggtcca     2940
```

-continued

```
agcagcagcc cagaagccga attactccac gagtcttacc aaggctcggt cggctgcgaa    3000
ctatatcctc tggctgcgga cattgaagcc gaccatccgc gaaacggagg agaacaagaa    3060
aaaagggcca gtgggtggat gccctgtcga cctcgaggac attgaattca ggtatcgtca    3120
acgtgattcg gctcgagttc tccgcggggt ttccatgaca atcgagccag acaatttgt     3180 agcttatgtg ggcgcttctg gctgtggcaa gtcaacgttg atcgctttgt tggaacgatt    3240
ctacgacccg acctcgggcc gaatttcatt tgcacacgag aatattgcag aaatgtcgcc    3300
gcgcttgtac cgcggccata tgtctttggt ccaacaggaa cccacayttt accaaggctc    3360
cgttcgcgag aatgtgacgt tggccctcga agccgaatta tcagaagagc tttgtcaagg    3420
acgccttccc gcaaggccaa tgctttggat tttgtcatct ctttaccaga aggctttgaa    3480
acgccttgcg gctcaacgag ggatgcagtt ctccggcggg caacgacagc ggatcgccat    3540
cgcaagagca ttgattcgaa atccaaagct gttgctactt gacgaagcga cgtcagccct    3600
cgacacgcaa tcggaacgtc tggttcaagc tgccctcgat gaggcatcca cgagccgaac    3660
gacaatagca gtggcgcacc gactttccac tattcggaat gttgatgtta tttttgtgtt    3720
tgccaacggg agaatcgccg aaacgggcac tcacgcggaa ctacaacgac tgagaggaag    3780
atattacgag atgtgtttgg cacaatcttt agaccaagca tgagcgttca cagaagagcg    3840
gaaaagggcg gtgggatctt ttaggatagg tttagtggcg tgttacttac tacaggcgtt    3900
tggattcagg tacgacaact tgtacaataa gtagcataga gcatgtaatg aaagggtact    3960 cgtcccgaa aaaaaaaaa aaaaaaaaa aaaaaaaa                                3999
```

<210> SEQ ID NO 10
<211> LENGTH: 3792
<212> TYPE: DNA
<213> ORGANISM: Exophiala spinifera
<220> FEATURE:
<221> NAME/KEY: CDS
<222> LOCATION: (1)...(3792)
<220> FEATURE:
<221> NAME/KEY: misc_feature
<222> LOCATION: (0)...(0)
<223> OTHER INFORMATION: p-glycoprotein, fully spliced cDNA

<400> SEQUENCE: 10

```
atg gca gat gaa tcg gag aaa cct cga cca aac caa gat ggc agt gag     48
Met Ala Asp Glu Ser Glu Lys Pro Arg Pro Asn Gln Asp Gly Ser Glu
1               5                   10                  15 tcg tcc tca cac cct ccc cca gaa aag gaa acc gaa ggc agt att tca     96
Ser Ser Ser His Pro Pro Pro Glu Lys Glu Thr Glu Gly Ser Ile Ser
            20                  25                  30 gac tat cta cga atc ttc aga tat gcc gac aaa tac gac tgg act ctc    144
Asp Tyr Leu Arg Ile Phe Arg Tyr Ala Asp Lys Tyr Asp Trp Thr Leu
        35                  40                  45 aat gtc atc gcg ctc atc tgc gcc atc gga tcc ggg gct tcc ctt cct    192
Asn Val Ile Ala Leu Ile Cys Ala Ile Gly Ser Gly Ala Ser Leu Pro
    50                  55                  60 ctg atg tcg atc atc ttc ggt agc ttc acc aac aag ttc aac aat tac    240
Leu Met Ser Ile Ile Phe Gly Ser Phe Thr Asn Lys Phe Asn Asn Tyr
65                  70                  75                  80 aat tcg ggc gac ggg agt cct gaa gcg ttc aag gcc gat gtg gat cat    288
Asn Ser Gly Asp Gly Ser Pro Glu Ala Phe Lys Ala Asp Val Asp His
                85                  90                  95 ttc gtc ctg tgg ttc gtc tac ctc ttt att ggg aag ttt gtc ctc acg    336
Phe Val Leu Trp Phe Val Tyr Leu Phe Ile Gly Lys Phe Val Leu Thr
```

```
            100                 105                 110
tac gtt tcc acg gct gcc att acc att tca gct ata cga acc act cga    384
Tyr Val Ser Thr Ala Ala Ile Thr Ile Ser Ala Ile Arg Thr Thr Arg
        115                 120                 125 act ctt cga cga gtg ttc ctt gaa tgc acc ttg cgg caa gag gtc tgg    432
Thr Leu Arg Arg Val Phe Leu Glu Cys Thr Leu Arg Gln Glu Val Trp
    130                 135                 140 cat ttc gac aag cag agc aat gga gca atc gcc act car gtc act acc    480
His Phe Asp Lys Gln Ser Asn Gly Ala Ile Ala Thr Gln Val Thr Thr
145                 150                 155                 160 aat ggc aac cgt ata caa aca ggt att gcc gag aaa ttg gtc ttt acc    528
Asn Gly Asn Arg Ile Gln Thr Gly Ile Ala Glu Lys Leu Val Phe Thr
            165                 170                 175 gtg cag gca ctt tca atg ttc ttt tct gca ttt gtg gtc gct ttg gcg    576
Val Gln Ala Leu Ser Met Phe Phe Ser Ala Phe Val Val Ala Leu Ala
        180                 185                 190 tct cag tgg aag cta gct tta atc acc atg tcc gtc atc cct gcc att    624
Ser Gln Trp Lys Leu Ala Leu Ile Thr Met Ser Val Ile Pro Ala Ile
    195                 200                 205 ttc ctg gtc acc ggc atc tgc ata gca att gat gcc gct cag gag gcc    672
Phe Leu Val Thr Gly Ile Cys Ile Ala Ile Asp Ala Ala Gln Glu Ala
210                 215                 220 agg atc acc agg atc tac tca cgc gcc gct gtc ctc gca gaa gaa gtc    720
Arg Ile Thr Arg Ile Tyr Ser Arg Ala Ala Val Leu Ala Glu Glu Val
225                 230                 235                 240 tta tca tcc atc cgg aca gtc cat gct ttc tac gcc cag aag aaa atg    768
Leu Ser Ser Ile Arg Thr Val His Ala Phe Tyr Ala Gln Lys Lys Met
            245                 250                 255 gtc gaa aaa tat gat gtc ttt ttg cag caa gca cac caa gaa ggg aag    816
Val Glu Lys Tyr Asp Val Phe Leu Gln Gln Ala His Gln Glu Gly Lys
        260                 265                 270 aag aaa tcg cca aat aat ggs gtc ttg ttc tca act gag tac ttt tgc    864
Lys Lys Ser Pro Asn Asn Xaa Val Leu Phe Ser Thr Glu Tyr Phe Cys
    275                 280                 285 att tac gct gct atc gca ctg gcc ttt tgg aaa ggt ttt cgc atg tat    912
Ile Tyr Ala Ala Ile Ala Leu Ala Phe Trp Lys Gly Phe Arg Met Tyr
290                 295                 300 cag aat ggc gag gtt gcc gac gtt ggc aaa gtc ttt act gtt gtc ctt    960
Gln Asn Gly Glu Val Ala Asp Val Gly Lys Val Phe Thr Val Val Leu
305                 310                 315                 320 tcc gtc acc tta gca gcc acg tcc atc tca atg ctt gcg cct tca ggt   1008
Ser Val Thr Leu Ala Ala Thr Ser Ile Ser Met Leu Ala Pro Ser Gly
            325                 330                 335 tca gtc gtt tac caa cgc cgc atc ttc ggc tcc gaa tta ttc agt atc   1056
Ser Val Val Tyr Gln Arg Arg Ile Phe Gly Ser Glu Leu Phe Ser Ile
        340                 345                 350 att gac aaa ccc acg cag ctc gac cct ctc gac cct tct gga aag cag   1104
Ile Asp Lys Pro Thr Gln Leu Asp Pro Leu Asp Pro Ser Gly Lys Gln
    355                 360                 365 cca gag ggc tgc cta ggt caa att gag atc caa aac ctg gca ttt gcc   1152
Pro Glu Gly Cys Leu Gly Gln Ile Glu Ile Gln Asn Leu Ala Phe Ala
370                 375                 380 tac ccc tcc cga cca tct gcc caa gta ctt cga gat ttc aac ttg aca   1200
Tyr Pro Ser Arg Pro Ser Ala Gln Val Leu Arg Asp Phe Asn Leu Thr
385                 390                 395                 400 att cca gct ggc aag acg acg gcc ctc gtc ggt gca tca ggt agc ggc   1248
Ile Pro Ala Gly Lys Thr Thr Ala Leu Val Gly Ala Ser Gly Ser Gly
            405                 410                 415 aaa agc aca atg gtc ggc tta ctt gaa cgg tgg tat ctg ccc agt tcg   1296
```

-continued

```
                Lys Ser Thr Met Val Gly Leu Leu Glu Arg Trp Tyr Leu Pro Ser Ser
                                420                 425                 430 ggg agg ata tta ctt gat ggg ttg gaa ctg gga caa tac aat gtg aaa          1344
Gly Arg Ile Leu Leu Asp Gly Leu Glu Leu Gly Gln Tyr Asn Val Lys
            435                 440                 445 tgg ctg aga agc cgc att cgc ctc gtt caa cag gaa cct gtg ttg ttt          1392
Trp Leu Arg Ser Arg Ile Arg Leu Val Gln Gln Glu Pro Val Leu Phe
        450                 455                 460 cgt ggc aca atc ttc cag aac att gcc aac ggt ttc atg gat gag caa          1440
Arg Gly Thr Ile Phe Gln Asn Ile Ala Asn Gly Phe Met Asp Glu Gln
465                 470                 475                 480 cga gat ctg cct cgc gaa aaa caa atg gag ctt gtg caa aaa gct tgc          1488
Arg Asp Leu Pro Arg Glu Lys Gln Met Glu Leu Val Gln Lys Ala Cys
                485                 490                 495 aaa gcc agc aat ggc gac gtg ttc att aat gag ctt ccg aac ggt tat          1536
Lys Ala Ser Asn Gly Asp Val Phe Ile Asn Glu Leu Pro Asn Gly Tyr
            500                 505                 510 gag act gaa gtt ggc gag cga gcc gga gcc ttg agt gga ggt caa cga          1584
Glu Thr Glu Val Gly Glu Arg Ala Gly Ala Leu Ser Gly Gly Gln Arg
        515                 520                 525 caa cga att gca atc gca cga agt atc ata tcg gat ccc aag atc ctg          1632
Gln Arg Ile Ala Ile Ala Arg Ser Ile Ile Ser Asp Pro Lys Ile Leu
    530                 535                 540 tta ctc gat gaa gct acc agc gcc ctt gac ccg aag gcg gag aaa gtg          1680
Leu Leu Asp Glu Ala Thr Ser Ala Leu Asp Pro Lys Ala Glu Lys Val
545                 550                 555                 560 gtc cag gag gcc ttg aac cga gtg tcc aaa gac cgc act act ttg gtc          1728
Val Gln Glu Ala Leu Asn Arg Val Ser Lys Asp Arg Thr Thr Leu Val
                565                 570                 575 att gcc cac aaa cta gcc act gtc aaa agt gct ggc aac atc gca gtc          1776
Ile Ala His Lys Leu Ala Thr Val Lys Ser Ala Gly Asn Ile Ala Val
            580                 585                 590 att tcc cag ggg aaa atc gtc gag caa ggc aca cac cac gaa ttg atc          1824
Ile Ser Gln Gly Lys Ile Val Glu Gln Gly Thr His His Glu Leu Ile
        595                 600                 605 gaa ttc ggc tgt cat tac gcc gca ctg gtg cgt gca cag gac ctc ggg          1872
Glu Phe Gly Cys His Tyr Ala Ala Leu Val Arg Ala Gln Asp Leu Gly
    610                 615                 620 gct gac gaa caa caa gaa cat gag aag acc ctg cac gaa aag gca gca          1920
Ala Asp Glu Gln Gln Glu His Glu Lys Thr Leu His Glu Lys Ala Ala
625                 630                 635                 640 cga gaa gct gct ggt gaa cga ccg gca ctt gag cgc act cac acc act          1968
Arg Glu Ala Ala Gly Glu Arg Pro Ala Leu Glu Arg Thr His Thr Thr
                645                 650                 655 gcc aca tct caa gct gga gac ctg gag aag cgg aag gtg ccg gtc ggg          2016
Ala Thr Ser Gln Ala Gly Asp Leu Glu Lys Arg Lys Val Pro Val Gly
            660                 665                 670 act ttg ggc tac tcg ctc cta aaa tgc atc cta atc atg ttc tac gaa          2064
Thr Leu Gly Tyr Ser Leu Leu Lys Cys Ile Leu Ile Met Phe Tyr Glu
        675                 680                 685 caa aaa aat ctc tac tgg tgc ttc ttg ttg tca aca ata acg gtt ctg          2112
Gln Lys Asn Leu Tyr Trp Cys Phe Leu Leu Ser Thr Ile Thr Val Leu
    690                 695                 700 ata tgc gcg gcc aca ttt cca gga caa gcc ctt ttg ttt tcg aga ttg          2160
Ile Cys Ala Ala Thr Phe Pro Gly Gln Ala Leu Leu Phe Ser Arg Leu
705                 710                 715                 720 ctc act gtc ttc gag ttg agt ggt cat gcg gca cag gaa cgg gca gac          2208
Leu Thr Val Phe Glu Leu Ser Gly His Ala Ala Gln Glu Arg Ala Asp
                725                 730                 735
```

```
ttt tat att ctg atg ttc ttt gtc gtg gct cta gga aat cta gta gga      2256
Phe Tyr Ile Leu Met Phe Phe Val Val Ala Leu Gly Asn Leu Val Gly
            740                 745                 750 tat ttc acg att ggc tgg aca tgc aac gtt att tca caa gtt gtc acc      2304
Tyr Phe Thr Ile Gly Trp Thr Cys Asn Val Ile Ser Gln Val Val Thr
        755                 760                 765 cat cgc tat caa gcc gca atg ttc caa cga gta ctg gat caa gac atc      2352
His Arg Tyr Gln Ala Ala Met Phe Gln Arg Val Leu Asp Gln Asp Ile
    770                 775                 780 gaa ctc ctc gac atc ccg gag caa att tct ggt gct ctc aca tcg caa      2400
Glu Leu Leu Asp Ile Pro Glu Gln Ile Ser Gly Ala Leu Thr Ser Gln
785                 790                 795                 800 ctg tca gct cta ccc acg cag ttg caa gag ttg ata tca gca aat ttt      2448
Leu Ser Ala Leu Pro Thr Gln Leu Gln Glu Leu Ile Ser Ala Asn Phe
                805                 810                 815 ctc att tat atc gtt gtc ggt caa cat cgt ctc gag cag tgc tct acc      2496
Leu Ile Tyr Ile Val Val Gly Gln His Arg Leu Glu Gln Cys Ser Thr
            820                 825                 830 act agc cta tgg atg gaa act ggg cct ggt ggt tgt gtt tgg tgc act      2544
Thr Ser Leu Trp Met Glu Thr Gly Pro Gly Gly Cys Val Trp Cys Thr
        835                 840                 845 tcc acc cct gct ttt ggc tgg cta cct cag aat tcg tct aga gac gaa      2592
Ser Thr Pro Ala Phe Gly Trp Leu Pro Gln Asn Ser Ser Arg Asp Glu
    850                 855                 860 gct aga agc cgg aaa ctc ggc aaa ctt tgc aga aag tgc tgg gct tgc      2640
Ala Arg Ser Arg Lys Leu Gly Lys Leu Cys Arg Lys Cys Trp Ala Cys
865                 870                 875                 880 aag cga agc agt tac cgc gat ccg gac cgt ctc atc ttt gac tct cga      2688
Lys Arg Ser Ser Tyr Arg Asp Pro Asp Arg Leu Ile Phe Asp Ser Arg
                885                 890                 895 agg cca tgt tct cca aca gta ctc gga cat gtt gag caa ggt ctt gct      2736
Arg Pro Cys Ser Pro Thr Val Leu Gly His Val Glu Gln Gly Leu Ala
            900                 905                 910 aag atc atc caa agc ttt tgg ttt gga cga tgt ttt ggt ttt cac ttg      2784
Lys Ile Ile Gln Ser Phe Trp Phe Gly Arg Cys Phe Gly Phe His Leu
        915                 920                 925 tca cag tcg atg gag ttt ttg gct att gcc ctg gga ttt tgt att gca      2832
Ser Gln Ser Met Glu Phe Leu Ala Ile Ala Leu Gly Phe Cys Ile Ala
    930                 935                 940 gtc gat aat tgg ctt cag gtg agt acg aca caa ctc aat ttt ata tca      2880
Val Asp Asn Trp Leu Gln Val Ser Thr Thr Gln Leu Asn Phe Ile Ser
945                 950                 955                 960 tct tcg tgg gcg ttt tgt ttg ccg gtc caa gca gca gcc cag tat ttg      2928
Ser Ser Trp Ala Phe Cys Leu Pro Val Gln Ala Ala Ala Gln Tyr Leu
                965                 970                 975 gct tac tcc acg agt ttt acc aag gct cgg tcg gct gcg aac tat atc      2976
Ala Tyr Ser Thr Ser Phe Thr Lys Ala Arg Ser Ala Ala Asn Tyr Ile
            980                 985                 990 ctc tgg ctg cgg aca ttg aag ccg acc atc cgc gaa acg gag gag aac      3024
Leu Trp Leu Arg Thr Leu Lys Pro Thr Ile Arg Glu Thr Glu Glu Asn
        995                 1000                1005 aag aaa aaa ggc cca gtg ggt gga tgc cct gtc gac ctc gag gac att      3072
Lys Lys Lys Gly Pro Val Gly Gly Cys Pro Val Asp Leu Glu Asp Ile
    1010                1015                1020 gaa ttc agg tat cgt caa cgt gat tcg gct cga gtt ctc cgc ggg gtt      3120
Glu Phe Arg Tyr Arg Gln Arg Asp Ser Ala Arg Val Leu Arg Gly Val
1025                1030                1035                1040 tcc atg aca atc gag cca gga caa ttt gta gct tat gtg ggc gct tct      3168
Ser Met Thr Ile Glu Pro Gly Gln Phe Val Ala Tyr Val Gly Ala Ser
                1045                1050                1055
```

```
ggc tgt ggc aag tca acg ttg atc gct ttg tcg gaa cga ttc tac gac    3216
Gly Cys Gly Lys Ser Thr Leu Ile Ala Leu Ser Glu Arg Phe Tyr Asp
            1060                1065                1070 ccg acc tcg ggc cga att tca ttt gca cac gag aat att gca gaa atg    3264
Pro Thr Ser Gly Arg Ile Ser Phe Ala His Glu Asn Ile Ala Glu Met
        1075                1080                1085 tcg ccg cgc ttg tac cgc ggc cat atg tct ttg gtc caa cag gaa ccc    3312
Ser Pro Arg Leu Tyr Arg Gly His Met Ser Leu Val Gln Gln Glu Pro
    1090                1095                1100 aca ctt tac caa ggc tcc gtt cgc gag aat gtg acg ttg gcc ctc gaa    3360
Thr Leu Tyr Gln Gly Ser Val Arg Glu Asn Val Thr Leu Ala Leu Glu
1105                1110                1115                1120 gcc gaa tta tca gaa gag ctt tgt caa gga cgc ctt ccc gca agg cca    3408
Ala Glu Leu Ser Glu Glu Leu Cys Gln Gly Arg Leu Pro Ala Arg Pro
                1125                1130                1135 atg ctt tgg att ttg tca tct ctt tac cag aag gct ttg aaa cgc ctt    3456
Met Leu Trp Ile Leu Ser Ser Leu Tyr Gln Lys Ala Leu Lys Arg Leu
            1140                1145                1150 gcg gct caa cga ggg atg cag ttc tcc ggc ggg caa cga cag cgg atc    3504
Ala Ala Gln Arg Gly Met Gln Phe Ser Gly Gly Gln Arg Gln Arg Ile
        1155                1160                1165 gcc atc gca aga gca ttg att cga aat cca aag ctg ttg cta ctt gac    3552
Ala Ile Ala Arg Ala Leu Ile Arg Asn Pro Lys Leu Leu Leu Leu Asp
    1170                1175                1180 gaa gcg acg tca gcc ctc gac acg caa tcg gaa cgt ctg gtt caa gct    3600
Glu Ala Thr Ser Ala Leu Asp Thr Gln Ser Glu Arg Leu Val Gln Ala
1185                1190                1195                1200 gcc ctc gat gag gca tcc acg agc cga acg aca ata gca gtg gcg cac    3648
Ala Leu Asp Glu Ala Ser Thr Ser Arg Thr Thr Ile Ala Val Ala His
                1205                1210                1215 cga ctt tcc act att cgg aat gtt gat gtt att ttt gtg ttt gcc aac    3696
Arg Leu Ser Thr Ile Arg Asn Val Asp Val Ile Phe Val Phe Ala Asn
            1220                1225                1230 ggg aga atc gcc gaa acg ggc act cac gcg gaa cta caa cga ctg aga    3744
Gly Arg Ile Ala Glu Thr Gly Thr His Ala Glu Leu Gln Arg Leu Arg
        1235                1240                1245 gga aga tat tac gag atg tgt ttg gca caa tct tta gac caa gca tga    3792
Gly Arg Tyr Tyr Glu Met Cys Leu Ala Gln Ser Leu Asp Gln Ala  *
    1250                1255                1260
```

<210> SEQ ID NO 11
<211> LENGTH: 1263
<212> TYPE: PRT
<213> ORGANISM: Exophiala spinifera
<220> FEATURE:
<221> NAME/KEY: UNSURE
<222> LOCATION: (0)...(0)
<223> OTHER INFORMATION: Xaa is any amino acid

<400> SEQUENCE: 11

```
Met Ala Asp Glu Ser Glu Lys Pro Arg Pro Asn Gln Asp Gly Ser Glu
 1               5                  10                  15

Ser Ser Ser His Pro Pro Glu Lys Glu Thr Glu Gly Ser Ile Ser
            20                  25                  30

Asp Tyr Leu Arg Ile Phe Arg Tyr Ala Asp Lys Tyr Asp Trp Thr Leu
         35                  40                  45

Asn Val Ile Ala Leu Ile Cys Ala Ile Gly Ser Gly Ala Ser Leu Pro
     50                  55                  60

Leu Met Ser Ile Ile Phe Gly Ser Phe Thr Asn Lys Phe Asn Asn Tyr
65                  70                  75                  80
```

```
Asn Ser Gly Asp Gly Ser Pro Glu Ala Phe Lys Ala Asp Val Asp His
                85                  90                  95
Phe Val Leu Trp Phe Val Tyr Leu Phe Ile Gly Lys Phe Val Leu Thr
            100                 105                 110
Tyr Val Ser Thr Ala Ala Ile Thr Ile Ser Ala Ile Arg Thr Thr Arg
            115                 120                 125
Thr Leu Arg Arg Val Phe Leu Glu Cys Thr Leu Arg Gln Glu Val Trp
    130                 135                 140
His Phe Asp Lys Gln Ser Asn Gly Ala Ile Ala Thr Gln Val Thr Thr
145                 150                 155                 160
Asn Gly Asn Arg Ile Gln Thr Gly Ile Ala Glu Lys Leu Val Phe Thr
                165                 170                 175
Val Gln Ala Leu Ser Met Phe Phe Ser Ala Phe Val Val Ala Leu Ala
            180                 185                 190
Ser Gln Trp Lys Leu Ala Leu Ile Thr Met Ser Val Ile Pro Ala Ile
            195                 200                 205
Phe Leu Val Thr Gly Ile Cys Ile Ala Ile Asp Ala Ala Gln Glu Ala
    210                 215                 220
Arg Ile Thr Arg Ile Tyr Ser Arg Ala Ala Val Leu Ala Glu Glu Val
225                 230                 235                 240
Leu Ser Ser Ile Arg Thr Val His Ala Phe Tyr Ala Gln Lys Lys Met
                245                 250                 255
Val Glu Lys Tyr Asp Val Phe Leu Gln Gln Ala His Gln Glu Gly Lys
            260                 265                 270
Lys Lys Ser Pro Asn Asn Xaa Val Leu Phe Ser Thr Glu Tyr Phe Cys
            275                 280                 285
Ile Tyr Ala Ala Ile Ala Leu Ala Phe Trp Lys Gly Phe Arg Met Tyr
    290                 295                 300
Gln Asn Gly Glu Val Ala Asp Val Gly Lys Val Phe Thr Val Val Leu
305                 310                 315                 320
Ser Val Thr Leu Ala Ala Thr Ser Ile Ser Met Leu Ala Pro Ser Gly
                325                 330                 335
Ser Val Val Tyr Gln Arg Arg Ile Phe Gly Ser Glu Leu Phe Ser Ile
            340                 345                 350
Ile Asp Lys Pro Thr Gln Leu Asp Pro Leu Asp Pro Ser Gly Lys Gln
            355                 360                 365
Pro Glu Gly Cys Leu Gly Gln Ile Glu Ile Gln Asn Leu Ala Phe Ala
    370                 375                 380
Tyr Pro Ser Arg Pro Ser Ala Gln Val Leu Arg Asp Phe Asn Leu Thr
385                 390                 395                 400
Ile Pro Ala Gly Lys Thr Thr Ala Leu Val Gly Ala Ser Gly Ser Gly
                405                 410                 415
Lys Ser Thr Met Val Gly Leu Leu Glu Arg Trp Tyr Leu Pro Ser Ser
            420                 425                 430
Gly Arg Ile Leu Leu Asp Gly Leu Glu Leu Gly Gln Tyr Asn Val Lys
    435                 440                 445
Trp Leu Arg Ser Arg Ile Arg Leu Val Gln Gln Glu Pro Val Leu Phe
    450                 455                 460
Arg Gly Thr Ile Phe Gln Asn Ile Ala Asn Gly Phe Met Asp Glu Gln
465                 470                 475                 480
Arg Asp Leu Pro Arg Glu Lys Gln Met Glu Leu Val Gln Lys Ala Cys
                485                 490                 495
```

-continued

```
Lys Ala Ser Asn Gly Asp Val Phe Ile Asn Glu Leu Pro Asn Gly Tyr
            500                 505                 510

Glu Thr Glu Val Gly Glu Arg Ala Gly Ala Leu Ser Gly Gly Gln Arg
        515                 520                 525

Gln Arg Ile Ala Ile Ala Arg Ser Ile Ile Ser Asp Pro Lys Ile Leu
    530                 535                 540

Leu Leu Asp Glu Ala Thr Ser Ala Leu Asp Pro Lys Ala Glu Lys Val
545                 550                 555                 560

Val Gln Glu Ala Leu Asn Arg Val Ser Lys Asp Arg Thr Thr Leu Val
                565                 570                 575

Ile Ala His Lys Leu Ala Thr Val Lys Ser Ala Gly Asn Ile Ala Val
            580                 585                 590

Ile Ser Gln Gly Lys Ile Val Glu Gln Gly Thr His His Glu Leu Ile
        595                 600                 605

Glu Phe Gly Cys His Tyr Ala Ala Leu Val Arg Ala Gln Asp Leu Gly
    610                 615                 620

Ala Asp Glu Gln Gln Glu His Glu Lys Thr Leu His Glu Lys Ala Ala
625                 630                 635                 640

Arg Glu Ala Ala Gly Glu Arg Pro Ala Leu Glu Arg Thr His Thr Thr
                645                 650                 655

Ala Thr Ser Gln Ala Gly Asp Leu Glu Lys Arg Lys Val Pro Val Gly
            660                 665                 670

Thr Leu Gly Tyr Ser Leu Leu Lys Cys Ile Leu Ile Met Phe Tyr Glu
        675                 680                 685

Gln Lys Asn Leu Tyr Trp Cys Phe Leu Leu Ser Thr Ile Thr Val Leu
    690                 695                 700

Ile Cys Ala Ala Thr Phe Pro Gly Gln Ala Leu Leu Phe Ser Arg Leu
705                 710                 715                 720

Leu Thr Val Phe Glu Leu Ser Gly His Ala Ala Gln Glu Arg Ala Asp
                725                 730                 735

Phe Tyr Ile Leu Met Phe Phe Val Ala Leu Gly Asn Leu Val Gly
            740                 745                 750

Tyr Phe Thr Ile Gly Trp Thr Cys Asn Val Ile Ser Gln Val Val Thr
        755                 760                 765

His Arg Tyr Gln Ala Ala Met Phe Gln Arg Val Leu Asp Gln Asp Ile
    770                 775                 780

Glu Leu Leu Asp Ile Pro Glu Gln Ile Ser Gly Ala Leu Thr Ser Gln
785                 790                 795                 800

Leu Ser Ala Leu Pro Thr Gln Leu Gln Glu Leu Ile Ser Ala Asn Phe
                805                 810                 815

Leu Ile Tyr Ile Val Val Gly Gln His Arg Leu Glu Gln Cys Ser Thr
            820                 825                 830

Thr Ser Leu Trp Met Glu Thr Gly Pro Gly Gly Cys Val Trp Cys Thr
        835                 840                 845

Ser Thr Pro Ala Phe Gly Trp Leu Pro Gln Asn Ser Ser Arg Asp Glu
    850                 855                 860

Ala Arg Ser Arg Lys Leu Gly Lys Leu Cys Arg Lys Cys Trp Ala Cys
865                 870                 875                 880

Lys Arg Ser Ser Tyr Arg Asp Pro Asp Arg Leu Ile Phe Asp Ser Arg
                885                 890                 895

Arg Pro Cys Ser Pro Thr Val Leu Gly His Val Glu Gln Gly Leu Ala
            900                 905                 910

Lys Ile Ile Gln Ser Phe Trp Phe Gly Arg Cys Phe Gly Phe His Leu
```

-continued

```
               915                 920                 925
Ser Gln Ser Met Glu Phe Leu Ala Ile Ala Leu Gly Phe Cys Ile Ala
    930                 935                 940
Val Asp Asn Trp Leu Gln Val Ser Thr Thr Gln Leu Asn Phe Ile Ser
945                 950                 955                 960
Ser Ser Trp Ala Phe Cys Leu Pro Val Gln Ala Ala Gln Tyr Leu
                965                 970                 975
Ala Tyr Ser Thr Ser Phe Thr Lys Ala Arg Ser Ala Ala Asn Tyr Ile
                980                 985                 990
Leu Trp Leu Arg Thr Leu Lys Pro Thr Ile Arg Glu Thr Glu Asn
                995                1000                1005
Lys Lys Lys Gly Pro Val Gly Gly Cys Pro Val Asp Leu Glu Asp Ile
   1010                1015                1020
Glu Phe Arg Tyr Arg Gln Arg Asp Ser Ala Arg Val Leu Arg Gly Val
1025                1030                1035                1040
Ser Met Thr Ile Glu Pro Gly Gln Phe Val Ala Tyr Val Gly Ala Ser
                1045                1050                1055
Gly Cys Gly Lys Ser Thr Leu Ile Ala Leu Ser Glu Arg Phe Tyr Asp
                1060                1065                1070
Pro Thr Ser Gly Arg Ile Ser Phe Ala His Glu Asn Ile Ala Glu Met
                1075                1080                1085
Ser Pro Arg Leu Tyr Arg Gly His Met Ser Leu Val Gln Gln Glu Pro
   1090                1095                1100
Thr Leu Tyr Gln Gly Ser Val Arg Glu Asn Val Thr Leu Ala Leu Glu
1105                1110                1115                1120
Ala Glu Leu Ser Glu Glu Leu Cys Gln Gly Arg Leu Pro Ala Arg Pro
                1125                1130                1135
Met Leu Trp Ile Leu Ser Ser Leu Tyr Gln Lys Ala Leu Lys Arg Leu
                1140                1145                1150
Ala Ala Gln Arg Gly Met Gln Phe Ser Gly Gly Gln Arg Gln Arg Ile
                1155                1160                1165
Ala Ile Ala Arg Ala Leu Ile Arg Asn Pro Lys Leu Leu Leu Leu Asp
   1170                1175                1180
Glu Ala Thr Ser Ala Leu Asp Thr Gln Ser Glu Arg Leu Val Gln Ala
1185                1190                1195                1200
Ala Leu Asp Glu Ala Ser Thr Ser Arg Thr Thr Ile Ala Val Ala His
                1205                1210                1215
Arg Leu Ser Thr Ile Arg Asn Val Asp Val Ile Phe Val Phe Ala Asn
                1220                1225                1230
Gly Arg Ile Ala Glu Thr Gly Thr His Ala Glu Leu Gln Arg Leu Arg
                1235                1240                1245
Gly Arg Tyr Tyr Glu Met Cys Leu Ala Gln Ser Leu Asp Gln Ala
                1250                1255                1260

<210> SEQ ID NO 12
<211> LENGTH: 1937
<212> TYPE: DNA
<213> ORGANISM: Exophiala spinifera
<220> FEATURE:
<221> NAME/KEY: CDS
<222> LOCATION: (153)...(1736)

<400> SEQUENCE: 12
gcggatccgt tttttttttt tttttccta agttcgacta cccacttgct agtctcacag      60
tagctccaag ggtataagtt cgactcgaag ctgcatctct ccgtgaaaca tggcaatagt     120
```

-continued

```
ttttgtagac agatccatca accgagtaca cg atg ccg tca agg tac att ctc      173
                                    Met Pro Ser Arg Tyr Ile Leu
                                    1               5 tct tgg ctc ctc acc tgc ttt ttg ggc att gct ttt ggc tca cga tgc      221
Ser Trp Leu Leu Thr Cys Phe Leu Gly Ile Ala Phe Gly Ser Arg Cys
        10              15              20 ggg tcg tct gct cct act gtc aag att gat gct ggg atg gtg gtc ggc      269
Gly Ser Ser Ala Pro Thr Val Lys Ile Asp Ala Gly Met Val Val Gly
25              30              35 acg act act act gtc ccc ggc act act gcg acc gtc agc gag ttc ttg      317
Thr Thr Thr Thr Val Pro Gly Thr Thr Ala Thr Val Ser Glu Phe Leu
40              45              50              55 ggc gtt cct ttt gcc gcc tct ccg aca cga ttt gcg cct cct act cgt      365
Gly Val Pro Phe Ala Ala Ser Pro Thr Arg Phe Ala Pro Pro Thr Arg
            60              65              70 ccc gtg cct tgg tca acg cct ttg caa gcc act gca tat ggt cca gca      413
Pro Val Pro Trp Ser Thr Pro Leu Gln Ala Thr Ala Tyr Gly Pro Ala
        75              80              85 tgc cct caa caa ttc aat tac ccc gaa gaa ctc cgt gag att acg atg      461
Cys Pro Gln Gln Phe Asn Tyr Pro Glu Glu Leu Arg Glu Ile Thr Met
        90              95              100 gcc tgg ttc aat aca ccg ccc ccg tca gct ggt gaa agt gag gac tgc      509
Ala Trp Phe Asn Thr Pro Pro Pro Ser Ala Gly Glu Ser Glu Asp Cys
105             110             115 ctg aac ctc aac atc tac gtc cca gga act gag aac aca aac aaa gcc      557
Leu Asn Leu Asn Ile Tyr Val Pro Gly Thr Glu Asn Thr Asn Lys Ala
120             125             130             135 gtc atg gtt tgg ata tac ggt gga gcg ctg gaa tat ggt tgg aat tca      605
Val Met Val Trp Ile Tyr Gly Gly Ala Leu Glu Tyr Gly Trp Asn Ser
                140             145             150 ttc cac ctt tac gac ggg gct agt ttc gca gcc aat cag gat gtc atc      653
Phe His Leu Tyr Asp Gly Ala Ser Phe Ala Ala Asn Gln Asp Val Ile
            155             160             165 gtc gtg acc atc aac tac aga acg aac att ctg ggg ttc cct gct gcc      701
Val Val Thr Ile Asn Tyr Arg Thr Asn Ile Leu Gly Phe Pro Ala Ala
        170             175             180 cct cag ctt cca ata aca cag cga aat ctg ggg ttc cta gac caa agg      749
Pro Gln Leu Pro Ile Thr Gln Arg Asn Leu Gly Phe Leu Asp Gln Arg
185             190             195 ttt gct ttg gat tgg gta cag cgg aac atc gca gcc ttt ggc ggt gat      797
Phe Ala Leu Asp Trp Val Gln Arg Asn Ile Ala Ala Phe Gly Gly Asp
200             205             210             215 cct cga aag gtc aca ata ttt ggg cag agt gcg ggg ggc aga agt gtc      845
Pro Arg Lys Val Thr Ile Phe Gly Gln Ser Ala Gly Gly Arg Ser Val
                220             225             230 gac gtc ctc ttg acg tct atg cca cac aac cca ccc ttc cga gca gca      893
Asp Val Leu Leu Thr Ser Met Pro His Asn Pro Pro Phe Arg Ala Ala
            235             240             245 atc atg gag tcc ggt gtg gct aac tac aac ttc ccc aag gga gat ttg      941
Ile Met Glu Ser Gly Val Ala Asn Tyr Asn Phe Pro Lys Gly Asp Leu
        250             255             260 tcc gaa cct tgg aac acc act gtt caa gct ctc aac tgt acc acc agt      989
Ser Glu Pro Trp Asn Thr Thr Val Gln Ala Leu Asn Cys Thr Thr Ser
265             270             275 atc gac atc ttg agt tgt atg aga aga gtc gat ctc gcc act ctg atg     1037
Ile Asp Ile Leu Ser Cys Met Arg Arg Val Asp Leu Ala Thr Leu Met
280             285             290             295 aac acg atc gag caa ctc gga ctt ggg ttt gag tac acg ttg gac aac     1085
Asn Thr Ile Glu Gln Leu Gly Leu Gly Phe Glu Tyr Thr Leu Asp Asn
                300             305             310 gta acg gtt gtg tac cgt tct gaa acg gct cgc acg act ggt gac att     1133
Val Thr Val Val Tyr Arg Ser Glu Thr Ala Arg Thr Thr Gly Asp Ile
```

```
                    315                 320                 325
gct cgt gta cct gtt ctc gtc ggg acg gtg gcc aac gac gga ctt ctc      1181
Ala Arg Val Pro Val Leu Val Gly Thr Val Ala Asn Asp Gly Leu Leu
        330                 335                 340 ttt gtc ctc ggg gag aat gac acc caa gca tat ctc gag gag gca atc      1229
Phe Val Leu Gly Glu Asn Asp Thr Gln Ala Tyr Leu Glu Glu Ala Ile
    345                 350                 355 ccg aat cag ccc gac ctt tac cag act ctc ctt gga gca tat ccc att      1277
Pro Asn Gln Pro Asp Leu Tyr Gln Thr Leu Leu Gly Ala Tyr Pro Ile
360                 365                 370                 375 gga tcc cca ggg atc gga tcg cct caa gat cag att gcc gcc att gag      1325
Gly Ser Pro Gly Ile Gly Ser Pro Gln Asp Gln Ile Ala Ala Ile Glu
                380                 385                 390 acc gag gta aga ttc cag tgt cct tct gcc atc gtg gct cag gac tcc      1373
Thr Glu Val Arg Phe Gln Cys Pro Ser Ala Ile Val Ala Gln Asp Ser
            395                 400                 405 cgg aat cgg ggt atc cct tct tgg cgc tac tac tac aat gcg acc ttt      1421
Arg Asn Arg Gly Ile Pro Ser Trp Arg Tyr Tyr Tyr Asn Ala Thr Phe
        410                 415                 420 gag aat ctg gag ctt ttc cct ggg tcc gaa gtg tac cac agc tct gaa      1469
Glu Asn Leu Glu Leu Phe Pro Gly Ser Glu Val Tyr His Ser Ser Glu
    425                 430                 435 gtc ggg atg gtg ttt ggc acg tat cct gtc gca agt gcg acc gcc ttg      1517
Val Gly Met Val Phe Gly Thr Tyr Pro Val Ala Ser Ala Thr Ala Leu
440                 445                 450                 455 gag gcc cag acg agc aaa tac atg cag ggt gcc tgg gcg gcc ttt gcc      1565
Glu Ala Gln Thr Ser Lys Tyr Met Gln Gly Ala Trp Ala Ala Phe Ala
                460                 465                 470 aaa aac ccc atg aat ggg cct ggg tgg aaa caa gtg ccg aat gtc gcg      1613
Lys Asn Pro Met Asn Gly Pro Gly Trp Lys Gln Val Pro Asn Val Ala
            475                 480                 485 gcg ctt ggc tca cca ggc aaa gcc atc cag gtt gac gtc tct cca gcg      1661
Ala Leu Gly Ser Pro Gly Lys Ala Ile Gln Val Asp Val Ser Pro Ala
        490                 495                 500 aca ata gac caa cga tgt gcc ttg tac acg cat tat tat act gag ttg      1709
Thr Ile Asp Gln Arg Cys Ala Leu Tyr Thr His Tyr Tyr Thr Glu Leu
    505                 510                 515 ggc aca atc gcg ccg agg aca ttt tga ggaccaggt attgtaccta             1756
Gly Thr Ile Ala Pro Arg Thr Phe *
520                 525 cagcgggttc ggaaaaggag gtatctgctg tcaatttgcc gccagccatc attgaagagt    1816
gctgaaattt catggggaa tatccatcca tgctcacatt agcgcttttg gaagatggac     1876
tgttagcgag tcttgggcgg tttcaggctt ttccccccc aaaaaaaaaa aaaaaaaaa      1936 a                                                                    1937

<210> SEQ ID NO 13
<211> LENGTH: 527
<212> TYPE: PRT
<213> ORGANISM: Exophiala spinifera

<400> SEQUENCE: 13

Met Pro Ser Arg Tyr Ile Leu Ser Trp Leu Leu Thr Cys Phe Leu Gly
 1               5                  10                  15

Ile Ala Phe Gly Ser Arg Cys Gly Ser Ser Ala Pro Thr Val Lys Ile
                20                  25                  30

Asp Ala Gly Met Val Val Gly Thr Thr Thr Thr Val Pro Gly Thr Thr
            35                  40                  45
```

```
Ala Thr Val Ser Glu Phe Leu Gly Val Pro Phe Ala Ala Ser Pro Thr
 50                  55                  60

Arg Phe Ala Pro Pro Thr Arg Pro Val Pro Trp Ser Thr Pro Leu Gln
 65                  70                  75                  80

Ala Thr Ala Tyr Gly Pro Ala Cys Pro Gln Gln Phe Asn Tyr Pro Glu
                 85                  90                  95

Glu Leu Arg Glu Ile Thr Met Ala Trp Phe Asn Thr Pro Pro Pro Ser
            100                 105                 110

Ala Gly Glu Ser Glu Asp Cys Leu Asn Leu Asn Ile Tyr Val Pro Gly
            115                 120                 125

Thr Glu Asn Thr Asn Lys Ala Val Met Val Trp Ile Tyr Gly Gly Ala
    130                 135                 140

Leu Glu Tyr Gly Trp Asn Ser Phe His Leu Tyr Asp Gly Ala Ser Phe
145                 150                 155                 160

Ala Ala Asn Gln Asp Val Ile Val Thr Ile Asn Tyr Arg Thr Asn
                165                 170                 175

Ile Leu Gly Phe Pro Ala Ala Pro Gln Leu Pro Ile Thr Gln Arg Asn
            180                 185                 190

Leu Gly Phe Leu Asp Gln Arg Phe Ala Leu Asp Trp Val Gln Arg Asn
            195                 200                 205

Ile Ala Ala Phe Gly Gly Asp Pro Arg Lys Val Thr Ile Phe Gly Gln
210                 215                 220

Ser Ala Gly Gly Arg Ser Val Asp Val Leu Leu Thr Ser Met Pro His
225                 230                 235                 240

Asn Pro Pro Phe Arg Ala Ala Ile Met Glu Ser Gly Val Ala Asn Tyr
                245                 250                 255

Asn Phe Pro Lys Gly Asp Leu Ser Glu Pro Trp Asn Thr Thr Val Gln
            260                 265                 270

Ala Leu Asn Cys Thr Thr Ser Ile Asp Ile Leu Ser Cys Met Arg Arg
            275                 280                 285

Val Asp Leu Ala Thr Leu Met Asn Thr Ile Glu Gln Leu Gly Leu Gly
    290                 295                 300

Phe Glu Tyr Thr Leu Asp Asn Val Thr Val Val Tyr Arg Ser Glu Thr
305                 310                 315                 320

Ala Arg Thr Thr Gly Asp Ile Ala Arg Val Pro Val Leu Val Gly Thr
                325                 330                 335

Val Ala Asn Asp Gly Leu Leu Phe Val Leu Gly Glu Asn Asp Thr Gln
            340                 345                 350

Ala Tyr Leu Glu Glu Ala Ile Pro Asn Gln Pro Asp Leu Tyr Gln Thr
            355                 360                 365

Leu Leu Gly Ala Tyr Pro Ile Gly Ser Pro Gly Ile Gly Ser Pro Gln
    370                 375                 380

Asp Gln Ile Ala Ala Ile Glu Thr Glu Val Arg Phe Gln Cys Pro Ser
385                 390                 395                 400

Ala Ile Val Ala Gln Asp Ser Arg Asn Arg Gly Ile Pro Ser Trp Arg
                405                 410                 415

Tyr Tyr Tyr Asn Ala Thr Phe Glu Asn Leu Glu Leu Phe Pro Gly Ser
            420                 425                 430

Glu Val Tyr His Ser Ser Glu Val Gly Met Val Phe Gly Thr Tyr Pro
            435                 440                 445

Val Ala Ser Ala Thr Ala Leu Glu Ala Gln Thr Ser Lys Tyr Met Gln
    450                 455                 460

Gly Ala Trp Ala Ala Phe Ala Lys Asn Pro Met Asn Gly Pro Gly Trp
```

-continued

```
        465                 470                 475                 480
Lys Gln Val Pro Asn Val Ala Ala Leu Gly Ser Pro Gly Lys Ala Ile
                485                 490                 495

Gln Val Asp Val Ser Pro Ala Thr Ile Asp Gln Arg Cys Ala Leu Tyr
            500                 505                 510

Thr His Tyr Tyr Thr Glu Leu Gly Thr Ile Ala Pro Arg Thr Phe
        515                 520                 525

<210> SEQ ID NO 14
<211> LENGTH: 1800
<212> TYPE: DNA
<213> ORGANISM: Bacterium of ATCC 55552
<220> FEATURE:
<221> NAME/KEY: CDS
<222> LOCATION: (94)...(1683)

<400> SEQUENCE: 14
actagtggat cattgcattg ctggcggac tggcgcgccg atagtcgttg cgatggtcgc      60
gagaataagc gtgcgaagtg ggaggatgtg aag atg ggg gcc agg agt atg tgt    114
                                    Met Gly Ala Arg Ser Met Cys
                                      1               5 gcg gga cgg ttc gga cgc ttc tgc att ggc ttg gct tca tcg gtt gcc    162
Ala Gly Arg Phe Gly Arg Phe Cys Ile Gly Leu Ala Ser Ser Val Ala
         10                  15                  20 gtg act cta ggg gga gcc tcc gcc gcc ggc gcg gca acc gcg acg gat    210
Val Thr Leu Gly Gly Ala Ser Ala Ala Gly Ala Ala Thr Ala Thr Asp
     25                  30                  35 ttt ccg gtc cgc agg acc gat ctg ggc cag gtt cag gga ctg gcc ggg    258
Phe Pro Val Arg Arg Thr Asp Leu Gly Gln Val Gln Gly Leu Ala Gly
 40                  45                  50                  55 gac gtg atg agc ttt cgc gga ata ccc tat gca gcg ccg ccg gtg ggc    306
Asp Val Met Ser Phe Arg Gly Ile Pro Tyr Ala Ala Pro Pro Val Gly
                 60                  65                  70 ggg ctg cgt tgg aag ccg ccc caa cac gcc cgg ccc tgg gcg ggc gtt    354
Gly Leu Arg Trp Lys Pro Pro Gln His Ala Arg Pro Trp Ala Gly Val
             75                  80                  85 cgc ccc gcc acc caa ttt ggc tcc gac tgc ttc ggc gcg gcc tat ctt    402
Arg Pro Ala Thr Gln Phe Gly Ser Asp Cys Phe Gly Ala Ala Tyr Leu
         90                  95                 100 cgc aaa ggc agc ctc gcc ccc ggc gtg agc gag gac tgt ctt tac ctc    450
Arg Lys Gly Ser Leu Ala Pro Gly Val Ser Glu Asp Cys Leu Tyr Leu
    105                 110                 115 aac gta tgg gcg ccg tca ggc gct aaa ccc ggc cag tac ccc gtc atg    498
Asn Val Trp Ala Pro Ser Gly Ala Lys Pro Gly Gln Tyr Pro Val Met
120                 125                 130                 135 gtc tgg gtc tac ggc ggc ggc ttc gcc ggc ggc acg gcc gcc atg ccc    546
Val Trp Val Tyr Gly Gly Gly Phe Ala Gly Gly Thr Ala Ala Met Pro
                140                 145                 150 tac tac gac ggc gag gcg ctt gcg cga cag ggc gtc gtc gtg gtg acg    594
Tyr Tyr Asp Gly Glu Ala Leu Ala Arg Gln Gly Val Val Val Val Thr
            155                 160                 165 ttt aac tat cgg acg aac atc ctg ggc ttt ttc gcc cat cct ggt ctc    642
Phe Asn Tyr Arg Thr Asn Ile Leu Gly Phe Phe Ala His Pro Gly Leu
        170                 175                 180 tcg cgc gag agc ccc acc gga act tcg ggc aac tac ggc cta ctc gac    690
Ser Arg Glu Ser Pro Thr Gly Thr Ser Gly Asn Tyr Gly Leu Leu Asp
    185                 190                 195 att ctc gcc gct ctt cgg tgg gtg cag agc aac gcc cgc gcc ttc gga    738
Ile Leu Ala Ala Leu Arg Trp Val Gln Ser Asn Ala Arg Ala Phe Gly
```

```
                200                 205                 210                 215
ggg gac ccc ggc cga gtg acg gtc ttt ggt gaa tcg gcc gga gcg agc        786
Gly Asp Pro Gly Arg Val Thr Val Phe Gly Glu Ser Ala Gly Ala Ser
                        220                 225                 230 gcg atc gga ctt ctg ctc acc tcg ccg ctg agc aag ggt ctc ttc cgt        834
Ala Ile Gly Leu Leu Leu Thr Ser Pro Leu Ser Lys Gly Leu Phe Arg
                235                 240                 245 ggc gct atc ctc gaa agt cca ggg ctg acg cga ccg ctc gcg acg ctc        882
Gly Ala Ile Leu Glu Ser Pro Gly Leu Thr Arg Pro Leu Ala Thr Leu
            250                 255                 260 gcc gac agc gcc gcc tcg ggc gag cgc ctc gac gcc gat ctt tcg cga        930
Ala Asp Ser Ala Ala Ser Gly Glu Arg Leu Asp Ala Asp Leu Ser Arg
        265                 270                 275 ctg cgc tcg acc gac cca gcc acc ctg atg gcg cgc gcc gac gcg gcc        978
Leu Arg Ser Thr Asp Pro Ala Thr Leu Met Ala Arg Ala Asp Ala Ala
280                 285                 290                 295 cgc ccg gca tcg cgg gac ctg cgc agg ccg cgt ccg acc gga ccg atc       1026
Arg Pro Ala Ser Arg Asp Leu Arg Arg Pro Arg Pro Thr Gly Pro Ile
                        300                 305                 310 gtc gat ggc cat gtg ctg ccg cag acc gac agc gcg gcg atc gcg gcg       1074
Val Asp Gly His Val Leu Pro Gln Thr Asp Ser Ala Ala Ile Ala Ala
                315                 320                 325 ggg cag ctg gcg ccg gtt cgg gtc ctg atc gga acc aat gcc gac gaa       1122
Gly Gln Leu Ala Pro Val Arg Val Leu Ile Gly Thr Asn Ala Asp Glu
            330                 335                 340 ggc cgc gcc ttc ctc ggg cgc gcg ccg atg gag acg cca gcg gac tac       1170
Gly Arg Ala Phe Leu Gly Arg Ala Pro Met Glu Thr Pro Ala Asp Tyr
        345                 350                 355 caa gcc tat ctg gag gcg cag ttt ggc gac caa gcc gcc gcc gtg gcg       1218
Gln Ala Tyr Leu Glu Ala Gln Phe Gly Asp Gln Ala Ala Ala Val Ala
360                 365                 370                 375 gcg tgc tat ccc ctc gac ggc cgg gcc acg ccc aag gaa atg gtc gcg       1266
Ala Cys Tyr Pro Leu Asp Gly Arg Ala Thr Pro Lys Glu Met Val Ala
                        380                 385                 390 cgc atc ttc ggc gac aat cag ttc aat cgg ggg gtc tcg gcc ttc tcg       1314
Arg Ile Phe Gly Asp Asn Gln Phe Asn Arg Gly Val Ser Ala Phe Ser
                395                 400                 405 gaa gcg ctt gtg cgc cag ggc gcg ccc gtg tgg cgt tat cag ttc aac       1362
Glu Ala Leu Val Arg Gln Gly Ala Pro Val Trp Arg Tyr Gln Phe Asn
            410                 415                 420 ggt aat acc gag ggt gga aga gcg ccg gct acc cac gga gcc gaa att       1410
Gly Asn Thr Glu Gly Gly Arg Ala Pro Ala Thr His Gly Ala Glu Ile
        425                 430                 435 ccc tac gtt ttc ggg gtg ttc aag ctc gac gag ttg ggt ctg ttc gat       1458
Pro Tyr Val Phe Gly Val Phe Lys Leu Asp Glu Leu Gly Leu Phe Asp
440                 445                 450                 455 tgg ccg ccc gag ggg ccc acg ccc gcc gac cgt gcg ctg ggc caa ctg       1506
Trp Pro Pro Glu Gly Pro Thr Pro Ala Asp Arg Ala Leu Gly Gln Leu
                        460                 465                 470 atg tcc tcc gcc tgg gtc cgg ttc gcc aag aat ggc gac ccc gcc ggg       1554
Met Ser Ser Ala Trp Val Arg Phe Ala Lys Asn Gly Asp Pro Ala Gly
                475                 480                 485 gac gcc ctt acc tgg cct gcc tat tct acg ggc aag tcg acc atg aca       1602
Asp Ala Leu Thr Trp Pro Ala Tyr Ser Thr Gly Lys Ser Thr Met Thr
            490                 495                 500 ttc ggt ccc gag ggc cgc gcg gcg gtg gtg tcg ccc gga cct tcc atc       1650
Phe Gly Pro Glu Gly Arg Ala Ala Val Val Ser Pro Gly Pro Ser Ile
        505                 510                 515 ccc cct tgc gcg gat ggc gcc aag gcg ggg tga cgccgtcgac gatggcgtga    1703
```

-continued

```
Pro Pro Cys Ala Asp Gly Ala Lys Ala Gly     *
520                 525 cgacggtcga ggcgatgttc tcgatctgga gtccgcgccg cctcgatttg cgtcgtctcc    1763
ggcgctcaga cgaacgcccc agttccatcc acacagt                             1800

<210> SEQ ID NO 15
<211> LENGTH: 529
<212> TYPE: PRT
<213> ORGANISM: Bacterium of ATCC 55552

<400> SEQUENCE: 15

Met Gly Ala Arg Ser Met Cys Ala Gly Arg Phe Gly Arg Phe Cys Ile
1               5                   10                  15

Gly Leu Ala Ser Ser Val Ala Val Thr Leu Gly Gly Ala Ser Ala Ala
                20                  25                  30

Gly Ala Ala Thr Ala Thr Asp Phe Pro Val Arg Arg Thr Asp Leu Gly
            35                  40                  45

Gln Val Gln Gly Leu Ala Gly Asp Val Met Ser Phe Arg Gly Ile Pro
        50                  55                  60

Tyr Ala Ala Pro Pro Val Gly Leu Arg Trp Lys Pro Pro Gln His
65                  70                  75                  80

Ala Arg Pro Trp Ala Gly Val Arg Pro Ala Thr Gln Phe Gly Ser Asp
                85                  90                  95

Cys Phe Gly Ala Ala Tyr Leu Arg Lys Gly Ser Leu Ala Pro Gly Val
            100                 105                 110

Ser Glu Asp Cys Leu Tyr Leu Asn Val Trp Ala Pro Ser Gly Ala Lys
        115                 120                 125

Pro Gly Gln Tyr Pro Val Met Val Trp Val Tyr Gly Gly Gly Phe Ala
    130                 135                 140

Gly Gly Thr Ala Ala Met Pro Tyr Tyr Asp Gly Glu Ala Leu Ala Arg
145                 150                 155                 160

Gln Gly Val Val Val Thr Phe Asn Tyr Arg Thr Asn Ile Leu Gly
                165                 170                 175

Phe Phe Ala His Pro Gly Leu Ser Arg Glu Ser Pro Thr Gly Thr Ser
            180                 185                 190

Gly Asn Tyr Gly Leu Leu Asp Ile Leu Ala Ala Leu Arg Trp Val Gln
        195                 200                 205

Ser Asn Ala Arg Ala Phe Gly Gly Asp Pro Gly Arg Val Thr Val Phe
    210                 215                 220

Gly Glu Ser Ala Gly Ala Ser Ala Ile Gly Leu Leu Thr Ser Pro
225                 230                 235                 240

Leu Ser Lys Gly Leu Phe Arg Gly Ala Ile Leu Glu Ser Pro Gly Leu
                245                 250                 255

Thr Arg Pro Leu Ala Thr Leu Ala Asp Ser Ala Ala Ser Gly Glu Arg
            260                 265                 270

Leu Asp Ala Asp Leu Ser Arg Leu Arg Ser Thr Asp Pro Ala Thr Leu
        275                 280                 285

Met Ala Arg Ala Asp Ala Arg Pro Ala Ser Arg Asp Leu Arg Arg
    290                 295                 300

Pro Arg Pro Thr Gly Pro Ile Val Asp Gly His Val Leu Pro Gln Thr
305                 310                 315                 320

Asp Ser Ala Ala Ile Ala Ala Gly Gln Leu Ala Pro Val Arg Val Leu
                325                 330                 335

Ile Gly Thr Asn Ala Asp Glu Gly Arg Ala Phe Leu Gly Arg Ala Pro
```

-continued

```
                   340                 345                 350
    Met Glu Thr Pro Ala Asp Tyr Gln Ala Tyr Leu Glu Ala Gln Phe Gly
            355                 360                 365

Asp Gln Ala Ala Ala Val Ala Ala Cys Tyr Pro Leu Asp Gly Arg Ala
            370                 375                 380

Thr Pro Lys Glu Met Val Ala Arg Ile Phe Gly Asp Asn Gln Phe Asn
    385                 390                 395                 400

Arg Gly Val Ser Ala Phe Ser Glu Ala Leu Val Arg Gln Gly Ala Pro
                    405                 410                 415

Val Trp Arg Tyr Gln Phe Asn Gly Asn Thr Glu Gly Gly Arg Ala Pro
            420                 425                 430

Ala Thr His Gly Ala Glu Ile Pro Tyr Val Phe Gly Val Phe Lys Leu
            435                 440                 445

Asp Glu Leu Gly Leu Phe Asp Trp Pro Pro Glu Gly Pro Thr Pro Ala
            450                 455                 460

Asp Arg Ala Leu Gly Gln Leu Met Ser Ser Ala Trp Val Arg Phe Ala
    465                 470                 475                 480

Lys Asn Gly Asp Pro Ala Gly Asp Ala Leu Thr Trp Pro Ala Tyr Ser
                    485                 490                 495

Thr Gly Lys Ser Thr Met Thr Phe Gly Pro Glu Gly Arg Ala Ala Val
                500                 505                 510

Val Ser Pro Gly Pro Ser Ile Pro Pro Cys Ala Asp Gly Ala Lys Ala
            515                 520                 525

Gly
```

<210> SEQ ID NO 16
<211> LENGTH: 1389
<212> TYPE: DNA
<213> ORGANISM: Exophiala spinifera
<220> FEATURE:
<221> NAME/KEY: CDS
<222> LOCATION: (1)...(1389)
<220> FEATURE:
<221> NAME/KEY: misc_feature
<222> LOCATION: (0)...(0)
<223> OTHER INFORMATION: truncated APAO

<400> SEQUENCE: 16

```
gac aac gtt gcg gac gtg gta gtg gtg ggc gct ggc ttg agc ggt ttg      48
Asp Asn Val Ala Asp Val Val Val Val Gly Ala Gly Leu Ser Gly Leu
  1               5                  10                  15 gag acg gca cgc aaa gtc cag gcc gcc ggt ctg tcc tgc ctc gtt ctt      96
Glu Thr Ala Arg Lys Val Gln Ala Ala Gly Leu Ser Cys Leu Val Leu
             20                  25                  30 gag gcg atg gat cgt gta ggg gga aag act ctg agc gta caa tcg ggt     144
Glu Ala Met Asp Arg Val Gly Gly Lys Thr Leu Ser Val Gln Ser Gly
         35                  40                  45 ccc ggc agg acg act atc aac gac ctc ggc gct gcg tgg atc aat gac     192
Pro Gly Arg Thr Thr Ile Asn Asp Leu Gly Ala Ala Trp Ile Asn Asp
     50                  55                  60 agc aac caa agc gaa gta tcc aga ttg ttt gaa aga ttt cat ttg gag     240
Ser Asn Gln Ser Glu Val Ser Arg Leu Phe Glu Arg Phe His Leu Glu
 65                  70                  75                  80 ggc gag ctc cag agg acg act gga aat tca atc cat caa gca caa gac     288
Gly Glu Leu Gln Arg Thr Thr Gly Asn Ser Ile His Gln Ala Gln Asp
                 85                  90                  95 ggt aca acc act aca gct cct tat ggt gac tcc ttg ctg agc gag gag     336
Gly Thr Thr Thr Thr Ala Pro Tyr Gly Asp Ser Leu Leu Ser Glu Glu
            100                 105                 110
```

-continued

| | |
|---|---|
| gtt gca agt gca ctt gcg gaa ctc ctc ccc gta tgg tct cag ctg atc<br>Val Ala Ser Ala Leu Ala Glu Leu Leu Pro Val Trp Ser Gln Leu Ile<br>115                    120                    125 | 384 |
| gaa gag cat agc ctt caa gac ctc aag gcg agc cct cag gcg aag cgg<br>Glu Glu His Ser Leu Gln Asp Leu Lys Ala Ser Pro Gln Ala Lys Arg<br>130                    135                    140 | 432 |
| ctc gac agt gtg agc ttc gcg cac tac tgt gag aag gaa cta aac ttg<br>Leu Asp Ser Val Ser Phe Ala His Tyr Cys Glu Lys Glu Leu Asn Leu<br>145                    150                    155                    160 | 480 |
| cct gct gtt ctc ggc gta gca aac cag atc aca cgc gct ctg ctc ggt<br>Pro Ala Val Leu Gly Val Ala Asn Gln Ile Thr Arg Ala Leu Leu Gly<br>                  165                    170                    175 | 528 |
| gtg gaa gcc cac gag atc agc atg ctt ttt ctc acc gac tac atc aag<br>Val Glu Ala His Glu Ile Ser Met Leu Phe Leu Thr Asp Tyr Ile Lys<br>                  180                    185                    190 | 576 |
| agt gcc acc ggt ctc agt aat att ttc tcg gac aag aaa gac ggc ggg<br>Ser Ala Thr Gly Leu Ser Asn Ile Phe Ser Asp Lys Lys Asp Gly Gly<br>                  195                    200                    205 | 624 |
| cag tat atg cga tgc aaa aca ggt atg cag tcg att tgc cat gcc atg<br>Gln Tyr Met Arg Cys Lys Thr Gly Met Gln Ser Ile Cys His Ala Met<br>210                    215                    220 | 672 |
| tca aag gaa ctt gtt cca ggc tca gtg cac ctc aac acc ccc gtc gct<br>Ser Lys Glu Leu Val Pro Gly Ser Val His Leu Asn Thr Pro Val Ala<br>225                    230                    235                    240 | 720 |
| gaa att gag cag tcg gca tcc ggc tgt aca gta cga tcg gcc tcg ggc<br>Glu Ile Glu Gln Ser Ala Ser Gly Cys Thr Val Arg Ser Ala Ser Gly<br>                  245                    250                    255 | 768 |
| gcc gtg ttc cga agc aaa aag gtg gtg gtt tcg tta ccg aca acc ttg<br>Ala Val Phe Arg Ser Lys Lys Val Val Val Ser Leu Pro Thr Thr Leu<br>                  260                    265                    270 | 816 |
| tat ccc acc ttg aca ttt tca cca cct ctt ccc gcc gag aag caa gca<br>Tyr Pro Thr Leu Thr Phe Ser Pro Pro Leu Pro Ala Glu Lys Gln Ala<br>                  275                    280                    285 | 864 |
| ttg gcg gaa aat tct atc ctg ggc tac tat agc aag ata gtc ttc gta<br>Leu Ala Glu Asn Ser Ile Leu Gly Tyr Tyr Ser Lys Ile Val Phe Val<br>290                    295                    300 | 912 |
| tgg gac aag ccg tgg tgg cgc gaa caa ggc ttc tcg ggc gtc ctc caa<br>Trp Asp Lys Pro Trp Trp Arg Glu Gln Gly Phe Ser Gly Val Leu Gln<br>305                    310                    315                    320 | 960 |
| tcg agc tgt gac ccc atc tca ttt gcc aga gat acc agc atc gac gtc<br>Ser Ser Cys Asp Pro Ile Ser Phe Ala Arg Asp Thr Ser Ile Asp Val<br>                  325                    330                    335 | 1008 |
| gat cga caa tgg tcc att acc tgt ttc atg gtc gga gac ccg gga cgg<br>Asp Arg Gln Trp Ser Ile Thr Cys Phe Met Val Gly Asp Pro Gly Arg<br>                  340                    345                    350 | 1056 |
| aag tgg tcc caa cag tcc aag cag gta cga caa aag tct gtc tgg gac<br>Lys Trp Ser Gln Gln Ser Lys Gln Val Arg Gln Lys Ser Val Trp Asp<br>                  355                    360                    365 | 1104 |
| caa ctc cgc gca gcc tac gag aac gcc ggg gcc caa gtc cca gag ccg<br>Gln Leu Arg Ala Ala Tyr Glu Asn Ala Gly Ala Gln Val Pro Glu Pro<br>370                    375                    380 | 1152 |
| gcc aac gtg ctc gaa atc gag tgg tcg aag cag cag tat ttc caa gga<br>Ala Asn Val Leu Glu Ile Glu Trp Ser Lys Gln Gln Tyr Phe Gln Gly<br>385                    390                    395                    400 | 1200 |
| gct ccg agc gcc gtc tat ggg ctg aac gat ctc atc aca ctg ggt tcg<br>Ala Pro Ser Ala Val Tyr Gly Leu Asn Asp Leu Ile Thr Leu Gly Ser<br>                  405                    410                    415 | 1248 |
| gcg ctc aga acg ccg ttc aag agt gtt cat ttc gtt gga acg gag acg<br>Ala Leu Arg Thr Pro Phe Lys Ser Val His Phe Val Gly Thr Glu Thr | 1296 |

```
                420                425                430
tct tta gtt tgg aaa ggg tat atg gaa ggg gcc ata cga tcg ggt caa      1344
Ser Leu Val Trp Lys Gly Tyr Met Glu Gly Ala Ile Arg Ser Gly Gln
        435                440                445 cga ggt gct gca gaa gtt gtg gct agc ctg gtg cca gca gca tag          1389
Arg Gly Ala Ala Glu Val Val Ala Ser Leu Val Pro Ala Ala *
    450                455                460
```

<210> SEQ ID NO 17
<211> LENGTH: 462
<212> TYPE: PRT
<213> ORGANISM: Exophiala spinifera

<400> SEQUENCE: 17

```
Asp Asn Val Ala Asp Val Val Val Gly Ala Gly Leu Ser Gly Leu
1               5                  10                 15

Glu Thr Ala Arg Lys Val Gln Ala Ala Gly Leu Ser Cys Leu Val Leu
            20                 25                 30

Glu Ala Met Asp Arg Val Gly Gly Lys Thr Leu Ser Val Gln Ser Gly
        35                 40                 45

Pro Gly Arg Thr Thr Ile Asn Asp Leu Gly Ala Ala Trp Ile Asn Asp
    50                 55                 60

Ser Asn Gln Ser Glu Val Ser Arg Leu Phe Glu Arg Phe His Leu Glu
65                 70                 75                 80

Gly Glu Leu Gln Arg Thr Thr Gly Asn Ser Ile His Gln Ala Gln Asp
                85                 90                 95

Gly Thr Thr Thr Thr Ala Pro Tyr Gly Asp Ser Leu Leu Ser Glu Glu
            100                105                110

Val Ala Ser Ala Leu Ala Glu Leu Leu Pro Val Trp Ser Gln Leu Ile
        115                120                125

Glu Glu His Ser Leu Gln Asp Leu Lys Ala Ser Pro Gln Ala Lys Arg
    130                135                140

Leu Asp Ser Val Ser Phe Ala His Tyr Cys Glu Lys Glu Leu Asn Leu
145                150                155                160

Pro Ala Val Leu Gly Val Ala Asn Gln Ile Thr Arg Ala Leu Leu Gly
                165                170                175

Val Glu Ala His Glu Ile Ser Met Leu Phe Leu Thr Asp Tyr Ile Lys
            180                185                190

Ser Ala Thr Gly Leu Ser Asn Ile Phe Ser Asp Lys Lys Asp Gly Gly
        195                200                205

Gln Tyr Met Arg Cys Lys Thr Gly Met Gln Ser Ile Cys His Ala Met
    210                215                220

Ser Lys Glu Leu Val Pro Gly Ser Val His Leu Asn Thr Pro Val Ala
225                230                235                240

Glu Ile Glu Gln Ser Ala Ser Gly Cys Thr Val Arg Ser Ala Ser Gly
                245                250                255

Ala Val Phe Arg Ser Lys Val Val Ser Leu Pro Thr Thr Leu
            260                265                270

Tyr Pro Thr Leu Thr Phe Ser Pro Pro Leu Pro Ala Glu Lys Gln Ala
        275                280                285

Leu Ala Glu Asn Ser Ile Leu Gly Tyr Tyr Ser Lys Ile Val Phe Val
    290                295                300

Trp Asp Lys Pro Trp Trp Arg Glu Gln Gly Phe Ser Gly Val Leu Gln
305                310                315                320

Ser Ser Cys Asp Pro Ile Ser Phe Ala Arg Asp Thr Ser Ile Asp Val
```

-continued

```
                    325                 330                 335
Asp Arg Gln Trp Ser Ile Thr Cys Phe Met Val Gly Asp Pro Gly Arg
                340                 345                 350

Lys Trp Ser Gln Gln Ser Lys Gln Val Arg Gln Lys Ser Val Trp Asp
                355                 360                 365

Gln Leu Arg Ala Ala Tyr Glu Asn Ala Gly Ala Gln Val Pro Glu Pro
            370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
                405                 410                 415

Ala Leu Arg Thr Pro Phe Lys Ser Val His Phe Val Gly Thr Glu Thr
                420                 425                 430

Ser Leu Val Trp Lys Gly Tyr Met Glu Gly Ala Ile Arg Ser Gly Gln
                435                 440                 445

Arg Gly Ala Ala Glu Val Val Ala Ser Leu Val Pro Ala Ala
        450                 455                 460

<210> SEQ ID NO 18
<211> LENGTH: 1392
<212> TYPE: DNA
<213> ORGANISM: Exophiala spinifera
<220> FEATURE:
<221> NAME/KEY: CDS
<222> LOCATION: (1)...(1392)
<220> FEATURE:
<221> NAME/KEY: misc_feature
<222> LOCATION: (0)...(0)
<223> OTHER INFORMATION: truncated APAO with additional Lysine

<400> SEQUENCE: 18 aaa gac aac gtt gcg gac gtg gta gtg gtg ggc gct ggc ttg agc ggt      48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
                 20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
             35                  40                  45 ggt ccc ggc agg acg act atc aac gac ctc ggc gct gcg tgg atc aat     192
Gly Pro Gly Arg Thr Thr Ile Asn Asp Leu Gly Ala Ala Trp Ile Asn
         50                  55                  60 gac agc aac caa agc gaa gta tcc aga ttg ttt gaa aga ttt cat ttg     240
Asp Ser Asn Gln Ser Glu Val Ser Arg Leu Phe Glu Arg Phe His Leu
 65                  70                  75                  80 gag ggc gag ctc cag agg acg act gga aat tca atc cat caa gca caa     288
Glu Gly Glu Leu Gln Arg Thr Thr Gly Asn Ser Ile His Gln Ala Gln
                 85                  90                  95 gac ggt aca acc act aca gct cct tat ggt gac tcc ttg ctg agc gag     336
Asp Gly Thr Thr Thr Thr Ala Pro Tyr Gly Asp Ser Leu Leu Ser Glu
            100                 105                 110 gag gtt gca agt gca ctt gcg gaa ctc ctc ccc gta tgg tct cag ctg     384
Glu Val Ala Ser Ala Leu Ala Glu Leu Leu Pro Val Trp Ser Gln Leu
        115                 120                 125 atc gaa gag cat agc ctt caa gac ctc aag gcg agc cct cag gcg aag     432
Ile Glu Glu His Ser Leu Gln Asp Leu Lys Ala Ser Pro Gln Ala Lys
    130                 135                 140 cgg ctc gac agt gtg agc ttc gcg cac tac tgt gag aag gaa cta aac     480
Arg Leu Asp Ser Val Ser Phe Ala His Tyr Cys Glu Lys Glu Leu Asn
```

```
                  -continued
   145            150            155            160
ttg cct gct gtt ctc ggc gta gca aac cag atc aca cgc gct ctg ctc     528
Leu Pro Ala Val Leu Gly Val Ala Asn Gln Ile Thr Arg Ala Leu Leu
                165            170            175 ggt gtg gaa gcc cac gag atc agc atg ctt ttt ctc acc gac tac atc     576
Gly Val Glu Ala His Glu Ile Ser Met Leu Phe Leu Thr Asp Tyr Ile
            180            185            190 aag agt gcc acc ggt ctc agt aat att ttc tcg gac aag aaa gac ggc     624
Lys Ser Ala Thr Gly Leu Ser Asn Ile Phe Ser Asp Lys Lys Asp Gly
        195            200            205 ggg cag tat atg cga tgc aaa aca ggt atg cag tcg att tgc cat gcc     672
Gly Gln Tyr Met Arg Cys Lys Thr Gly Met Gln Ser Ile Cys His Ala
    210            215            220 atg tca aag gaa ctt gtt cca ggc tca gtg cac ctc aac acc ccc gtc     720
Met Ser Lys Glu Leu Val Pro Gly Ser Val His Leu Asn Thr Pro Val
225            230            235            240 gct gaa att gag cag tcg gca tcc ggc tgt aca gta cga tcg gcc tcg     768
Ala Glu Ile Glu Gln Ser Ala Ser Gly Cys Thr Val Arg Ser Ala Ser
            245            250            255 ggc gcc gtg ttc cga agc aaa aag gtg gtg gtt tcg tta ccg aca acc     816
Gly Ala Val Phe Arg Ser Lys Lys Val Val Val Ser Leu Pro Thr Thr
        260            265            270 ttg tat ccc acc ttg aca ttt tca cca cct ctt ccc gcc gag aag caa     864
Leu Tyr Pro Thr Leu Thr Phe Ser Pro Pro Leu Pro Ala Glu Lys Gln
    275            280            285 gca ttg gcg gaa aat tct atc ctg ggc tac tat agc aag ata gtc ttc     912
Ala Leu Ala Glu Asn Ser Ile Leu Gly Tyr Tyr Ser Lys Ile Val Phe
290            295            300 gta tgg gac aag ccg tgg tgg cgc gaa caa ggc ttc tcg ggc gtc ctc     960
Val Trp Asp Lys Pro Trp Trp Arg Glu Gln Gly Phe Ser Gly Val Leu
305            310            315            320 caa tcg agc tgt gac ccc atc tca ttt gcc aga gat acc agc atc gac    1008
Gln Ser Ser Cys Asp Pro Ile Ser Phe Ala Arg Asp Thr Ser Ile Asp
            325            330            335 gtc gat cga caa tgg tcc att acc tgt ttc atg gtc gga gac ccg gga    1056
Val Asp Arg Gln Trp Ser Ile Thr Cys Phe Met Val Gly Asp Pro Gly
        340            345            350 cgg aag tgg tcc caa cag tcc aag cag gta cga caa aag tct gtc tgg    1104
Arg Lys Trp Ser Gln Gln Ser Lys Gln Val Arg Gln Lys Ser Val Trp
    355            360            365 gac caa ctc cgc gca gcc tac gag aac gcc ggg gcc caa gtc cca gag    1152
Asp Gln Leu Arg Ala Ala Tyr Glu Asn Ala Gly Ala Gln Val Pro Glu
370            375            380 ccg gcc aac gtg ctc gaa atc gag tgg tcg aag cag cag tat ttc caa    1200
Pro Ala Asn Val Leu Glu Ile Glu Trp Ser Lys Gln Gln Tyr Phe Gln
385            390            395            400 gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
            405            410            415 tcg gcg ctc aga acg ccg ttc aag agt gtt cat ttc gtt gga acg gag    1296
Ser Ala Leu Arg Thr Pro Phe Lys Ser Val His Phe Val Gly Thr Glu
        420            425            430 acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
    435            440            445 caa cga ggt gct gca gaa gtt gtg gct agc ctg gtg cca gca gca tag    1392
Gln Arg Gly Ala Ala Glu Val Val Ala Ser Leu Val Pro Ala Ala  *
450            455            460
```

```
<210> SEQ ID NO 19
<211> LENGTH: 463
<212> TYPE: PRT
<213> ORGANISM: Exophiala spinifera

<400> SEQUENCE: 19
```

| | | | | | | | | | | | | | | | |
|---|---|---|---|---|---|---|---|---|---|---|---|---|---|---|---|
| Lys | Asp | Asn | Val | Ala | Asp | Val | Val | Val | Gly | Ala | Gly | Leu | Ser | Gly |
| 1 | | | | 5 | | | | | 10 | | | | | 15 |
| Leu | Glu | Thr | Ala | Arg | Lys | Val | Gln | Ala | Gly | Leu | Ser | Cys | Leu | Val |
| | | | 20 | | | | | 25 | | | | | 30 | |
| Leu | Glu | Ala | Met | Asp | Arg | Val | Gly | Gly | Lys | Thr | Leu | Ser | Val | Gln | Ser |
| | | | 35 | | | | | 40 | | | | | 45 | | |
| Gly | Pro | Gly | Arg | Thr | Thr | Ile | Asn | Asp | Leu | Gly | Ala | Ala | Trp | Ile | Asn |
| | 50 | | | | | 55 | | | | | 60 | | | | |
| Asp | Ser | Asn | Gln | Ser | Glu | Val | Ser | Arg | Leu | Phe | Glu | Arg | Phe | His | Leu |
| 65 | | | | | 70 | | | | | 75 | | | | | 80 |
| Glu | Gly | Glu | Leu | Gln | Arg | Thr | Thr | Gly | Asn | Ser | Ile | His | Gln | Ala | Gln |
| | | | | 85 | | | | | 90 | | | | | 95 | |
| Asp | Gly | Thr | Thr | Thr | Thr | Ala | Pro | Tyr | Gly | Asp | Ser | Leu | Leu | Ser | Glu |
| | | | | 100 | | | | | 105 | | | | | 110 | |
| Glu | Val | Ala | Ser | Ala | Leu | Ala | Glu | Leu | Leu | Pro | Val | Trp | Ser | Gln | Leu |
| | | | 115 | | | | | 120 | | | | | 125 | | |
| Ile | Glu | Glu | His | Ser | Leu | Gln | Asp | Leu | Lys | Ala | Ser | Pro | Gln | Ala | Lys |
| | 130 | | | | | 135 | | | | | 140 | | | | |
| Arg | Leu | Asp | Ser | Val | Ser | Phe | Ala | His | Tyr | Cys | Glu | Lys | Glu | Leu | Asn |
| 145 | | | | | 150 | | | | | 155 | | | | | 160 |
| Leu | Pro | Ala | Val | Leu | Gly | Val | Ala | Asn | Gln | Ile | Thr | Arg | Ala | Leu | Leu |
| | | | | 165 | | | | | 170 | | | | | 175 | |
| Gly | Val | Glu | Ala | His | Glu | Ile | Ser | Met | Leu | Phe | Leu | Thr | Asp | Tyr | Ile |
| | | | 180 | | | | | 185 | | | | | 190 | | |
| Lys | Ser | Ala | Thr | Gly | Leu | Ser | Asn | Ile | Phe | Ser | Asp | Lys | Lys | Asp | Gly |
| | | | 195 | | | | | 200 | | | | | 205 | | |
| Gly | Gln | Tyr | Met | Arg | Cys | Lys | Thr | Gly | Met | Gln | Ser | Ile | Cys | His | Ala |
| | 210 | | | | | 215 | | | | | 220 | | | | |
| Met | Ser | Lys | Glu | Leu | Val | Pro | Gly | Ser | Val | His | Leu | Asn | Thr | Pro | Val |
| 225 | | | | | 230 | | | | | 235 | | | | | 240 |
| Ala | Glu | Ile | Glu | Gln | Ser | Ala | Ser | Gly | Cys | Thr | Val | Arg | Ser | Ala | Ser |
| | | | | 245 | | | | | 250 | | | | | 255 | |
| Gly | Ala | Val | Phe | Arg | Ser | Lys | Lys | Val | Val | Ser | Leu | Pro | Thr | Thr |
| | | | 260 | | | | | 265 | | | | | 270 | | |
| Leu | Tyr | Pro | Thr | Leu | Thr | Phe | Ser | Pro | Pro | Leu | Pro | Ala | Glu | Lys | Gln |
| | | 275 | | | | | 280 | | | | | 285 | | | |
| Ala | Leu | Ala | Glu | Asn | Ser | Ile | Leu | Gly | Tyr | Tyr | Ser | Lys | Ile | Val | Phe |
| | 290 | | | | | 295 | | | | | 300 | | | | |
| Val | Trp | Asp | Lys | Pro | Trp | Trp | Arg | Glu | Gln | Gly | Phe | Ser | Gly | Val | Leu |
| 305 | | | | | 310 | | | | | 315 | | | | | 320 |
| Gln | Ser | Ser | Cys | Asp | Pro | Ile | Ser | Phe | Ala | Arg | Asp | Thr | Ser | Ile | Asp |
| | | | | 325 | | | | | 330 | | | | | 335 | |
| Val | Asp | Arg | Gln | Trp | Ser | Ile | Thr | Cys | Phe | Met | Val | Gly | Asp | Pro | Gly |
| | | | 340 | | | | | 345 | | | | | 350 | | |
| Arg | Lys | Trp | Ser | Gln | Gln | Ser | Lys | Gln | Val | Arg | Gln | Lys | Ser | Val | Trp |
| | | 355 | | | | | 360 | | | | | 365 | | | |
| Asp | Gln | Leu | Arg | Ala | Ala | Tyr | Glu | Asn | Ala | Gly | Ala | Gln | Val | Pro | Glu |
| | 370 | | | | | 375 | | | | | 380 | | | | |

```
Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 20
<211> LENGTH: 1803
<212> TYPE: DNA
<213> ORGANISM: Exophiala spinifera
<220> FEATURE:
<221> NAME/KEY: CDS
<222> LOCATION: (1)...(1800)
<220> FEATURE:
<221> NAME/KEY: misc_feature
<222> LOCATION: (0)...(0)
<223> OTHER INFORMATION: full-length APAO

<400> SEQUENCE: 20 atg gca ctt gca ccg agc tac atc aat ccc cca aac gtc gcc tcc cca        48
Met Ala Leu Ala Pro Ser Tyr Ile Asn Pro Pro Asn Val Ala Ser Pro
1               5                   10                  15 gca ggg tat tct cac gtc ggc gta ggc cca gac gga ggg agg tat gtg        96
Ala Gly Tyr Ser His Val Gly Val Gly Pro Asp Gly Gly Arg Tyr Val
            20                  25                  30 aca ata gct gga cag att gga caa gac gct tcg ggc gtg aca gac cct       144
Thr Ile Ala Gly Gln Ile Gly Gln Asp Ala Ser Gly Val Thr Asp Pro
        35                  40                  45 gcc tac gag aaa cag gtt gcc caa gca ttc gcc aat ctg cga gct tgc       192
Ala Tyr Glu Lys Gln Val Ala Gln Ala Phe Ala Asn Leu Arg Ala Cys
    50                  55                  60 ctt gct gca gtt gga gcc act tca aac gac gtc acc aag ctc aat tac       240
Leu Ala Ala Val Gly Ala Thr Ser Asn Asp Val Thr Lys Leu Asn Tyr
65                  70                  75                  80 tac atc gtc gac tac gcc ccg agc aaa ctc acc gca att gga gat ggg       288
Tyr Ile Val Asp Tyr Ala Pro Ser Lys Leu Thr Ala Ile Gly Asp Gly
                85                  90                  95 ctg aag gct acc ttt gcc ctt gac agg ctc cct cct tgc acg ctg gtg       336
Leu Lys Ala Thr Phe Ala Leu Asp Arg Leu Pro Pro Cys Thr Leu Val
            100                 105                 110 cca gtg tcg gcc ttg tct tca cct gaa tac ctc ttt gag gtt gat gcc       384
Pro Val Ser Ala Leu Ser Ser Pro Glu Tyr Leu Phe Glu Val Asp Ala
        115                 120                 125 acg gcg ctg gtg ccg gga cac acg acc cca gac aac gtt gcg gac gtg       432
Thr Ala Leu Val Pro Gly His Thr Thr Pro Asp Asn Val Ala Asp Val
    130                 135                 140 gta gtg gtg ggc gct ggc ttg agc ggt ttg gag acg gca cgc aaa gtc       480
Val Val Val Gly Ala Gly Leu Ser Gly Leu Glu Thr Ala Arg Lys Val
145                 150                 155                 160 cag gcc gcc ggt ctg tcc tgc ctc gtt ctt gag gcg atg gat cgt gta       528
Gln Ala Ala Gly Leu Ser Cys Leu Val Leu Glu Ala Met Asp Arg Val
            165                 170                 175 ggg gga aag act ctg agc gta caa tcg ggt ccc ggc agg acg act atc       576
Gly Gly Lys Thr Leu Ser Val Gln Ser Gly Pro Gly Arg Thr Thr Ile
        180                 185                 190
```

```
                                    -continued aac gac ctc ggc gct gcg tgg atc aat gac agc aac caa agc gaa gta        624
Asn Asp Leu Gly Ala Ala Trp Ile Asn Asp Ser Asn Gln Ser Glu Val
            195                 200                 205 tcc aga ttg ttt gaa aga ttt cat ttg gag ggc gag ctc cag agg acg        672
Ser Arg Leu Phe Glu Arg Phe His Leu Glu Gly Glu Leu Gln Arg Thr
210                 215                 220 act gga aat tca atc cat caa gca caa gac ggt aca acc act aca gct        720
Thr Gly Asn Ser Ile His Gln Ala Gln Asp Gly Thr Thr Thr Thr Ala
225                 230                 235                 240 cct tat ggt gac tcc ttg ctg agc gag gag gtt gca agt gca ctt gcg        768
Pro Tyr Gly Asp Ser Leu Leu Ser Glu Glu Val Ala Ser Ala Leu Ala
            245                 250                 255 gaa ctc ctc ccc gta tgg tct cag ctg atc gaa gag cat agc ctt caa        816
Glu Leu Leu Pro Val Trp Ser Gln Leu Ile Glu Glu His Ser Leu Gln
            260                 265                 270 gac ctc aag gcg agc cct cag gcg aag cgg ctc gac agt gtg agc ttc        864
Asp Leu Lys Ala Ser Pro Gln Ala Lys Arg Leu Asp Ser Val Ser Phe
            275                 280                 285 gcg cac tac tgt gag aag gaa cta aac ttg cct gct gtt ctc ggc gta        912
Ala His Tyr Cys Glu Lys Glu Leu Asn Leu Pro Ala Val Leu Gly Val
            290                 295                 300 gca aac cag atc aca cgc gct ctg ctc ggt gtg gaa gcc cac gag atc        960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt       1008
Ser Met Leu Phe Leu Thr Asp Tyr Ile Lys Ser Ala Thr Gly Leu Ser
            325                 330                 335 aat att ttc tcg gac aag aaa gac ggc ggg cag tat atg cga tgc aaa       1056
Asn Ile Phe Ser Asp Lys Lys Asp Gly Gly Gln Tyr Met Arg Cys Lys
            340                 345                 350 aca ggt atg cag tcg att tgc cat gcc atg tca aag gaa ctt gtt cca       1104
Thr Gly Met Gln Ser Ile Cys His Ala Met Ser Lys Glu Leu Val Pro
            355                 360                 365 ggc tca gtg cac ctc aac acc ccc gtc gct gaa att gag cag tcg gca       1152
Gly Ser Val His Leu Asn Thr Pro Val Ala Glu Ile Glu Gln Ser Ala
370                 375                 380 tcc ggc tgt aca gta cga tcg gcc tcg ggc gcc gtg ttc cga agc aaa       1200
Ser Gly Cys Thr Val Arg Ser Ala Ser Gly Ala Val Phe Arg Ser Lys
385                 390                 395                 400 aag gtg gtg gtt tcg tta ccg aca acc ttg tat ccc acc ttg aca ttt       1248
Lys Val Val Val Ser Leu Pro Thr Thr Leu Tyr Pro Thr Leu Thr Phe
            405                 410                 415 tca cca cct ctt ccc gcc gag aag caa gca ttg gcg gaa aat tct atc       1296
Ser Pro Pro Leu Pro Ala Glu Lys Gln Ala Leu Ala Glu Asn Ser Ile
            420                 425                 430 ctg ggc tac tat agc aag ata gtc ttc gta tgg gac aag ccg tgg tgg       1344
Leu Gly Tyr Tyr Ser Lys Ile Val Phe Val Trp Asp Lys Pro Trp Trp
            435                 440                 445 cgc gaa caa ggc ttc tcg ggc gtc ctc caa tcg agc tgt gac ccc atc       1392
Arg Glu Gln Gly Phe Ser Gly Val Leu Gln Ser Ser Cys Asp Pro Ile
            450                 455                 460 tca ttt gcc aga gat acc agc atc gac gtc gat cga caa tgg tcc att       1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc       1488
Thr Cys Phe Met Val Gly Asp Pro Gly Arg Lys Trp Ser Gln Gln Ser
            485                 490                 495 aag cag gta cga caa aag tct gtc tgg gac caa ctc cgc gca gcc tac       1536
Lys Gln Val Arg Gln Lys Ser Val Trp Asp Gln Leu Arg Ala Ala Tyr
            500                 505                 510
```

```
gag aac gcc ggg gcc caa gtc cca gag ccg gcc aac gtg ctc gaa atc    1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat    1632
Glu Trp Ser Lys Gln Gln Tyr Phe Gln Gly Ala Pro Ser Ala Val Tyr
530                 535                 540 ggg ctg aac gat ctc atc aca ctg ggt tcg gcg ctc aga acg ccg ttc    1680
Gly Leu Asn Asp Leu Ile Thr Leu Gly Ser Ala Leu Arg Thr Pro Phe
545                 550                 555                 560 aag agt gtt cat ttc gtt gga acg gag acg tct tta gtt tgg aaa ggg    1728
Lys Ser Val His Phe Val Gly Thr Glu Thr Ser Leu Val Trp Lys Gly
            565                 570                 575 tat atg gaa ggg gcc ata cga tcg ggt caa cga ggt gct gca gaa gtt    1776
Tyr Met Glu Gly Ala Ile Arg Ser Gly Gln Arg Gly Ala Ala Glu Val
        580                 585                 590 gtg gct agc ctg gtg cca gca gca tag                                1803
Val Ala Ser Leu Val Pro Ala Ala
            595                 600

<210> SEQ ID NO 21
<211> LENGTH: 600
<212> TYPE: PRT
<213> ORGANISM: Exophiala spinifera

<400> SEQUENCE: 21

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Ser Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
```

-continued

```
                245                 250                 255
Glu Leu Leu Pro Val Trp Ser Gln Leu Ile Glu His Ser Leu Gln
            260                 265                 270
Asp Leu Lys Ala Ser Pro Gln Ala Lys Arg Leu Asp Ser Val Ser Phe
        275                 280                 285
Ala His Tyr Cys Glu Lys Glu Leu Asn Leu Pro Ala Val Leu Gly Val
        290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
            325                 330                 335
Asn Ile Phe Ser Asp Lys Lys Asp Gly Gln Tyr Met Arg Cys Lys
            340                 345                 350
Thr Gly Met Gln Ser Ile Cys His Ala Met Ser Lys Glu Leu Val Pro
            355                 360                 365
Gly Ser Val His Leu Asn Thr Pro Val Ala Glu Ile Glu Gln Ser Ala
        370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Glu Asn Ser Ile
            420                 425                 430
Leu Gly Tyr Tyr Ser Lys Ile Val Phe Val Trp Asp Lys Pro Trp Trp
        435                 440                 445
Arg Glu Gln Gly Phe Ser Gly Val Leu Gln Ser Ser Cys Asp Pro Ile
    450                 455                 460
Ser Phe Ala Arg Asp Thr Ser Ile Asp Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
            500                 505                 510
Glu Asn Ala Gly Ala Gln Val Pro Glu Pro Ala Asn Val Leu Glu Ile
        515                 520                 525
Glu Trp Ser Lys Gln Gln Tyr Phe Gln Gly Ala Pro Ser Ala Val Tyr
    530                 535                 540
Gly Leu Asn Asp Leu Ile Thr Leu Gly Ser Ala Leu Arg Thr Pro Phe
545                 550                 555                 560
Lys Ser Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
            595                 600
```

<210> SEQ ID NO 22
<211> LENGTH: 1803
<212> TYPE: DNA
<213> ORGANISM: Exophiala spinifera
<220> FEATURE:
<221> NAME/KEY: CDS
<222> LOCATION: (1)...(1803)
<220> FEATURE:
<221> NAME/KEY: misc_feature
<222> LOCATION: (0)...(0)

-continued

<223> OTHER INFORMATION: isolate ESP002_C2

<400> SEQUENCE: 22

```
atg gca ctt gca ccg agc tac atc aat ccc cca aac gtc gcc tcc cca        48
Met Ala Leu Ala Pro Ser Tyr Ile Asn Pro Pro Asn Val Ala Ser Pro
  1               5                  10                  15 gca ggg tat tcc cac atc ggc gta ggc cca aac gaa gcg agg tat gtg        96
Ala Gly Tyr Ser His Ile Gly Val Gly Pro Asn Glu Ala Arg Tyr Val
                 20                  25                  30 aca ata gct gga cag att gga caa gac gct ttg ggc gtg aca gac cca       144
Thr Ile Ala Gly Gln Ile Gly Gln Asp Ala Leu Gly Val Thr Asp Pro
             35                  40                  45 gcc tac gag aaa cag gtt gcc caa gca ttc gcc aat ctg cga gct tgc       192
Ala Tyr Glu Lys Gln Val Ala Gln Ala Phe Ala Asn Leu Arg Ala Cys
         50                  55                  60 ctt gct gca gtt gga gcc tct tca aac gac gtc acc aag ctc aat tac       240
Leu Ala Ala Val Gly Ala Ser Ser Asn Asp Val Thr Lys Leu Asn Tyr
 65                  70                  75                  80 tac atc gtc gac tac gcc ccg agc aaa ctc acc gca att gga gat ggg       288
Tyr Ile Val Asp Tyr Ala Pro Ser Lys Leu Thr Ala Ile Gly Asp Gly
                 85                  90                  95 ctg aag tct acc ttt gcc ctt gac agg ctc cct cct tgc acg ctg gtg       336
Leu Lys Ser Thr Phe Ala Leu Asp Arg Leu Pro Pro Cys Thr Leu Val
                100                 105                 110 cca gta ccg gcc ttg gct tca cct gaa tac ctc ttt gag gtt gat gcc       384
Pro Val Pro Ala Leu Ala Ser Pro Glu Tyr Leu Phe Glu Val Asp Ala
            115                 120                 125 acg gcg ctg gtg cca gga cac tcg acc cca gac aac gtt gcg gac gtg       432
Thr Ala Leu Val Pro Gly His Ser Thr Pro Asp Asn Val Ala Asp Val
        130                 135                 140 gta gtg gtg ggc gct ggc ttg agc ggt ttg gag acg gca cgc aaa gtc       480
Val Val Val Gly Ala Gly Leu Ser Gly Leu Glu Thr Ala Arg Lys Val
145                 150                 155                 160 cag gcc gcc ggt ctg tcc tgc ctc gtt ctt gag gcg atg gat cgt gta       528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc       576
Gly Gly Lys Thr Leu Ser Val Gln Ser Gly Pro Gly Arg Thr Thr Ile
                180                 185                 190 aac gac ctc ggc gct gcg tgg atc aat gac agc aac caa agc gaa gta       624
Asn Asp Leu Gly Ala Ala Trp Ile Asn Asp Ser Asn Gln Ser Glu Val
            195                 200                 205 tcc aga ttg ttt gaa aga ttt cat ttg gag ggc gag ctc cag agg acg       672
Ser Arg Leu Phe Glu Arg Phe His Leu Glu Gly Glu Leu Gln Arg Thr
        210                 215                 220 acc gga aat tca atc cat caa gca caa gac ggt aca acc act aca gct       720
Thr Gly Asn Ser Ile His Gln Ala Gln Asp Gly Thr Thr Thr Thr Ala
225                 230                 235                 240 cct tat ggt gac tcc ccg ctg agc gag gag gtt gca agt gca ctt gcg       768
Pro Tyr Gly Asp Ser Pro Leu Ser Glu Glu Val Ala Ser Ala Leu Ala
                245                 250                 255 gaa ctc ctc ccc gta tgg tct cag ctg atc gaa gag tat agc ctt gaa       816
Glu Leu Leu Pro Val Trp Ser Gln Leu Ile Glu Glu Tyr Ser Leu Glu
                260                 265                 270 gac ccc aag gcg agc cct cag gcg aag cgg ctc gac agt gtg agc ttc       864
Asp Pro Lys Ala Ser Pro Gln Ala Lys Arg Leu Asp Ser Val Ser Phe
            275                 280                 285 gcg cac tac tgt gag aag gac cta aac ttg cct gct gtt ctc agc gtg       912
Ala His Tyr Cys Glu Lys Asp Leu Asn Leu Pro Ala Val Leu Ser Val
        290                 295                 300
```

```
gca aac cag atc aca cgc gct ctg ctc ggt gtg gaa gcc cac gag atc     960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt    1008
Ser Met Leu Phe Leu Thr Asp Tyr Ile Lys Ser Ala Thr Gly Leu Ser
                325                 330                 335 aat att gtc tcg gac aag aaa gac ggc ggg cag tat atg cga tgc aaa    1056
Asn Ile Val Ser Asp Lys Lys Asp Gly Gly Gln Tyr Met Arg Cys Lys
            340                 345                 350 aca ggt atg cag tcg att tgc cat gcc atg tca aag gaa ctt gtt cca    1104
Thr Gly Met Gln Ser Ile Cys His Ala Met Ser Lys Glu Leu Val Pro
        355                 360                 365 ggc tca gtg cac ctc aac acc ccc gtc gct gga att gag cag tcg gcg    1152
Gly Ser Val His Leu Asn Thr Pro Val Ala Gly Ile Glu Gln Ser Ala
    370                 375                 380 tcc ggc tgt ata gta cga tcg gcc tcg ggc gcc gtg ttc cga agc aaa    1200
Ser Gly Cys Ile Val Arg Ser Ala Ser Gly Ala Val Phe Arg Ser Lys
385                 390                 395                 400 aag gtg gtg gtt tcg tta ccg aca aca ttg tat ccc acc ttg aca ttt    1248
Lys Val Val Val Ser Leu Pro Thr Thr Leu Tyr Pro Thr Leu Thr Phe
                405                 410                 415 tca cca cct ctt ccc gcc gag aag caa gca ttg gcg gaa aaa tct atc    1296
Ser Pro Pro Leu Pro Ala Glu Lys Gln Ala Leu Ala Glu Lys Ser Ile
            420                 425                 430 ctc ggc tac tat agc aag ata gtc ttc gta tgg gac aac ccg tgg tgg    1344
Leu Gly Tyr Tyr Ser Lys Ile Val Phe Val Trp Asp Asn Pro Trp Trp
        435                 440                 445 cgc gaa caa ggc ttc tcg ggc gtc ctc caa tcg agc tgt gac ccc atc    1392
Arg Glu Gln Gly Phe Ser Gly Val Leu Gln Ser Ser Cys Asp Pro Ile
    450                 455                 460 tca ttt gcc aga gat acc agc atc gaa gtc gat cgg caa tgg tcc att    1440
Ser Phe Ala Arg Asp Thr Ser Ile Glu Val Asp Arg Gln Trp Ser Ile
465                 470                 475                 480 acc tgt ttc atg gtc gga gac ccg gga cgg aag tgg tcc caa cag tcc    1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac    1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc    1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat    1632
Glu Trp Ser Lys Gln Gln Tyr Phe Gln Gly Ala Pro Ser Ala Val Tyr
    530                 535                 540 ggg ctg aac gat ctc atc aca ctg ggt tcg gcg ctc aga acg ccg ttc    1680
Gly Leu Asn Asp Leu Ile Thr Leu Gly Ser Ala Leu Arg Thr Pro Phe
545                 550                 555                 560 aag tgt gtt cat ttc gtt gga acg gag acg tct tta gtt tgg aaa ggg    1728
Lys Cys Val His Phe Val Gly Thr Glu Thr Ser Leu Val Trp Lys Gly
                565                 570                 575 tat atg gaa ggg gcc ata cga tcg ggt caa cga ggt gct gca gaa gtt    1776
Tyr Met Glu Gly Ala Ile Arg Ser Gly Gln Arg Gly Ala Ala Glu Val
            580                 585                 590 gtg gct agc ctg gtg cca gca gca tag                                1803
Val Ala Ser Leu Val Pro Ala Ala *
        595                 600
```

<210> SEQ ID NO 23

```
<211> LENGTH: 600
<212> TYPE: PRT
<213> ORGANISM: Exophiala spinifera

<400> SEQUENCE: 23
```

| | | | | | | | | | | | | | | |
|---|---|---|---|---|---|---|---|---|---|---|---|---|---|---|
|Met|Ala|Leu|Ala|Pro|Ser|Tyr|Ile|Asn|Pro|Asn|Val|Ala|Ser|Pro|
|1| | | |5| | | | |10| | | | |15|
|Ala|Gly|Tyr|Ser|His|Ile|Gly|Val|Gly|Pro|Asn|Glu|Ala|Arg|Tyr|Val|
| | | | |20| | | | |25| | | | |30| |
|Thr|Ile|Ala|Gly|Gln|Ile|Gly|Gln|Asp|Ala|Leu|Gly|Val|Thr|Asp|Pro|
| | | | |35| | | | |40| | | | |45| |
|Ala|Tyr|Glu|Lys|Gln|Val|Ala|Gln|Ala|Phe|Ala|Asn|Leu|Arg|Ala|Cys|
| |50| | | | |55| | | | |60| | | | |
|Leu|Ala|Ala|Val|Gly|Ala|Ser|Ser|Asn|Asp|Val|Thr|Lys|Leu|Asn|Tyr|
|65| | | | |70| | | | |75| | | | |80|
|Tyr|Ile|Val|Asp|Tyr|Ala|Pro|Ser|Lys|Leu|Thr|Ala|Ile|Gly|Asp|Gly|
| | | | |85| | | | |90| | | | |95| |
|Leu|Lys|Ser|Thr|Phe|Ala|Leu|Asp|Arg|Leu|Pro|Pro|Cys|Thr|Leu|Val|
| | | | |100| | | | |105| | | | |110| |
|Pro|Val|Pro|Ala|Leu|Ala|Ser|Pro|Glu|Tyr|Leu|Phe|Glu|Val|Asp|Ala|
| | | | |115| | | | |120| | | | |125| |
|Thr|Ala|Leu|Val|Pro|Gly|His|Ser|Thr|Pro|Asp|Asn|Val|Ala|Asp|Val|
| | | | |130| | | | |135| | | | |140| |
|Val|Val|Val|Gly|Ala|Gly|Leu|Ser|Gly|Leu|Glu|Thr|Ala|Arg|Lys|Val|
|145| | | | |150| | | | |155| | | | |160|
|Gln|Ala|Ala|Gly|Leu|Ser|Cys|Leu|Val|Leu|Glu|Ala|Met|Asp|Arg|Val|
| | | | |165| | | | |170| | | | |175| |
|Gly|Gly|Lys|Thr|Leu|Ser|Val|Gln|Ser|Gly|Pro|Gly|Arg|Thr|Thr|Ile|
| | | | |180| | | | |185| | | | |190| |
|Asn|Asp|Leu|Gly|Ala|Ala|Trp|Ile|Asn|Asp|Ser|Asn|Gln|Ser|Glu|Val|
| | | | |195| | | | |200| | | | |205| |
|Ser|Arg|Leu|Phe|Glu|Arg|Phe|His|Leu|Glu|Gly|Glu|Leu|Gln|Arg|Thr|
| |210| | | | |215| | | | |220| | | | |
|Thr|Gly|Asn|Ser|Ile|His|Gln|Ala|Gln|Asp|Gly|Thr|Thr|Thr|Ala|
|225| | | | |230| | | | |235| | | | |240|
|Pro|Tyr|Gly|Asp|Ser|Pro|Leu|Ser|Glu|Glu|Val|Ala|Ser|Ala|Leu|Ala|
| | | | |245| | | | |250| | | | |255| |
|Glu|Leu|Leu|Pro|Val|Trp|Ser|Gln|Leu|Ile|Glu|Glu|Tyr|Ser|Leu|Glu|
| | | | |260| | | | |265| | | | |270| |
|Asp|Pro|Lys|Ala|Ser|Pro|Gln|Ala|Lys|Arg|Leu|Asp|Ser|Val|Ser|Phe|
| | | | |275| | | | |280| | | | |285| |
|Ala|His|Tyr|Cys|Glu|Lys|Asp|Leu|Asn|Leu|Pro|Ala|Val|Leu|Ser|Val|
| | | | |290| | | | |295| | | | |300| |
|Ala|Asn|Gln|Ile|Thr|Arg|Ala|Leu|Leu|Gly|Val|Glu|Ala|His|Glu|Ile|
|305| | | | |310| | | | |315| | | | |320|
|Ser|Met|Leu|Phe|Leu|Thr|Asp|Tyr|Ile|Lys|Ser|Ala|Thr|Gly|Leu|Ser|
| | | | |325| | | | |330| | | | |335| |
|Asn|Ile|Val|Ser|Asp|Lys|Lys|Asp|Gly|Gln|Tyr|Met|Arg|Cys|Lys|
| | | | |340| | | | |345| | | | |350| |
|Thr|Gly|Met|Gln|Ser|Ile|Cys|His|Ala|Met|Ser|Lys|Glu|Leu|Val|Pro|
| | | | |355| | | | |360| | | | |365| |
|Gly|Ser|Val|His|Leu|Asn|Thr|Pro|Val|Ala|Gly|Ile|Glu|Gln|Ser|Ala|
| | | | |370| | | | |375| | | | |380| |
|Ser|Gly|Cys|Ile|Val|Arg|Ser|Ala|Ser|Gly|Ala|Val|Phe|Arg|Ser|Lys|

```
                385                 390                 395                 400
Lys Val Val Val Ser Leu Pro Thr Thr Leu Tyr Pro Thr Leu Thr Phe
                    405                 410                 415
Ser Pro Pro Leu Pro Ala Glu Lys Gln Ala Leu Ala Glu Lys Ser Ile
                420                 425                 430
Leu Gly Tyr Tyr Ser Lys Ile Val Phe Val Trp Asp Asn Pro Trp Trp
            435                 440                 445
Arg Glu Gln Gly Phe Ser Gly Val Leu Gln Ser Ser Cys Asp Pro Ile
        450                 455                 460
Ser Phe Ala Arg Asp Thr Ser Ile Glu Val Asp Arg Gln Trp Ser Ile
465                 470                 475                 480
Thr Cys Phe Met Val Gly Asp Pro Gly Arg Lys Trp Ser Gln Gln Ser
                    485                 490                 495
Lys Gln Val Arg Gln Lys Ser Val Trp Asp Gln Leu Arg Ala Ala Tyr
                500                 505                 510
Glu Asn Ala Gly Ala Gln Val Pro Glu Pro Ala Asn Val Leu Glu Ile
            515                 520                 525
Glu Trp Ser Lys Gln Gln Tyr Phe Gln Gly Ala Pro Ser Ala Val Tyr
        530                 535                 540
Gly Leu Asn Asp Leu Ile Thr Leu Gly Ser Ala Leu Arg Thr Pro Phe
545                 550                 555                 560
Lys Cys Val His Phe Val Gly Thr Glu Thr Ser Leu Val Trp Lys Gly
                    565                 570                 575
Tyr Met Glu Gly Ala Ile Arg Ser Gly Gln Arg Gly Ala Ala Glu Val
                580                 585                 590
Val Ala Ser Leu Val Pro Ala Ala
            595                 600

<210> SEQ ID NO 24
<211> LENGTH: 1803
<212> TYPE: DNA
<213> ORGANISM: Exophiala spinifera
<220> FEATURE:
<221> NAME/KEY: CDS
<222> LOCATION: (1)...(1803)
<220> FEATURE:
<221> NAME/KEY: misc_feature
<222> LOCATION: (0)...(0)
<223> OTHER INFORMATION: isolate ESP002_C3

<400> SEQUENCE: 24 atg gca ctt gca ccg agc tac atc aat ccc cca aac gtc gcc tcc cca      48
Met Ala Leu Ala Pro Ser Tyr Ile Asn Pro Pro Asn Val Ala Ser Pro
1               5                   10                  15 gca ggg tat tcc cac atc ggc gta ggc cca aac gaa gcg agg tat gtg      96
Ala Gly Tyr Ser His Ile Gly Val Gly Pro Asn Glu Ala Arg Tyr Val
                20                  25                  30 aca ata gct gga cag att gga caa gac gct ttg ggc gtg aca gac cca     144
Thr Ile Ala Gly Gln Ile Gly Gln Asp Ala Leu Gly Val Thr Asp Pro
            35                  40                  45 gcc tac gag aaa cag gtt gcc caa gca ttc gcc aat ctg cga gct tgc     192
Ala Tyr Glu Lys Gln Val Ala Gln Ala Phe Ala Asn Leu Arg Ala Cys
        50                  55                  60 ctt gct gca gtt gga gcc tct tca aac gac gtc acc aag ctc aat tac     240
Leu Ala Ala Val Gly Ala Ser Ser Asn Asp Val Thr Lys Leu Asn Tyr
65                  70                  75                  80 tac atc gtc gac tac gcc ccg agc aaa ctc acc gca att gga gat ggg     288
Tyr Ile Val Asp Tyr Ala Pro Ser Lys Leu Thr Ala Ile Gly Asp Gly
                85                  90                  95
```

| | |
|---|---|
| ctg aag tct acc ttt gcc ctt gac agg ctc cct cct tgc acg ctg gtg<br>Leu Lys Ser Thr Phe Ala Leu Asp Arg Leu Pro Pro Cys Thr Leu Val<br>     100                   105                110 | 336 |
| cca gta ccg gcc ttg gct tca cct gaa tac ctc ttt gag gtt gac gcc<br>Pro Val Pro Ala Leu Ala Ser Pro Glu Tyr Leu Phe Glu Val Asp Ala<br>     115                   120                125 | 384 |
| acg gcg ctg gtg cca gga cac tcg acc cca gac aac gtt gcg gac gtg<br>Thr Ala Leu Val Pro Gly His Ser Thr Pro Asp Asn Val Ala Asp Val<br>     130                   135                140 | 432 |
| gta gtg gtg ggc gct ggc ttg agc ggc ttg gag acg gca cgc aaa gtc<br>Val Val Val Gly Ala Gly Leu Ser Gly Leu Glu Thr Ala Arg Lys Val<br>145               150                155                160 | 480 |
| cag gcc gcc ggt ctg tcc tgc ctc gtt ctt gag gcg atg gat cgt gta<br>Gln Ala Ala Gly Leu Ser Cys Leu Val Leu Glu Ala Met Asp Arg Val<br>                165                170                175 | 528 |
| ggg gga aag act ctg agc gta caa tcg ggt ccc ggc agg acg act atc<br>Gly Gly Lys Thr Leu Ser Val Gln Ser Gly Pro Gly Arg Thr Thr Ile<br>             180                   185                190 | 576 |
| aac gac ctc ggc gct gcg tgg atc aat gac agc aac caa agc gaa gta<br>Asn Asp Leu Gly Ala Ala Trp Ile Asn Asp Ser Asn Gln Ser Glu Val<br>                195                200                205 | 624 |
| tcc aga ttg ttt gaa aga ttt cat ttg gag ggc gag ctc cag agg acg<br>Ser Arg Leu Phe Glu Arg Phe His Leu Glu Gly Glu Leu Gln Arg Thr<br>     210                   215                220 | 672 |
| acc gga aat tca atc cat caa gca caa gac ggt aca acc act aca gct<br>Thr Gly Asn Ser Ile His Gln Ala Gln Asp Gly Thr Thr Thr Thr Ala<br>225               230                235                240 | 720 |
| cct tat ggt gac tcc ccg ctg agc gag gag gtt gca agt gca ctt gcg<br>Pro Tyr Gly Asp Ser Pro Leu Ser Glu Glu Val Ala Ser Ala Leu Ala<br>                245                250                255 | 768 |
| gaa ctc ctc ccc gta tgg tct cag ctg atc gaa gag tat agc ctt gaa<br>Glu Leu Leu Pro Val Trp Ser Gln Leu Ile Glu Glu Tyr Ser Leu Glu<br>             260                   265                270 | 816 |
| gac ccc aag gcg agc cct cag gcg aag cgg ctc gac agt gtg agc ttc<br>Asp Pro Lys Ala Ser Pro Gln Ala Lys Arg Leu Asp Ser Val Ser Phe<br>     275                   280                285 | 864 |
| gcg cac tac tgt gag aag gac cta aac ttg cct gct gtt ctc agc gtg<br>Ala His Tyr Cys Glu Lys Asp Leu Asn Leu Pro Ala Val Leu Ser Val<br>     290                   295                300 | 912 |
| gca aac cag atc aca cgc gct ctg ctc ggt gtg gaa gcc cac gag atc<br>Ala Asn Gln Ile Thr Arg Ala Leu Leu Gly Val Glu Ala His Glu Ile<br>305               310                315                320 | 960 |
| agc atg ctt ttt ctc acc gac tac atc aag agt gcc acc ggt ctc agt<br>Ser Met Leu Phe Leu Thr Asp Tyr Ile Lys Ser Ala Thr Gly Leu Ser<br>                325                330                335 | 1008 |
| aat att gtc tcg gac aag aaa gac ggc ggg cag tat atg cga tgc aaa<br>Asn Ile Val Ser Asp Lys Lys Asp Gly Gly Gln Tyr Met Arg Cys Lys<br>             340                   345                350 | 1056 |
| aca ggt atg cag tcg att tgc cat gcc atg tca aag gaa ctt gtt cca<br>Thr Gly Met Gln Ser Ile Cys His Ala Met Ser Lys Glu Leu Val Pro<br>     355                   360                365 | 1104 |
| ggc tca gtg cac ctc aac acc ccc gtc gct gga att gag cag tcg gcg<br>Gly Ser Val His Leu Asn Thr Pro Val Ala Gly Ile Glu Gln Ser Ala<br>     370                   375                380 | 1152 |
| tcc ggc tgt ata gta cga tcg gcc tcg ggc gcc gtg ttc cga agc aaa<br>Ser Gly Cys Ile Val Arg Ser Ala Ser Gly Ala Val Phe Arg Ser Lys<br>385               390                395                400 | 1200 |
| aag gtg gtg gtt tcg tta ccg aca aca ttg tat ccc acc ttg aca ttt<br>Lys Val Val Val Ser Leu Pro Thr Thr Leu Tyr Pro Thr Leu Thr Phe | 1248 |

```
                    405                 410                 415
tca cca cct ctt ccc gcc gag aag caa gca ttg gcg gaa aaa tct atc    1296
Ser Pro Pro Leu Pro Ala Glu Lys Gln Ala Leu Ala Glu Lys Ser Ile
            420                 425                 430 ctc ggc tac tat agc aag ata gtc ttc gta tgg gac aac ccg tgg tgg    1344
Leu Gly Tyr Tyr Ser Lys Ile Val Phe Val Trp Asp Asn Pro Trp Trp
            435                 440                 445 cgc gaa caa ggc ttc tcg ggc gtc ctc caa tcg agc tgt gac ccc atc    1392
Arg Glu Gln Gly Phe Ser Gly Val Leu Gln Ser Ser Cys Asp Pro Ile
        450                 455                 460 tca ttt gcc aga gat acc agc atc gaa gtc gat cgg caa tgg tcc att    1440
Ser Phe Ala Arg Asp Thr Ser Ile Glu Val Asp Arg Gln Trp Ser Ile
465                 470                 475                 480 acc tgt ttc atg gtc gga gac ccg gga cgg aag tgg tcc caa cag tcc    1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac    1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc    1584
Glu Asn Ala Gly Ala Gln Val Pro Glu Pro Ala Asn Val Leu Glu Ile
            515                 520                 525 gag tgg tcg aag cag cag tat ttc caa gga gct ccg agc gcc gtc tat    1632
Glu Trp Ser Lys Gln Gln Tyr Phe Gln Gly Ala Pro Ser Ala Val Tyr
        530                 535                 540 ggg ctg aac gat ctc atc aca ctg ggt tcg gcg ctc aga acg ccg ttc    1680
Gly Leu Asn Asp Leu Ile Thr Leu Gly Ser Ala Leu Arg Thr Pro Phe
545                 550                 555                 560 aag tgt gtt cat ttc gtt gga acg gag acg tct tta gtt tgg aaa ggg    1728
Lys Cys Val His Phe Val Gly Thr Glu Thr Ser Leu Val Trp Lys Gly
                565                 570                 575 tat atg gaa ggg gcc ata cga tcg ggt caa cga ggt gct gca gaa gtt    1776
Tyr Met Glu Gly Ala Ile Arg Ser Gly Gln Arg Gly Ala Ala Glu Val
            580                 585                 590 gtg gct agc ctg gtg cca gca gca tag                                1803
Val Ala Ser Leu Val Pro Ala Ala  *
            595                 600
```

<210> SEQ ID NO 25
<211> LENGTH: 600
<212> TYPE: PRT
<213> ORGANISM: Exophiala spinifera

<400> SEQUENCE: 25

```
Met Ala Leu Ala Pro Ser Tyr Ile Asn Pro Asn Val Ala Ser Pro
 1               5                  10                  15

Ala Gly Tyr Ser His Ile Gly Val Gly Pro Asn Glu Ala Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110
```

-continued

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Pro Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Ser Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Gly Ile Glu Gln Ser Ala
    370                 375                 380

Ser Gly Cys Ile Val Arg Ser Ala Ser Gly Ala Val Phe Arg Ser Lys
385                 390                 395                 400

Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Asn Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr

-continued

```
                530                 535                 540
Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
                580                 585                 590

Val Ala Ser Leu Val Pro Ala Ala
            595                 600

<210> SEQ ID NO 26
<211> LENGTH: 1803
<212> TYPE: DNA
<213> ORGANISM: Exophiala spinifera
<220> FEATURE:
<221> NAME/KEY: CDS
<222> LOCATION: (1)...(1803)
<220> FEATURE:
<221> NAME/KEY: misc_feature
<222> LOCATION: (0)...(0)
<223> OTHER INFORMATION: isolate ESP002_C12

<400> SEQUENCE: 26 atg gca ctt gca ccg agc tac atc aat ccc cca aac gtc gcc tcc cca      48
Met Ala Leu Ala Pro Ser Tyr Ile Asn Pro Pro Asn Val Ala Ser Pro
  1               5                  10                  15 gca ggg tat tct cac gtc ggc gta ggc cca gac gga ggg agg tat gtg      96
Ala Gly Tyr Ser His Val Gly Val Gly Pro Asp Gly Gly Arg Tyr Val
             20                  25                  30 aca ata gct gga cag att gga caa gac gct tcg ggc gtg aca gac cct     144
Thr Ile Ala Gly Gln Ile Gly Gln Asp Ala Ser Gly Val Thr Asp Pro
         35                  40                  45 gcc tac gag aaa cag gtt gcc caa gca ttc gcc aat ctg cga gct tgc     192
Ala Tyr Glu Lys Gln Val Ala Gln Ala Phe Ala Asn Leu Arg Ala Cys
     50                  55                  60 ctt gct gca gtt gga gcc act tca aac gac gtc acc aag ctc aat tac     240
Leu Ala Ala Val Gly Ala Thr Ser Asn Asp Val Thr Lys Leu Asn Tyr
 65                  70                  75                  80 tac atc gtc gac tac gcc ccg agc aaa ctc acc gca att gga gat ggg     288
Tyr Ile Val Asp Tyr Ala Pro Ser Lys Leu Thr Ala Ile Gly Asp Gly
                 85                  90                  95 ctg aag gct acc ttt gcc ctt gac agg ctc cct cct tgc acg ctg gtg     336
Leu Lys Ala Thr Phe Ala Leu Asp Arg Leu Pro Pro Cys Thr Leu Val
            100                 105                 110 cca gtg tcg gcc ttg tct tca cct gaa tac ctc ttt gag gtt gat gcc     384
Pro Val Ser Ala Leu Ser Ser Pro Glu Tyr Leu Phe Glu Val Asp Ala
        115                 120                 125 acg gcg ctg gtg ccg gga cac acg acc cca gac aac gtt gcg gac gtg     432
Thr Ala Leu Val Pro Gly His Thr Thr Pro Asp Asn Val Ala Asp Val
    130                 135                 140 gta gtg gtg ggc gct ggc ttg agc ggt ttg gag acg gca cgc aaa gtc     480
Val Val Val Gly Ala Gly Leu Ser Gly Leu Glu Thr Ala Arg Lys Val
145                 150                 155                 160 cag gcc gcc ggt ctg tcc tgc ctc gtt ctt gag gcg atg gat cgt gta     528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc     576
Gly Gly Lys Thr Leu Ser Val Gln Ser Gly Pro Gly Arg Thr Thr Ile
            180                 185                 190 aac gac ctc ggc gct gcg tgg atc aat gac agc aac caa agc gaa gta     624
Asn Asp Leu Gly Ala Ala Trp Ile Asn Asp Ser Asn Gln Ser Glu Val
```

```
              195                 200                 205
tcc aga ttg ttt gaa aga ttt cat ttg gag ggc gag ctc cag agg acg     672
Ser Arg Leu Phe Glu Arg Phe His Leu Glu Gly Glu Leu Gln Arg Thr
    210                 215                 220 act gga aat tca atc cat caa gca caa gac ggt aca acc act aca gct     720
Thr Gly Asn Ser Ile His Gln Ala Gln Asp Gly Thr Thr Thr Thr Ala
225                 230                 235                 240 cct tat ggt gac tcc ttg ctg agc gag gag gtt gca agt gca ctt gcg     768
Pro Tyr Gly Asp Ser Leu Leu Ser Glu Glu Val Ala Ser Ala Leu Ala
                245                 250                 255 gaa ctc ctc ccc gta tgg tct cag ctg atc gaa gag cat agc ctt caa     816
Glu Leu Leu Pro Val Trp Ser Gln Leu Ile Glu Glu His Ser Leu Gln
            260                 265                 270 gac ctc aag gcg agc cct cag gcg aag cgg ctc gac agt gtg agc ttc     864
Asp Leu Lys Ala Ser Pro Gln Ala Lys Arg Leu Asp Ser Val Ser Phe
        275                 280                 285 gcg cac tac tgt gag aag gaa cta aac ttg cct gct gtt ctc ggc gta     912
Ala His Tyr Cys Glu Lys Glu Leu Asn Leu Pro Ala Val Leu Gly Val
    290                 295                 300 gca aac cag atc aca cgc gct ctg ctc ggt gtg gaa gcc cac gag atc     960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt    1008
Ser Met Leu Phe Leu Thr Asp Tyr Ile Lys Ser Ala Thr Gly Leu Ser
                325                 330                 335 aat att ttc tcg gac aag aaa gac ggc ggg cag tat atg cga tgc aaa    1056
Asn Ile Phe Ser Asp Lys Lys Asp Gly Gly Gln Tyr Met Arg Cys Lys
            340                 345                 350 aca ggt atg cag tcg att tgc cat gcc atg tca aag gaa ctt gtt cca    1104
Thr Gly Met Gln Ser Ile Cys His Ala Met Ser Lys Glu Leu Val Pro
        355                 360                 365 ggc tca gtg cac ctc aac acc ccc gtc gct gaa att gag cag tcg gca    1152
Gly Ser Val His Leu Asn Thr Pro Val Ala Glu Ile Glu Gln Ser Ala
    370                 375                 380 tcc ggc tgt aca gta cga tcg gcc tcg ggc gcc gtg ttc cga agc aaa    1200
Ser Gly Cys Thr Val Arg Ser Ala Ser Gly Ala Val Phe Arg Ser Lys
385                 390                 395                 400 aag gtg gtg gtt tcg tta ccg aca acc ttg tat ccc acc ttg aca ttt    1248
Lys Val Val Val Ser Leu Pro Thr Thr Leu Tyr Pro Thr Leu Thr Phe
                405                 410                 415 tca cca cct ctc ccc gcc gag aag caa gca ttg gcg gaa aat tct atc    1296
Ser Pro Pro Leu Pro Ala Glu Lys Gln Ala Leu Ala Glu Asn Ser Ile
            420                 425                 430 ctg ggc tac tat agc aag ata gtc ttc gta tgg gac aag ccg tgg tgg    1344
Leu Gly Tyr Tyr Ser Lys Ile Val Phe Val Trp Asp Lys Pro Trp Trp
        435                 440                 445 cgc gaa caa ggc ttc tcg ggc gtc ctc caa tcg agc tgt gac ccc atc    1392
Arg Glu Gln Gly Phe Ser Gly Val Leu Gln Ser Ser Cys Asp Pro Ile
    450                 455                 460 tca ttt gcc aga gat acc agc atc gac gtc gat cga caa tgg tcc att    1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc    1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac    1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc    1584
```

|   |   |   |   |   |   |   |   |   |   |   |   |   |   |   |   |
|---|---|---|---|---|---|---|---|---|---|---|---|---|---|---|---|
| Glu | Asn | Ala | Gly | Ala | Gln | Val | Pro | Glu | Pro | Ala | Asn | Val | Leu | Glu | Ile |
|  |  | 515 |  |  |  | 520 |  |  |  | 525 |  |  |  |  |  |

```
gag tgg tcg aag cag cag tat ttc caa gga gct ccg agc gcc gtc tat     1632
Glu Trp Ser Lys Gln Gln Tyr Phe Gln Gly Ala Pro Ser Ala Val Tyr
    530             535                 540 ggg ctg aac gat ctc atc aca ctg ggt tcg gcg ctc aga acg ccg ttc     1680
Gly Leu Asn Asp Leu Ile Thr Leu Gly Ser Ala Leu Arg Thr Pro Phe
545             550                 555                 560 aag agt gtt cat ttc gtt gga acg gag acg tct tta gtt tgg aaa ggg     1728
Lys Ser Val His Phe Val Gly Thr Glu Thr Ser Leu Val Trp Lys Gly
                565                 570                 575 tat atg gaa ggg gcc ata cga tcg ggt caa cga ggt gct gca gaa gtt     1776
Tyr Met Glu Gly Ala Ile Arg Ser Gly Gln Arg Gly Ala Ala Glu Val
            580                 585                 590 gtg gct agc ctg gtg cca gca gca tag                                 1803
Val Ala Ser Leu Val Pro Ala Ala  *
            595                 600

<210> SEQ ID NO 27
<211> LENGTH: 600
<212> TYPE: PRT
<213> ORGANISM: Exophiala spinifera

<400> SEQUENCE: 27

Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Val Thr Lys Leu Asn Tyr
 65                 70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
                100                 105                 110

Pro Val Ser Ala Leu Ser Ser Pro Glu Tyr Leu Phe Glu Val Asp Ala
            115                 120                 125

Thr Ala Leu Val Pro Gly His Thr Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
                245                 250                 255
```

-continued

```
Glu Leu Leu Pro Val Trp Ser Gln Leu Ile Glu Glu His Ser Leu Gln
            260                 265                 270

Asp Leu Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Asp Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 28
<211> LENGTH: 1803
<212> TYPE: DNA
<213> ORGANISM: Rhinocladiella atrovirens
<220> FEATURE:
<221> NAME/KEY: CDS
<222> LOCATION: (1)...(1803)
<220> FEATURE:
<221> NAME/KEY: misc_feature
<222> LOCATION: (0)...(0)
<223> OTHER INFORMATION: isolate C1
```

<400> SEQUENCE: 28

```
atg gca ctt gca ccg agc tac atc aat ccc cca aac ctc gcc tcc cca    48
Met Ala Leu Ala Pro Ser Tyr Ile Asn Pro Pro Asn Leu Ala Ser Pro
1               5                   10                  15 gca ggg tat tcc cac gtc ggc gta ggc cca aac gga ggg agg tat gcg    96
Ala Gly Tyr Ser His Val Gly Val Gly Pro Asn Gly Gly Arg Tyr Ala
            20                  25                  30 aca ata gct gga cag att gga caa gac gct tcg gcc gtg aca gac cct   144
Thr Ile Ala Gly Gln Ile Gly Gln Asp Ala Ser Ala Val Thr Asp Pro
        35                  40                  45 gcc tac gag aaa cag gtt gcc caa gca ttc gcc aac ctg cga gct tgt   192
Ala Tyr Glu Lys Gln Val Ala Gln Ala Phe Ala Asn Leu Arg Ala Cys
    50                  55                  60 ctt gct gca gtt gga gcc act tca aac gac att acc aag ctc aat tac   240
Leu Ala Ala Val Gly Ala Thr Ser Asn Asp Ile Thr Lys Leu Asn Tyr
65                  70                  75                  80 tac atc gtc gac tac aac ccg agc aaa ctc acc gca att gga gat ggg   288
Tyr Ile Val Asp Tyr Asn Pro Ser Lys Leu Thr Ala Ile Gly Asp Gly
                85                  90                  95 ctg aag gct acc ttt gcc ctt gac agg ctc cct cct tgc acg ctg gtg   336
Leu Lys Ala Thr Phe Ala Leu Asp Arg Leu Pro Pro Cys Thr Leu Val
            100                 105                 110 cca gtg ccg gcc ctg gct tca cct gaa tac ccc ttt gag gtt gat gcc   384
Pro Val Pro Ala Leu Ala Ser Pro Glu Tyr Pro Phe Glu Val Asp Ala
        115                 120                 125 acg gcg ctg gtt cca gga cac tca acc cca gac aat gtt gcg gac gtg   432
Thr Ala Leu Val Pro Gly His Ser Thr Pro Asp Asn Val Ala Asp Val
    130                 135                 140 gtc gtg gtg ggc gct ggc ttg agc ggt ttg gag acg gca cgc aaa gtc   480
Val Val Val Gly Ala Gly Leu Ser Gly Leu Glu Thr Ala Arg Lys Val
145                 150                 155                 160 cag gct gcc ggg ctg tcc tgc ctc gtt ctt gag gcg atg gat cgt gtg   528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg gct atc   576
Gly Gly Lys Thr Leu Ser Val Gln Ser Gly Pro Gly Arg Thr Ala Ile
            180                 185                 190 aat gac ctc ggc gct gcg tgg atc aat gac agc aac caa agc gaa gta   624
Asn Asp Leu Gly Ala Ala Trp Ile Asn Asp Ser Asn Gln Ser Glu Val
        195                 200                 205 ttc aaa tta ttt gaa aga ttt cat ttg gag ggc gag ctc cag agg acg   672
Phe Lys Leu Phe Glu Arg Phe His Leu Glu Gly Glu Leu Gln Arg Thr
    210                 215                 220 acc gga aat tca atc cat caa gca caa gac ggt aca acc act aca gct   720
Thr Gly Asn Ser Ile His Gln Ala Gln Asp Gly Thr Thr Thr Thr Ala
225                 230                 235                 240 cct tat ggt gat tcc ctg ctg agc gag gag gtt gca agt gca ctc gcg   768
Pro Tyr Gly Asp Ser Leu Leu Ser Glu Glu Val Ala Ser Ala Leu Ala
                245                 250                 255 gaa ctc ctt ccc gca tgg tct cag ctg atc gaa gag cat agt ctt gaa   816
Glu Leu Leu Pro Ala Trp Ser Gln Leu Ile Glu Glu His Ser Leu Glu
            260                 265                 270 gac ccc aag gcg agc cct caa gcg aag cag ctc gac agt gtg agc ttc   864
Asp Pro Lys Ala Ser Pro Gln Ala Lys Gln Leu Asp Ser Val Ser Phe
        275                 280                 285 gca cac tac tgt gag aag gat cta agc ttg cct gct gtt ctc ggc gtg   912
Ala His Tyr Cys Glu Lys Asp Leu Ser Leu Pro Ala Val Leu Gly Val
    290                 295                 300 gca aac cag atc aca cgc gct ctg ctc ggt gtg gaa gcc cac gag atc   960
```

```
                Ala Asn Gln Ile Thr Arg Ala Leu Leu Gly Val Glu Ala His Glu Ile
                305                 310                 315                 320 agc atg ctt ttt ctc acc gac tac atc aag agt gcc acc ggt ctc agt              1008
Ser Met Leu Phe Leu Thr Asp Tyr Ile Lys Ser Ala Thr Gly Leu Ser
                325                 330                 335 aat att gtc tcg gat aag aaa gac ggt ggg cag tat atg cga tgc aaa              1056
Asn Ile Val Ser Asp Lys Lys Asp Gly Gly Gln Tyr Met Arg Cys Lys
                340                 345                 350 aca ggt atg cag tcg ctt tgc cat gcc atg tca aag gaa ctt gtt cca              1104
Thr Gly Met Gln Ser Leu Cys His Ala Met Ser Lys Glu Leu Val Pro
                355                 360                 365 ggc tca gtg cac ctc aac acc ccc gtc gcc gaa att gag cag tcg gca              1152
Gly Ser Val His Leu Asn Thr Pro Val Ala Glu Ile Glu Gln Ser Ala
                370                 375                 380 tcc ggc tgt aca gta cga tcg gcc tcg ggc ggc gtg ttc cga agt aaa              1200
Ser Gly Cys Thr Val Arg Ser Ala Ser Gly Gly Val Phe Arg Ser Lys
385                 390                 395                 400 aag gtg gtg gtt tcg tta ccg aca acc ttg tat ccc acc ttg ata ttt              1248
Lys Val Val Val Ser Leu Pro Thr Thr Leu Tyr Pro Thr Leu Ile Phe
                405                 410                 415 tca cca cct ctt ccc gcc gag aag caa gca ttg gct gaa aaa tcc atc              1296
Ser Pro Pro Leu Pro Ala Glu Lys Gln Ala Leu Ala Glu Lys Ser Ile
                420                 425                 430 ctg ggc tac tat agc aag ata gtc ttc gta tgg gac aag ccg tgg tgg              1344
Leu Gly Tyr Tyr Ser Lys Ile Val Phe Val Trp Asp Lys Pro Trp Trp
                435                 440                 445 cgc gaa caa ggc ttc tcg ggc gtc ctc caa tcg agc tgt gac ccc atc              1392
Arg Glu Gln Gly Phe Ser Gly Val Leu Gln Ser Ser Cys Asp Pro Ile
450                 455                 460 tca ttt gcc aga gat acc agc atc gaa gtc gat cgg caa tgg tcc att              1440
Ser Phe Ala Arg Asp Thr Ser Ile Glu Val Asp Arg Gln Trp Ser Ile
465                 470                 475                 480 acc tgt ttc atg gtc gga gac ccg gga cgg aag tgg tcc caa cag tcc              1488
Thr Cys Phe Met Val Gly Asp Pro Gly Arg Lys Trp Ser Gln Gln Ser
                485                 490                 495 aag cag gta cga cag aag tct gtc tgg aac caa ctc cgc gca gcc tac              1536
Lys Gln Val Arg Gln Lys Ser Val Trp Asn Gln Leu Arg Ala Ala Tyr
                500                 505                 510 gag aac gcc ggg gcc caa gtc cca gag ccg gcc aac gtg ctc gag atc              1584
Glu Asn Ala Gly Ala Gln Val Pro Glu Pro Ala Asn Val Leu Glu Ile
                515                 520                 525 gag tgg tcg aag cag cag tat ttc caa gga gcg ccg agc gtc gtc tat              1632
Glu Trp Ser Lys Gln Gln Tyr Phe Gln Gly Ala Pro Ser Val Val Tyr
                530                 535                 540 ggg ctg aac tgt ctc aac aca ctg ggt tcg gcg ctc aga acg ccg ttc              1680
Gly Leu Asn Cys Leu Asn Thr Leu Gly Ser Ala Leu Arg Thr Pro Phe
545                 550                 555                 560 aag ggt gtt cat ttc gtt gga acg gag acg tct ttg gtt tgg aaa ggg              1728
Lys Gly Val His Phe Val Gly Thr Glu Thr Ser Leu Val Trp Lys Gly
                565                 570                 575 tat atg gaa ggg gcc ata cga tcg ggt cag cga ggc gct gca gaa gtt              1776
Tyr Met Glu Gly Ala Ile Arg Ser Gly Gln Arg Gly Ala Ala Glu Val
                580                 585                 590 gtg gct agc ctg gtg cca gca gca tag                                          1803
Val Ala Ser Leu Val Pro Ala Ala  *
                595                 600

<210> SEQ ID NO 29
<211> LENGTH: 600
<212> TYPE: PRT
```

<213> ORGANISM: Rhinocladiella atrovirens

<400> SEQUENCE: 29

```
Met Ala Leu Ala Pro Ser Tyr Ile Asn Pro Asn Leu Ala Ser Pro
  1               5                  10                  15

Ala Gly Tyr Ser His Val Gly Val Gly Pro Asn Gly Gly Arg Tyr Ala
                 20                  25                  30

Thr Ile Ala Gly Gln Ile Gly Gln Asp Ala Ser Ala Val Thr Asp Pro
             35                  40                  45

Ala Tyr Glu Lys Gln Val Ala Gln Ala Phe Ala Asn Leu Arg Ala Cys
 50                      55                  60

Leu Ala Val Gly Ala Thr Ser Asn Asp Ile Thr Lys Leu Asn Tyr
 65                  70                  75                  80

Tyr Ile Val Asp Tyr Asn Pro Ser Lys Leu Thr Ala Ile Gly Asp Gly
                 85                  90                  95

Leu Lys Ala Thr Phe Ala Leu Asp Arg Leu Pro Pro Cys Thr Leu Val
                100                 105                 110

Pro Val Pro Ala Leu Ala Ser Pro Glu Tyr Pro Phe Glu Val Asp Ala
                115                 120                 125

Thr Ala Leu Val Pro Gly His Ser Thr Pro Asp Asn Val Ala Asp Val
            130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Ala Ile
                180                 185                 190

Asn Asp Leu Gly Ala Ala Trp Ile Asn Asp Ser Asn Gln Ser Glu Val
            195                 200                 205

Phe Lys Leu Phe Glu Arg Phe His Leu Glu Gly Glu Leu Gln Arg Thr
        210                 215                 220

Thr Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu His Ser Leu Glu
                260                 265                 270

Asp Pro Lys Ala Ser Pro Gln Ala Lys Gln Leu Asp Ser Val Ser Phe
        275                 280                 285

Ala His Tyr Cys Glu Lys Asp Leu Ser Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Leu Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Gly Val Phe Arg Ser Lys
385                 390                 395                 400
```

-continued

```
Lys Val Val Ser Leu Pro Thr Thr Leu Tyr Pro Thr Leu Ile Phe
            405                 410                 415
Ser Pro Pro Leu Pro Ala Glu Lys Gln Ala Leu Ala Glu Lys Ser Ile
                420                 425                 430
Leu Gly Tyr Tyr Ser Lys Ile Val Phe Val Trp Asp Lys Pro Trp Trp
            435                 440                 445
Arg Glu Gln Gly Phe Ser Gly Val Leu Gln Ser Ser Cys Asp Pro Ile
    450                 455                 460
Ser Phe Ala Arg Asp Thr Ser Ile Glu Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asn Gln Leu Arg Ala Ala Tyr
            500                 505                 510
Glu Asn Ala Gly Ala Gln Val Pro Glu Pro Ala Asn Val Leu Glu Ile
            515                 520                 525
Glu Trp Ser Lys Gln Gln Tyr Phe Gln Gly Ala Pro Ser Val Val Tyr
    530                 535                 540
Gly Leu Asn Cys Leu Asn Thr Leu Gly Ser Ala Leu Arg Thr Pro Phe
545                 550                 555                 560
Lys Gly Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
            595                 600
```

<210> SEQ ID NO 30
<211> LENGTH: 1803
<212> TYPE: DNA
<213> ORGANISM: Rhinocladiella atrovirens
<220> FEATURE:
<221> NAME/KEY: CDS
<222> LOCATION: (1)...(1803)
<220> FEATURE:
<221> NAME/KEY: misc_feature
<222> LOCATION: (0)...(0)
<223> OTHER INFORMATION: isolate C2

<400> SEQUENCE: 30

```
atg gca ctt gca ccg agc tac atc aat ccc cca aac ctc gcc tcc cca     48
Met Ala Leu Ala Pro Ser Tyr Ile Asn Pro Pro Asn Leu Ala Ser Pro
  1               5                  10                  15 gca ggg tat tcc tac gtc ggc gta ggc cca aac gga ggg agg tat gtg     96
Ala Gly Tyr Ser Tyr Val Gly Val Gly Pro Asn Gly Gly Arg Tyr Val
                 20                  25                  30 aca ata gct gga cag att gga caa gac gct tcg gcc gtg aca gac cct    144
Thr Ile Ala Gly Gln Ile Gly Gln Asp Ala Ser Ala Val Thr Asp Pro
             35                  40                  45 gcc tac gag aaa cag gtt gcc caa gca ttc gcc aac ctg cga gct tgt    192
Ala Tyr Glu Lys Gln Val Ala Gln Ala Phe Ala Asn Leu Arg Ala Cys
         50                  55                  60 ctt gct gca gtt gga gcc act tca aac gac att acc aag ctc aat tac    240
Leu Ala Ala Val Gly Ala Thr Ser Asn Asp Ile Thr Lys Leu Asn Tyr
 65                  70                  75                  80 tac atc gtc gac tac aac ccg agc aaa ctc acc gca att gga gat ggg    288
Tyr Ile Val Asp Tyr Asn Pro Ser Lys Leu Thr Ala Ile Gly Asp Gly
                 85                  90                  95 ctg aag gct acc ttt gcc ctt gac agg ctc cct cct tgc acg ctg gtg    336
```

```
                                                           -continued

Leu Lys Ala Thr Phe Ala Leu Asp Arg Leu Pro Pro Cys Thr Leu Val
            100                 105                 110 cca gtg ccg gcc ctg gct tca cct gaa tac ctc ttt gag gtt gat gcc       384
Pro Val Pro Ala Leu Ala Ser Pro Glu Tyr Leu Phe Glu Val Asp Ala
        115                 120                 125 acg gcg ctg gtt cca gga cac tca acc cca gac aat gtt gcg gac gtg       432
Thr Ala Leu Val Pro Gly His Ser Thr Pro Asp Asn Val Ala Asp Val
    130                 135                 140 gtc gtg gtg ggc gct ggc ttg agc ggt ttg gag acg gca cgc aaa gtc       480
Val Val Val Gly Ala Gly Leu Ser Gly Leu Glu Thr Ala Arg Lys Val
145                 150                 155                 160 cag gct gcc ggg ctg tcc tgc ctc gtt ctt gag gcg atg gat cgt gtg       528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc       576
Gly Gly Lys Thr Leu Ser Val Gln Ser Gly Pro Gly Arg Thr Thr Ile
            180                 185                 190 aat gac ctc ggc gct gcg tgg atc aat gac agc aac caa agc gaa gta       624
Asn Asp Leu Gly Ala Ala Trp Ile Asn Asp Ser Asn Gln Ser Glu Val
        195                 200                 205 ttc aaa tta ttt gaa aga ttt cat ttg gag ggc gag ctc cag agg acg       672
Phe Lys Leu Phe Glu Arg Phe His Leu Glu Gly Glu Leu Gln Arg Thr
    210                 215                 220 acc gga aat tca atc cat caa gca caa gac ggt aca acc act aca gct       720
Thr Gly Asn Ser Ile His Gln Ala Gln Asp Gly Thr Thr Thr Thr Ala
225                 230                 235                 240 cct tat ggt gat tcc ctg ctg agc gag gag gtt gca agt gca ctc gcg       768
Pro Tyr Gly Asp Ser Leu Leu Ser Glu Glu Val Ala Ser Ala Leu Ala
                245                 250                 255 gaa ctc ctt ccc gca tgg tct cag ctg atc gaa gag cat agt ctt gaa       816
Glu Leu Leu Pro Ala Trp Ser Gln Leu Ile Glu Glu His Ser Leu Glu
            260                 265                 270 gac ccc aag gcg agc cct caa gcg aag cag ctc gac agt gtg agc ttc       864
Asp Pro Lys Ala Ser Pro Gln Ala Lys Gln Leu Asp Ser Val Ser Phe
        275                 280                 285 gca cac tac tgt gag aag gat cta aac ttg cct gct gtt ctc ggc gtg       912
Ala His Tyr Cys Glu Lys Asp Leu Asn Leu Pro Ala Val Leu Gly Val
    290                 295                 300 gca aac cag atc aca cgc gct ctg ctc ggt gtg gaa gcc cac gag atc       960
Ala Asn Gln Ile Thr Arg Ala Leu Leu Gly Val Glu Ala His Glu Ile
305                 310                 315                 320 agc atg ttt ttt ctc acc gac tac atc aag agt gcc acc ggt ctc agt      1008
Ser Met Phe Phe Leu Thr Asp Tyr Ile Lys Ser Ala Thr Gly Leu Ser
                325                 330                 335 aat att gtc tcg gat aag aaa gac ggt ggg cag tat atg cga tgc aaa      1056
Asn Ile Val Ser Asp Lys Lys Asp Gly Gly Gln Tyr Met Arg Cys Lys
            340                 345                 350 aca ggt atg cag tcg ctt tgc cat gcc atg tca aag gaa ctt gtt cca      1104
Thr Gly Met Gln Ser Leu Cys His Ala Met Ser Lys Glu Leu Val Pro
        355                 360                 365 ggc tca gtg cac ctc aac acc ccc gtc gcc gaa att gag cag tcg gca      1152
Gly Ser Val His Leu Asn Thr Pro Val Ala Glu Ile Glu Gln Ser Ala
    370                 375                 380 tcc ggc tgt aca gta cga tcg gcc tcg ggc ggc gtg ttc cga agt aaa      1200
Ser Gly Cys Thr Val Arg Ser Ala Ser Gly Gly Val Phe Arg Ser Lys
385                 390                 395                 400 aag gtg gtg gtt tcg tta ccg aca acc ttg tat ccc acc ttg ata ttt      1248
Lys Val Val Val Ser Leu Pro Thr Thr Leu Tyr Pro Thr Leu Ile Phe
                405                 410                 415
```

| | | | | | | | | | | | | | | | | |
|---|---|---|---|---|---|---|---|---|---|---|---|---|---|---|---|---|
| tca | cca | cct | ctt | ccc | gcc | gag | aag | caa | gca | ttg | gct | gaa | aaa | tcc | atc | 1296 |
| Ser | Pro | Pro | Leu | Pro | Ala | Glu | Lys | Gln | Ala | Leu | Ala | Glu | Lys | Ser | Ile | |
| | | | 420 | | | | 425 | | | | 430 | | | | | |
| ctg | ggc | tac | tat | agc | aag | ata | gtc | ttc | gta | tgg | gac | aag | ccg | tgg | tgg | 1344 |
| Leu | Gly | Tyr | Tyr | Ser | Lys | Ile | Val | Phe | Val | Trp | Asp | Lys | Pro | Trp | Trp | |
| | | | 435 | | | | 440 | | | | 445 | | | | | |
| cgc | gaa | caa | ggc | ttc | tcg | ggc | gtc | ctc | caa | tcg | agc | tgt | gac | ccc | atc | 1392 |
| Arg | Glu | Gln | Gly | Phe | Ser | Gly | Val | Leu | Gln | Ser | Ser | Cys | Asp | Pro | Ile | |
| | 450 | | | | | 455 | | | | | 460 | | | | | |
| tca | ttt | gcc | aga | gat | acc | agc | atc | gaa | gtc | gat | cgg | caa | tgg | tcc | att | 1440 |
| Ser | Phe | Ala | Arg | Asp | Thr | Ser | Ile | Glu | Val | Asp | Arg | Gln | Trp | Ser | Ile | |
| 465 | | | | 470 | | | | | 475 | | | | | | 480 | |
| acc | tgt | ttc | atg | gtc | gga | gac | ccg | gga | cgg | aag | tgg | tcc | caa | cag | tcc | 1488 |
| Thr | Cys | Phe | Met | Val | Gly | Asp | Pro | Gly | Arg | Lys | Trp | Ser | Gln | Gln | Ser | |
| | | | | 485 | | | | | 490 | | | | | 495 | | |
| aag | cag | gta | cga | cag | aag | tct | gtc | tgg | aac | caa | ctc | cgc | gca | gcc | tac | 1536 |
| Lys | Gln | Val | Arg | Gln | Lys | Ser | Val | Trp | Asn | Gln | Leu | Arg | Ala | Ala | Tyr | |
| | | | 500 | | | | | 505 | | | | | 510 | | | |
| gag | aac | gcc | ggg | gcc | caa | gtc | cca | gag | ccg | gcc | aac | gtg | ctc | gag | atc | 1584 |
| Glu | Asn | Ala | Gly | Ala | Gln | Val | Pro | Glu | Pro | Ala | Asn | Val | Leu | Glu | Ile | |
| | | | 515 | | | | | 520 | | | | | 525 | | | |
| gag | tgg | tcg | aag | cag | cag | tat | ttc | caa | gga | gcg | ccg | agc | gcc | gtc | tat | 1632 |
| Glu | Trp | Ser | Lys | Gln | Gln | Tyr | Phe | Gln | Gly | Ala | Pro | Ser | Ala | Val | Tyr | |
| | 530 | | | | | 535 | | | | | 540 | | | | | |
| ggg | ctg | aac | tgt | ctc | aac | aca | ctg | ggt | tcg | gcg | ctc | aga | acg | ccg | ttc | 1680 |
| Gly | Leu | Asn | Cys | Leu | Asn | Thr | Leu | Gly | Ser | Ala | Leu | Arg | Thr | Pro | Phe | |
| 545 | | | | | 550 | | | | | 555 | | | | | 560 | |
| aag | ggt | gtt | cat | ttc | gtt | gga | acg | gag | acg | tct | ttg | gtt | tgg | aaa | ggg | 1728 |
| Lys | Gly | Val | His | Phe | Val | Gly | Thr | Glu | Thr | Ser | Leu | Val | Trp | Lys | Gly | |
| | | | | 565 | | | | | 570 | | | | | 575 | | |
| tat | atg | gaa | ggg | gcc | ata | cga | tcg | ggt | cag | cga | ggc | gct | gca | gaa | gtt | 1776 |
| Tyr | Met | Glu | Gly | Ala | Ile | Arg | Ser | Gly | Gln | Arg | Gly | Ala | Ala | Glu | Val | |
| | | | 580 | | | | | 585 | | | | | 590 | | | |
| gtg | gct | agc | ctg | gtg | cca | gca | gca | tag | | | | | | | | 1803 |
| Val | Ala | Ser | Leu | Val | Pro | Ala | Ala | * | | | | | | | | |
| | | 595 | | | | | 600 | | | | | | | | | |

<210> SEQ ID NO 31
<211> LENGTH: 600
<212> TYPE: PRT
<213> ORGANISM: Rhinocladiella atrovirens

<400> SEQUENCE: 31

Met Ala Leu Ala Pro Ser Tyr Ile Asn Pro Asn Leu Ala Ser Pro
1               5                   10                  15

Ala Gly Tyr Ser Tyr Val Gly Val Gly Pro Asn Gly Gly Arg Tyr Val
            20                  25                  30

Thr Ile Ala Gly Gln Ile Gly Gln Asp Ala Ser Ala Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Ile Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

-continued

```
Thr Ala Leu Val Pro Gly His Ser Thr Pro Asp Asn Val Ala Asp Val
            130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
                195                 200                 205

Phe Lys Leu Phe Glu Arg Phe His Leu Glu Gly Glu Leu Gln Arg Thr
                210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
                260                 265                 270

Asp Pro Lys Ala Ser Pro Gln Ala Lys Gln Leu Asp Ser Val Ser Phe
                275                 280                 285

Ala His Tyr Cys Glu Lys Asp Leu Asn Leu Pro Ala Val Leu Gly Val
                290                 295                 300

Ala Asn Gln Ile Thr Arg Ala Leu Leu Gly Val Glu Ala His Glu Ile
305                 310                 315                 320

Ser Met Phe Phe Leu Thr Asp Tyr Ile Lys Ser Ala Thr Gly Leu Ser
                325                 330                 335

Asn Ile Val Ser Asp Lys Lys Asp Gly Gln Tyr Met Arg Cys Lys
                340                 345                 350

Thr Gly Met Gln Ser Leu Cys His Ala Met Ser Lys Glu Leu Val Pro
                355                 360                 365

Gly Ser Val His Leu Asn Thr Pro Val Ala Glu Ile Glu Gln Ser Ala
370                 375                 380

Ser Gly Cys Thr Val Arg Ser Ala Ser Gly Gly Val Phe Arg Ser Lys
385                 390                 395                 400

Lys Val Val Val Ser Leu Pro Thr Thr Leu Tyr Pro Thr Leu Ile Phe
                405                 410                 415

Ser Pro Pro Leu Pro Ala Glu Lys Gln Ala Leu Ala Glu Lys Ser Ile
                420                 425                 430

Leu Gly Tyr Tyr Ser Lys Ile Val Phe Val Trp Asp Lys Pro Trp Trp
                435                 440                 445

Arg Glu Gln Gly Phe Ser Gly Val Leu Gln Ser Ser Cys Asp Pro Ile
                450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
                500                 505                 510

Glu Asn Ala Gly Ala Gln Val Pro Glu Pro Ala Asn Val Leu Glu Ile
                515                 520                 525

Glu Trp Ser Lys Gln Gln Tyr Phe Gln Gly Ala Pro Ser Ala Val Tyr
                530                 535                 540
```

-continued

```
Gly Leu Asn Cys Leu Asn Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600
```

<210> SEQ ID NO 32
<211> LENGTH: 1803
<212> TYPE: DNA
<213> ORGANISM: Rhinocladiella atrovirens
<220> FEATURE:
<221> NAME/KEY: CDS
<222> LOCATION: (1)...(1803)
<220> FEATURE:
<221> NAME/KEY: misc_feature
<222> LOCATION: (0)...(0)
<223> OTHER INFORMATION: isolate C4

<400> SEQUENCE: 32

```
atg gca ctt gca ccg agc tac atc aat ccc cca aac ctc gcc tcc cca       48
Met Ala Leu Ala Pro Ser Tyr Ile Asn Pro Pro Asn Leu Ala Ser Pro
1               5                   10                  15 gca ggg tat tcc cac gtc ggc gta ggc cca aac gga ggg agg tat gtg       96
Ala Gly Tyr Ser His Val Gly Val Gly Pro Asn Gly Gly Arg Tyr Val
                20                  25                  30 aca ata gct gga cag att gga caa gac gct tcg gcc gtg aca gac cct      144
Thr Ile Ala Gly Gln Ile Gly Gln Asp Ala Ser Ala Val Thr Asp Pro
            35                  40                  45 gcc tac gag aaa cag gtt gcc caa gca ttc gcc aac ctg cga gct tgt      192
Ala Tyr Glu Lys Gln Val Ala Gln Ala Phe Ala Asn Leu Arg Ala Cys
        50                  55                  60 ctt gct gca gtt gga gcc act tca aac gac att acc aag ctc aat tac      240
Leu Ala Ala Val Gly Ala Thr Ser Asn Asp Ile Thr Lys Leu Asn Tyr
65                  70                  75                  80 tac atc gtc gac tac aac ccg agc aaa ctc acc gca att gga gat ggg      288
Tyr Ile Val Asp Tyr Asn Pro Ser Lys Leu Thr Ala Ile Gly Asp Gly
                85                  90                  95 ctg aag gct acc ttt gcc ctt gac agg ctc cct cct tgc acg ctg gtg      336
Leu Lys Ala Thr Phe Ala Leu Asp Arg Leu Pro Pro Cys Thr Leu Val
                100                 105                 110 cca gtg ccg gcc ctg gct tca cct gaa tac ctc ttt gag gtt gat gct      384
Pro Val Pro Ala Leu Ala Ser Pro Glu Tyr Leu Phe Glu Val Asp Ala
            115                 120                 125 acg gcg ctg gtt cca gga cac tca acc cca gac aat gtt gcg gac gtg      432
Thr Ala Leu Val Pro Gly His Ser Thr Pro Asp Asn Val Ala Asp Val
        130                 135                 140 gtc gtg gtg ggc gct ggc ttg agc ggt ttg gag acg gca cgc aaa gtc      480
Val Val Val Gly Ala Gly Leu Ser Gly Leu Glu Thr Ala Arg Lys Val
145                 150                 155                 160 cag gct gcc ggg ctg tcc tgc ctc gtt ctt gag gcg atg gat cgt gtg      528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc      576
Gly Gly Lys Thr Leu Ser Val Gln Ser Gly Pro Gly Arg Thr Thr Ile
                180                 185                 190 aat gac ctc ggc gct gcg tgg atc aat gac agc aac caa agc gaa gta      624
Asn Asp Leu Gly Ala Ala Trp Ile Asn Asp Ser Asn Gln Ser Glu Val
            195                 200                 205
```

```
ttc aaa tta ttt gaa aga ttt cat ttg gag ggc gag ctc cag agg acg      672
Phe Lys Leu Phe Glu Arg Phe His Leu Glu Gly Glu Leu Gln Arg Thr
    210                 215                 220 acc gga aat tca atc cat caa gca caa gac ggt aca acc act aca gct      720
Thr Gly Asn Ser Ile His Gln Ala Gln Asp Gly Thr Thr Thr Thr Ala
225                 230                 235                 240 cct tat ggt gat tcc ctg ctg agc gag gag gtt gca agt gca ctc gcg      768
Pro Tyr Gly Asp Ser Leu Leu Ser Glu Glu Val Ala Ser Ala Leu Ala
                245                 250                 255 gaa ctc ctt ccc gca tgg tct cag ctg atc gaa gag cat agt ctt gaa      816
Glu Leu Leu Pro Ala Trp Ser Gln Leu Ile Glu Glu His Ser Leu Glu
            260                 265                 270 gac ccc aag gcg agc cct caa gcg aag cag ctc gac agt gtg agc ttc      864
Asp Pro Lys Ala Ser Pro Gln Ala Lys Gln Leu Asp Ser Val Ser Phe
        275                 280                 285 gca cac tac tgt gag aag gat cta aac ttg cct gct gtt ctc ggc gtg      912
Ala His Tyr Cys Glu Lys Asp Leu Asn Leu Pro Ala Val Leu Gly Val
    290                 295                 300 gca aac cag atc aca cgc gct ctg ctc ggt gtg gaa gcc cac gag atc      960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt     1008
Ser Met Leu Phe Leu Thr Asp Tyr Ile Lys Ser Ala Thr Gly Leu Ser
                325                 330                 335 aat att gtc tcg gat aag aaa gac ggt ggg cag tat atg cga tgc aaa     1056
Asn Ile Val Ser Asp Lys Lys Asp Gly Gly Gln Tyr Met Arg Cys Lys
            340                 345                 350 aca ggt atg cag tcg ctt tgc cat gcc atg tca aag gaa ctt gtt cca     1104
Thr Gly Met Gln Ser Leu Cys His Ala Met Ser Lys Glu Leu Val Pro
        355                 360                 365 ggc tca gtg cac ctc aac acc ccc gtc gcc gaa att gag cag tcg gca     1152
Gly Ser Val His Leu Asn Thr Pro Val Ala Glu Ile Glu Gln Ser Ala
    370                 375                 380 tcc ggc tgt aca gta cga tcg gcc tcg ggc ggc gtg ttc cga agt aaa     1200
Ser Gly Cys Thr Val Arg Ser Ala Ser Gly Gly Val Phe Arg Ser Lys
385                 390                 395                 400 aag gtg gtg gtt tcg tta ccg aca acc ttg tat ccc acc ttg ata ttt     1248
Lys Val Val Val Ser Leu Pro Thr Thr Leu Tyr Pro Thr Leu Ile Phe
                405                 410                 415 tca cca cct ctt ccc gcc gag aag caa gca ttg gct gaa aaa tcc atc     1296
Ser Pro Pro Leu Pro Ala Glu Lys Gln Ala Leu Ala Glu Lys Ser Ile
            420                 425                 430 ctg ggc tac tat agc aag ata gtc ttc gta tgg gac aag ctg tgg tgg     1344
Leu Gly Tyr Tyr Ser Lys Ile Val Phe Val Trp Asp Lys Leu Trp Trp
        435                 440                 445 cgc gaa caa ggc ttc tcg ggc gtc ctc caa tcg agc tgt gac ccc atc     1392
Arg Glu Gln Gly Phe Ser Gly Val Leu Gln Ser Ser Cys Asp Pro Ile
    450                 455                 460 tca ttt gcc aga gat acc agc atc gaa gtc gat cgg caa tgg tcc att     1440
Ser Phe Ala Arg Asp Thr Ser Ile Glu Val Asp Arg Gln Trp Ser Ile
465                 470                 475                 480 acc tgt ttc atg gtc gga gac ccg gga cgg aag tgg tcc caa cag tcc     1488
Thr Cys Phe Met Val Gly Asp Pro Gly Arg Lys Trp Ser Gln Gln Ser
                485                 490                 495 aag cag gta cga cag aag tct gtc tgg aac caa ctc cgc gca gcc tac     1536
Lys Gln Val Arg Gln Lys Ser Val Trp Asn Gln Leu Arg Ala Ala Tyr
            500                 505                 510 gag aac gcc ggg gcc caa gtc cca gag ccg gcc aac gtg ctc gag atc     1584
Glu Asn Ala Gly Ala Gln Val Pro Glu Pro Ala Asn Val Leu Glu Ile
        515                 520                 525
```

-continued

```
gag tgg tcg aag cag cag tat ttc caa gga gcg ccg agc gcc gtc tat      1632
Glu Trp Ser Lys Gln Gln Tyr Phe Gln Gly Ala Pro Ser Ala Val Tyr
    530                 535                 540 ggg ctg aac tgt ctc aac aca ctg ggt tcg gcg ctc aga acg ccg ttc      1680
Gly Leu Asn Cys Leu Asn Thr Leu Gly Ser Ala Leu Arg Thr Pro Phe
545                 550                 555                 560 aag ggt gtt cat ttc gtt gga acg gag acg tct ttg gtt tgg aaa ggg      1728
Lys Gly Val His Phe Val Gly Thr Glu Thr Ser Leu Val Trp Lys Gly
                565                 570                 575 tat atg gaa ggg gcc ata cga tcg ggt cag cga ggc gct gca gaa gtt      1776
Tyr Met Glu Gly Ala Ile Arg Ser Gly Gln Arg Gly Ala Ala Glu Val
            580                 585                 590 gtg cct agc ctg gtg cca gca gca tag                                  1803
Val Pro Ser Leu Val Pro Ala Ala  *
                595                 600

<210> SEQ ID NO 33
<211> LENGTH: 600
<212> TYPE: PRT
<213> ORGANISM: Rhinocladiella atrovirens

<400> SEQUENCE: 33

Met Ala Leu Ala Pro Ser Tyr Ile Asn Pro Asn Leu Ala Ser Pro
 1               5                  10                  15

Ala Gly Tyr Ser His Val Gly Val Gly Pro Asn Gly Gly Arg Tyr Val
                20                  25                  30

Thr Ile Ala Gly Gln Ile Gly Gln Asp Ala Ser Ala Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Ile Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270
```

-continued

```
Asp Pro Lys Ala Ser Pro Gln Ala Lys Gln Leu Asp Ser Val Ser Phe
        275                 280                 285

Ala His Tyr Cys Glu Lys Asp Leu Asn Leu Pro Ala Val Leu Gly Val
        290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
                340                 345                 350

Thr Gly Met Gln Ser Leu Cys His Ala Met Ser Lys Glu Leu Val Pro
                355                 360                 365

Gly Ser Val His Leu Asn Thr Pro Val Ala Glu Ile Glu Gln Ser Ala
        370                 375                 380

Ser Gly Cys Thr Val Arg Ser Ala Ser Gly Gly Val Phe Arg Ser Lys
385                 390                 395                 400

Lys Val Val Ser Leu Pro Thr Thr Leu Tyr Pro Thr Leu Ile Phe
                405                 410                 415

Ser Pro Pro Leu Pro Ala Glu Lys Gln Ala Leu Ala Glu Lys Ser Ile
                420                 425                 430

Leu Gly Tyr Tyr Ser Lys Ile Val Phe Val Trp Asp Lys Leu Trp Trp
        435                 440                 445

Arg Glu Gln Gly Phe Ser Gly Val Leu Gln Ser Ser Cys Asp Pro Ile
        450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
                500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
        530                 535                 540

Gly Leu Asn Cys Leu Asn Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
                580                 585                 590

Val Pro Ser Leu Val Pro Ala Ala
                595                 600
```